US006025183A

United States Patent [19]
Soreq et al.

[11] Patent Number: 6,025,183
[45] Date of Patent: Feb. 15, 2000

[54] TRANSGENIC ANIMAL ASSAY SYSTEM FOR ANTI-CHOLINESTERASE SUBSTANCES

[75] Inventors: Hermona Soreq, Rishon le Zion; Haim Zakut, Savyon; Moshe Shani, M.P. Modi'in, all of Israel

[73] Assignee: Yissum Research Development Company of the Hebrew University of Jerusalem

[21] Appl. No.: 08/814,095

[22] Filed: Mar. 6, 1997

Related U.S. Application Data

[63] Continuation-in-part of application No. 08/370,156, Jan. 9, 1995, Pat. No. 5,932,780, which is a continuation-in-part of application No. 08/202,755, Feb. 28, 1994, abandoned.
[60] Provisional application No. 60/031,194, Nov. 20, 1996, and provisional application No. 60/035,266, Dec. 12, 1996.

[51] Int. Cl.[7] .................................................. C12N 1/21
[52] U.S. Cl. .................................... 435/252.3; 435/320.1; 435/69.1; 435/197; 536/23.1; 536/23.5; 536/23.2; 536/24.1
[58] Field of Search ............................ 435/252.3, 320.1, 435/69.1, 197; 536/23.1, 23.5, 23.2, 24.1

[56] References Cited

U.S. PATENT DOCUMENTS

| | | |
|---|---|---|
| 4,736,866 | 4/1988 | Leder et al. . |
| 5,175,383 | 12/1992 | Leder et al. . |
| 5,175,384 | 12/1992 | Krimpenfort et al. . |
| 5,175,385 | 12/1992 | Wagner et al. . |
| 5,221,778 | 6/1993 | Byrne et al. . |
| 5,288,846 | 2/1994 | Quertermous et al. . |
| 5,298,422 | 3/1994 | Schwartz et al. . |
| 5,347,075 | 9/1994 | Sorge . |
| 5,360,735 | 11/1994 | Weinshank et al. . |
| 5,387,742 | 2/1995 | Cordell . |
| 5,464,764 | 11/1995 | Capecchi et al. . |
| 5,487,992 | 1/1996 | Capecchi et al. . |
| 5,595,903 | 1/1997 | Soreq et al. ........................ 435/240.2 |

FOREIGN PATENT DOCUMENTS

| | | |
|---|---|---|
| WO 93/14200 | 7/1993 | WIPO . |
| WO 94/06908 | 3/1994 | WIPO . |
| WO 94/23049 | 10/1994 | WIPO . |
| WO 94/28123 | 12/1994 | WIPO . |

OTHER PUBLICATIONS

Li et al. (1991) "Gene Structure of Mammalian Acetylcholinesterase" *J. Biol. Chem.* 266/34:23083–90, 1991.

Getman et al. (1992) "The Human Gene Encoding Acetylcholinesterase is Located on the Long Arm of Chromosome 7" *Am. J. Hum. Genet.* 51:170–177, 1992.

Aigner et al. (1995) "Overexpression of the neural growth–associated protein GAP–43 induces nerve sprouting in the adult nervous system of transgenic mice" *Cell* 83:269–278.

Aizenman, E. (1988) *Science* 239:1293–1296.

Andres et al. (1996) "Transgenic ACHE induces neuromuscular deterioration in mice" Submitted for publication.

Andrews (1988) "Human teratocarcinomas" *Biochim. Biophys. Acta* 948:17–36.

Anglister and McMahan (1985) "Basal lamina directs acetylcholinesterase accumulation at synaptic sites in regenerating muscle" *J. Cell Biol.* 101:735–743.

Anglister et al. (1994) "Acetylcholinesterase density and turnover number at frog neuromuscular junctions, with modeling of their role in synaptic function" *Neuron* 12:783–794.

Ariel and Daw (1982a) *J. Physiol.* 324:135–160.

Ariel and Daw (1982b) *J. Physiol.* 324:161–186.

Auld et al. (1995) "Glioactin, a novel transmembrane protein on peripheral glia is required to form blood–brain barrier in Drosophila" *Cell* 81:757–767.

Baldessarini (1990) Drugs and the treatment of psychiatric disorders. In: *Pharmacological Basis of Therapeutics*, pp. 383–435, Gilman, Rall, Nies, and Taylor (eds) Pergamon Press, New York.

Beeri et al. (1994) "Testicular amplification and impaired transmission of human butyricholinesterase cDNA in transgenic mice" *Human Reprod.*, 9:284–292.

Beeri et al. (1995) "Transgenic expression of human acetylcholinesterase induces progressive cognitive deterioration in mice" *Current Biology*, 5:1063–1071.

Bickel et al. (1993) "Pharmacologic effects in vivo in brain by vector–mediated peptide drug delivery" *Proc. Natl. Acad. Sci. USA* 90(7):2618–2622.

Bierer et al. (1995) *J. Neurochem.* 64:749–760.

Blackwell et al. (1990) "Sequence–specific DNA binding by the c–Myc protein" *Science* 250:1149–1152.

Bourtchuladze et al. (1994) "Deficient long–term memory in mice with a targeted mutation of the cAMP–responsive element–binding protein" *Cell* 79:59–68.

Brem et al. (1993) "Polymers as controlled drug delivery devised for the treatment of malignant brain tumors" *Eur. J. Pharm. Biopharm.* 39:2–7.

Burke and Olson (1991). "Preparation of Clone Libraries in Yeast Artificial–Chromosome Vectors" in *Methods in Enzymology*, vol. 194, "Guide to Yeast Genetics and Molecular Biology", eds. C. Guthrie and G. Fink, Academic Press, Inc., Chap. 17, pp. 251–270.

Capecchi (1989), "Altering the genome by homologous recombination" *Science*, 244:1288–1292.

Connell et al. (1991) *Proc. Natl. Acad. Sci. USA* 88:723–726.

(List continued on next page.)

*Primary Examiner*—Bradley Sisson
*Assistant Examiner*—Enrique D. Longton
*Attorney, Agent, or Firm*—Kohn & Associates

[57] ABSTRACT

The present invention provides a transgenic animal assay system which provides a model system for testing for, and treatment of, cholinergic deficits and imbalances in mammals such as cognitive functioning in Alzheimer's patients, certain types of retinal photoreceptor degeneration, hematopoietic disorders, and screening for and susceptibility to anti-cholinesterase compounds. The transgenic animals and progeny thereof are transformed with a recombinant expression vector of the present invention. The recombinant expression vector comprises a DNA sequence encoding a heterologous cholinesterase (ChE) enzyme and promoter.

7 Claims, 15 Drawing Sheets

OTHER PUBLICATIONS

Conquet et al. (1994) "Motor deficit and impairment of synaptic plasticity in mice lacking mGluR1" *Nature* 372:237–243.

Dan and Poo, "Retrograde interactions during formation and elkination of neuromuscular synapes" *Curr. Opin. in Neurobiol.* 4:95–100.

Darboux et al. (1996) The structure–function relationships in Drosophila neurotactic show that cholinesterasic domains may have adhesive properties *EMBO J.* 15:4835–4843.

Davies et al. (1992). "Targeted alterations in yeast artificial chromosomes for inter-species gene transfer", *Nucleic Acids Research,* 20(11):2693–2698.

De La Escalera et al. (1990) "Characterization and gene cloning of neurotactin, a Drosophila transmembrane protein related to cholinesterases" *EMBO J.* 9:3593–3601.

Dickinson et al. (1993). "High frequency gene targeting using insertional vectors", *Human Nolecular Genetics,* 2:1299–1302.

Dretchen et al. (1992) "Protection against cocaine toxicity by human butyrylcholinesterase (BCHE) in rat" (abstract) *FASEB J.* 6:A1282.

Drews (1975) "Cholinesterase in embryonic development" *Prog. Histochem. Cytochem* 7:1–52.

Duval, et al. (1992) "H and T subunits of acetylcholinesterase from Torpedo, expressed in COS cells, generate all types of molecular forms" *J. Cell Biol.* 118:641–653.

Eaton and Lambert (1957) "Electromyography and electric stimulation of nerves in diseases of motor unit: observation on the myasthenic syndrome associated with malignant tumors" *JAMA* 163:1117–1124.

Eckstein (1985) "Nucleotide phosporothioates" *Ann. Rev. Biochem.* 54:367–402.

Ehrlich et al. (1992) *Genomics* 13:1192–1197.

Ehrlich et al. (1994) "Population diversity and distinct haplotype frequencies associated with ACHE and BCHE genes of Israeli Jews from Trans–Caucasion Georgia and from Europe" *Genomics* 22:288–295.

Engel and Santa (1971) "Histometric analysis of the ulastructure of the neuromuscular junction in myasthenia gravis and in the myasthenic syndrome" *Ann. N.Y. Acad. Sci.* 183:46–63.

Fitzpatrick–McElligot and Stent (1981) "Appearance and localization of acetylcholinesterase in embryo of the leech Helodbella Triserialis" *J. Neurosci.* 1:901–907.

Freeman, J.A. (1977) *Nature* 269:218–222.

Fuentes and Taylor (1993) "Control of acetylcholinesterase gene expression during myogensis" *Neuron* 10:679–687.

Garcia–Coluna and Miledi (1995) "Effects of serotonergic agents on neuronal nicotinic acetylcholine receptors" *Proc. Natl. Acad. Sci. USA* 92:2919–2923.

Gatley (1991) "Activities of the enantiomers of cocaine and some related compounds as substrates and inhibitors of plasma butyrylcholinesterase" *Biochem. Pharmacol.* 41:1249–1254.

Gavrieli et al. (1992) *J. Cell Biol.* 119:493–501.

Gibney and Taylor (1990) "Biosynthesis of Torpedo acetylcholinesterase in mammalian cells" *J. Biol. Chem.* 265:12576–12583.

Grant et al. (1992) "Impaired long–term potentiation, spatial learning, and hipocampal development in fyn mutant mice" *Science* 258:1903–1909.

Greenberg et al. (1988) "Characterization of a new megakaryocytic cell line—the DAMI cell" *Blood* 72:1968–1977.

Greensmith and Vrbova (1991) "Neuromuscular contacts in the developing rat solleus depend on muscle activity" *Dev. Brain Res.* 62:121–129. [*n/a—will mail in].

Hall (1995) "Laminin b2 (S–Laminin): A new player at the synapse"*Science* 269:362–363.

Han et al. (1991) "Induction of formation of presynaptic terminals in neuroblastoma cells by synapsin IIb" *Nature* 349:697–700.

Hietanen et al. (1990) "Immunocytochemical study of the relations of acetylcholinesterase, enkephalin–, substance P–, choline acetyltransferase– and calcitonin gene–related peptide–immunoreactive structures in the ventral horn of rat spinal cord" *Histochem.* 93:473–477.

Humphries et al. (1992) *Science* 256:804–808.

Hutchins, J.B. (1987) *Exp. Eye Res.* 45:1–38.

Huxley et al. (1991). "The human HPRT gene on a yeast artificial chromosome is functional when transferred to mouse cells by cell fusion", *Genomics,* 9:742–750.

Ichtchenko et al. (1995) "Neuroligin 1: a splice site–specific ligand for beta–neurexins" *Cell* 81:435–443.

Ip et al. (1994) "Neurogenic expression of snail is controlled by separable CNS and PNS promoter elements" *Development* 120:199–207.

Isenschmid, et al. (1989) "A comprehensive study of the stability of cocaine and its metabolites" *J. Anal. Toxicol.* 13:250–256.

Jakobovits et al. (1993). "Germ–line transmission and expression of a human–derived yeast artificial chromosome", *Nature,* 362:255–261.

Jasmin and Gisiger (1990) "Regulation by exercise of the pool of G4 acetylcholinesterase characterizing fast muscles: opposite effect of running training in antagonist muscles" *J. of Neurosci.* 5:1444–1454.

Jones et al. (1993) "Mnd2: a new mouse model of inherited motor neuron disease" *Genomics* 16:669–677.

Jordan et al. (1993) *Nature Genet.* 4:54–57.

Kambam, et al. (1992) "Inhibition of pseudocholinesterase activity protects from cocaine–induced cardiorespiratory toxicity in rats" *J. Lab. Clin. Med.* 119:553–556.

Kambam, et al. (1993) "The effects of inhibition of plasma cholinesterase and hepatic microsomal enzyme activity on cocaine, benzoylecgonine, ecgonine methyl ester, and norocaine blood levels in pigs" *J. Lab. Clin. Med.* 120:323–328.

Karnovsky (1964) "The localization of cholinesterase activity in rat cardiac muscle by electron microscope" *J. Cell Biol.* 23:217–232.

Kawasaki et al. (1993) Uniformly mediated 2'–deoxy–2'–fluoro phosphorothioate oligonucleotides as nuclease–resistant antisense compounds with high affinity and specificity for RNA targets, *J. Med. Chem.,* 36:831.

Koenig, et al (1987) "Complete cloning of the Duchenne muscular dystrophy (DMD) cDNA and preliminary genomic organization of the DMD gene in normal and affected individuals" *Cell* 50:509–517.

Lamb et al. (1993). "Introduction and expression of the 400 kilobase precursor amyloid protein gene in transgenic mice", *Nature Genetics,* 5:22–29.

Lambert and Elmquist, (1971) "Quantal components of end plate potentials in the myasthenic syndrome"*Ann. NY Acad. Sci.* 183:183–199.

Langdon and Freeman (1987) *J. Neurosci.* 7:760–773.

Layer et al. (1993) "Cholinesterases regulate neurite growth of chick nerve cells in vitro by means of a non–enzymatic mechanism", *Cell Tissue Res.* 273, 219–226.

Layer et al. (1992) *Cell Tissue Res.* 268:409–418.
Layer, P.G., (1995) "Nonclassical Roles of Cholinesterases in the Embryonic Brain and Possible Links to Alzheimer Disease", *Alz. Dis. Assoc. Disord.* 9:29–36.
Liang and Pardee (1992) "Differential display of eukaryotic messenger RNA by means of the polymerase chain reaction" *Science* 257:967–971.
Lipton et al. (1988) *Science* 239:1293–1296.
Loewenstein–Lichtenstein et al. (1995) "Genetic predisposition to adverse consequences of anti–cholinesterase in "Atypical" BCHE carriers" *Nature/Medicine* 1:1082–1085.
Lolley et al. (1994) *Invest. Ophthalmol. Vis. Sci.* 35, 358–362.
Low (1987) "Biochemistry of the glycosyl–phospatidylinositol membrane protein anchor" *Biochem J.* 244:1–13.
Lyons and Slater (1991) "Structure and function of the neuromuscular function in young adult mdx mice" *J. Neurocytol* 20:969–981.
Marc, R.E. (1986) *Vision Res.* 26:223–238.
Masland and Tauchi (1986) *Trends Neurosci.* 9:218–223.
Massoulie et al. (1992) (Shafferman and Velan, eds., Plenum Press, N.Y.) pp. 285–288.
Massoulie et al. (1993) "Molecular and cellular biology of cholinesterases" *Progress in Neurobiology* 41, 31–91.
Masu et al. (1993) "Disruption of the CNTF gene results in motor neuron degeneration" *Nature* 365:27–32.
McGuire et al. (1995) *Hum. Genet.* 95:71–74.
McNamara and Skelton (1993) "The neuropharmacological and neurochemical basis of place learning in the Morris water maze" *Brain Res. Reviews* 18:33–49.
Meneely et al. (1989) "Effects of the organophosphate insecticides Diazinon and Parathion on bobwhite quail embryos: skeletal defects and acetylcholinesterase activity" *J. Exp. Zool.* 252:60–70.
Millar et al. (1985) *Neurosci. Lett.* 61:311–316.
Millard and Broomfield (1995) "Anticholinesterases: medical applications of neurochemical principles" *J. Neurochem.* 64:1909–1918.
Morris et al. (1981) "Place navigation impaired in rats with hippocampal lesions" *Nature* 297:681–682.
Mullen and Lavail (1976) *Science* 192:799–801.
Mutero et al. (1995) "Promoter elements of the mouse acetycholinesterase gene" *J. Biol. Chem.* 270:1866–1872.
Nishikawa and Sasaki (1993) "Secretion of chondroitin sulfate from embryonic epidermal cells in *Xenopus laevis*" *J. Histochem. Cytochem.* 9:1373–1381.
Noakes et al. (1995) "Aberrant differentiation of neuromuscular junctions in mice lacking S–laminin/laminin b2" *Nature* 374:258–262.
Paoletti et al. (1992) "Acetylcholinesterase in murine erythroleukemia (Friend) cells: evidence for megakaryocyte–like expression and potential growth–regulatory role of enzyme activity" *Blood* 79:2873–2879.
Pavlath et al. (1989) "Localizationof muscle gene products in nuclear domains" *Nature* 337:570–573.
Pearson and Choi (1993), Express of the human β–amyloid precursor protein gene from yeast artificial chromosome in transgenic mice. Proc. Natl. Scad. Sci. USA, 90:10578–82.
Pittler and Baehr (1991) *Proc. Natl. Acad. Sci. USA* 88:8322–8326.
Pressman–Schwartz et al. (1992) "A 69–kDa RNA–binding protein from Xenopus oocytes recognizes a common motif in two vegetally localized material mRNAs" *Proc. Natl. Acad. Sci. USA* 89:11895–11899.

Prody et al. (1989) "De novo amplification within a "silent" human cholineterase gene in a family subjected to prolonged exposure to organophosphorous insecticides" *Proc. Natl. Acad. Sci. USA* 86:690–694.
Rachinsky et al. (1990) "Molecular cloning of mouse acetylcholinesterase: tissue distribution of alternatively spliced mRNA species" *Neuron* 5:317–327.
Ralston and Hall (1989) "Transfer of a protein encoded by a single nucleus to nearby nuclei in multinucleated mytobes" *Nature* 244:1066–1069.
Roberts et al. (1991) "Bovine brain acetylcholinesterase primary sequence involved in intersubunit disulfide linkages" *J. Biol Chem.* 266:7481–7487.
Robertson and Yu (1993) *NIPS* 8:266–272.
Rothstein (1991) "Targeting, disruption, replacement, and allele rescue: integrative DNA transformation in yeast" in *Methods in Enzymology,* vol. 194, "Guide to Yeast Genetics and Molecular Biology", eds. C. Guthrie and G. Fink, Academic Press, Inc. Chap. 19, pp. 281–301.
Sakimura et al. (1995) "Reduced hippocampal LTP and spatial learning in mice lacking NMDA receptor_1 subunit" *Nature* 373:151–155.
Salpeter (1967) "Electron microscope radioautography as a quantitative tool in enzyme cytochemistry I: The distribution of acetylcholinesterase at motor endplates of a vertebrate twitch muscle" *J. Cell Biol.* 32:379–389.
Schaeffer et al. (1994) "Synapsin IIa accelerates functional development of neuromuscular synapses" *Proc. Natl. Acad. Sci. USA* 91:3882–3886.
Schedl et al. (1993). "A yeast artificial chromosome covering the tyrosinase gene confers copy number–dependent expression in transgenic mice", *Nature,* 362:258–261.
Schmidt, J. (1988) *Int. Rev. Neurobiol.* 30:1–38.
Schwarz et al. (1995) "Engineering of human cholinesterases explains and predicts–diverse consequences of administration of various drugs and poisons" *Pharmacology and Therapeutics* 67:283–322.
Seidman and Soreq (1996) "Transgenic Xenopus microinjection methods and developmental neurobiology" in Humana Press, Neuromethods series, (in press). Abstract.
Seidman et al. (1995) "Synaptic and epidermal accumulations of human acetycholinesterase are encoded by alternative 3'–terminal exons" *Mol. Cell Biol.* 15:2993–3002.
Shani (1985) "Tissue specific expression of rat myosin light chain 3 gene in transgenic mice" *Nature* 314:283–286.
Shani et al. (1992) "Expression of human serum albumin in the milk of transgenic mice" *Transgen. Res.* 1:192–208.
Shapira et al. (1994) "Transgenic engineering of neuromuscular junctions in *Xenopus laevis* embryos transiently over-expressing key cholinergic proteins" *Proc. Natl. Acad. Sci. USA* 91:9072–9076.
Shastry, B.S. (1994) *Amer. J. Med. Gen.* 53:467–474.
Shatz, C.J. (1996) *Proc. Natl. Acad. Sci. USA* 93:602–608.
Silva et al. (1992) "Impaired spatial learning in a–calcium–calmodulin kinase II mutant mice" *Science* 257: 206–211.
Simpson et al. (1994) "Prostaglandins and hypothalamic neurotransmitter receptors involved in hypothermia: a critical evaluation" *Neurosci. Behavior Rev.*18:1–20.
Small et al. (1995) "Cholinergic Regulation of Neurite Outgrowth from Isolated Chick–Sympathetic Neurons in Culture" *J. Neurosci.* 15:144–151.
Sokol et al. (1991) "Injected Wnt RNA induces a complete body axis in Xenopus embryos" *Cell* 67:741–752.

Strauss et al. (1993). "Germ line transmission of a yeast artificial chromosome spanning the murine $\alpha_1$ (I) collagen locus", *Science,* 259:1904–1907.

Sung et al. (1994) *J. Neurosci.* 14:5818–5833.

Thomas et al. (1982) "Anterior horn cell dysfunction in Alzheimer's disease" *J. Neurol. Neurosurg. and Psychiatry* 45:378–381.

Toutant et al. (1990) "Molecular forms of acetylcholinesterase in two sublines of human erythroleukemia K562 cells—sensitivity or resistance to phosphatidylinositol-specific phospholipase C and biosynthesis" *Eur. J. Biochem.* 187:31–38.

Ushkariov et al. (1992) "Neurexins: synaptic cell surface proteins related to the a–latrotoxin receptor and laminin" *Science* 257:50–56.

Vaney et al. (1981) *J. Comp Neurol.* 199:373–391.

Westaway et al. (1994) "Degeneration of skeletal muscle, peripheral nerves, and the central nervous system in transgenic mice overexpressing wild-type prion proteins" *Cell* 76:117–129.

Wokke et al. (1990) "Morphological changes in the human end plate with age" *J. of Neurological Sciences* 95:291–310.

Wurtman (1992) "Choline metabolism as a basis for the selective vulnerability of cholinergic neurons" *TINS* 5:117–112.

Zakut et al. (1994) "Turning of nerve growth cones induced by neurotransmitters" *Nature* 368:140–144.

Zon et al. (1991) "Expression of GATA–binding proteins during embryonic development in *Xenopus laevis*" *Proc. Natl. Acad. Sci. USA* 88:10642–10646.

Anglister and McMahan, "Basal lamina directs acetylcholinesterase accumulation of synaptic sites in regenerating muscle" *J. Cell Biol.,* 101:735–743 (1985).

Bartels et al., "Mutation at Codon 322 in the human acetylcholinesterase (ACHE) gene accounts for YT blood . . . " *Am. J. Hum. Genet.,* 52:928–936 (1993).

Ben Aziz–Aloya et al., "Expression of a human acetylcholinesterase promoter–reporter construct in developing neuromuscular . . . " *Proc. Natl. Acad. Sci. USA,* 90:2471–2475 (1993).

Betz et al., in *Basic Neurochem.* Molecular Cell, (Raven Press Ltd, NY) 5th Ed., pp. 681–699 (1994).

Billett and Gould, "Fine ultrastructural changes in the differentiating epidermis . . . " *J. Anat.,* 108:465–480 (1971).

Brodbeck and Liao, "Subunit assembly and glycosylation . . . " in *Multidisciplinary Approaches to Cholinesterase Functions* (Shafferman and Velan, eds.), pp. 33–38 Plenum Press, NY (1992).

Clement, "Hypothermia:–limited tolerance to repeated soman administration and cross–tolerance to oxothreomorine" *Biochem. Behav.,* 39:929–934 (1991).

Coyle et al., "Alzheimer's Disease: a disorder of cortical cholinergic innervation" *Science,* 219:1186–1189 (1983).

Fournier et al., "Drosophila acetycholinesterase: expression of a functional precursor in Xenopus oocytes" *Eur. J. Biochem.,* 203:513–519 (1992).

Gennari and Brodbeck, "Molecular forms of acetycholinesterase from human caudate nucleus, comparison of salt–soluble . . . " *J. Neurochem.,* 44:697–704 (1985).

Gnatt et al., "Expression of alternatively terminated unusual human butyrylcholinestersase messenger RNA transcripts . . . " *Cancer Res.,* 50:1983–1987 (1990).

Inestrosa et al., Acetylcholinesterase from bovine caudate nucleus is attached to membranes by a novel subunit . . . *J. Biol. Chem.,* 262:4441–4444 (1987).

Jasmin et al., "Compartmentalization of acetylcholinesterase mRNA and enzyme at the vertebrate neuromuscular junction" *Neuron,* 11:467–477 (1993).

Jennekens et al., "Deficiency of acetylcholine receptors in a case of end–plate acetylcholinesterase . . . " *Muscle and Nerve,* 15:63–72 (1992).

Karpel et al., "Expression of three alternative acetycholinesterase messenger RNAs in human tumor cell lines . . . " *Exptl. Cell. Res.,* 210:268–277 (1984).

Knapp et al., "A 30–week randomized controlled trial of high–dose tacrine in patients with Alzhemier's disease" *J.Am.Med.Assn.,* 271:985–991 (1994).

Krejci et al., "Primary structure of a collagenic tail peptide of Torpedo acetylcholinesterase . . . " *EMBO J.,* 10:1285–1293 (1991).

Kronman et al., "Production and secretion of high levels of recombinant human acetylcholinesterase in cultured . . . " *Gene,* 121:295–304 (1992).

Lapidot–Lifson et al., "Cloning and antisense oligodeoxynucleotides inhibition of a human homolog . . . " *Proc. Natl. Acad. Sci. USA,* 89:579–583 (1992).

Lapidot–Lifson et al., "Co–amplification of human acetylcholinesterase and butyrylcholinesterase in blood cells . . . " *Proc. Natl. Acad. Sci. USA,* 86:4715–4717 (1989).

Legay et al., "Expression of a cDNA encoding the glycolipid–anchored form of rat acetycholinesterase" *FEBS Lett.,* 315:163–166 (1993b).

Lev–Lehman et al., "Antisense inhibition of acetylcholinesterase gene expression causes transient hematopoietic . . . " *Gene Therapy,* 1:1–11 (1993).

Li et al., "Gene structure of mammalian acetylcholinesterase: alternative exons dictate tissue specific expression" *J. Biol. Chem.,* 266:23083–23090 (1991).

Li et al., "Tissue–specific expression and alternative mRNA processing of the mammalian acetylcholinesterase gene" *J. Biol. Chem.,* 268:5790–5797 (1993).

Liao et al., "Different glycosylation in acetylcholinesterase from mammalian brain and erythrocytes" *J. Neurochem.,* 58:1230–1238 (1992).

Loewenstein et al., "Molecular dissection of cholinesterase domains responsible for carbamate toxicity" *Chem.–Biol. Interactions,* 87:209–216 (1993).

Massoulie et al., "Biosynthesis of the molecular forms . . . " in *Multidisciplinary Approaches to Cholinesterase Functions,* ed. by Shafferman and Velan, Plenum Press, NY, pp. 17–24 (1992).

Millard and Broomfield, "Biology of Cholinesterase Inhibitors" *J. Neurochem.,* (In press, 1995).

Navaratnam, "Anomalous molecular form of acetycholinesterase in cerebrospinal fluid in histologically diagnosed Alzheimer's disease" *Lancet,* 337:447–450 (1991).

Neville et al., "Intramolecular relationships in cholinesterases revealed by oocyte expression . . . " *EMBO J.,* 11:1641–1649 (1992).

Newhouse et al., "Modeling the nicotinic receptor loss in dementia using the nicotinic antagonist mecamylamine . . . " *Drug. Dev. Res.,* 31:71–79 (1994).

Pardridge, et al. "Blood–brain barrier and new approaches to brain drug delivery" *West J. Med.,* 156(3):281–286 (1992).

Pardridge, "Recent developments in peptide drug delivery to the brain" *Pharm. Toxicol.,* 71(1):3–10 (1992).

Patinkin et al., "Manipulations of cholinesterase gene expression modulate murine megakaryocytopoiesis in vitro" *Mol. Cell Biol.,* 10:6046–6050 (1990).

Plump et al., "Severe hypercholesterolemia and atherosclerosis in apolipoproterin E–deficient mice created . . . " *Cell,* 71:343–353 (1992).

Prody et al., "Isolation and characterization of full–length cDNA clones coding for cholinesterase from fetal human tissue" *Proc. Natl. Acad. Sci. USA* 84:3555–3559 (1987).

Rubinstein et al., "A lymphocyte cell line that makes serum cholinesterase instead of acetylcholinesterase" *Biochem. Gen.,* 22:1171–1175.

Schmidt et al., "The cytomegalovirus enhancer: a panactive control element in transgenic mice" *Molec. Cell. Biol.,* 10:4406–4411 (1990).

Seidman et al., "Overexpressed monomeric human acetylcholinesterase induces subtle ultrastructural modifications . . . " *J. Neurochem.,* 62:1670–1681 (1994).

Shani, "Tissue specific expression of rat myosin light chain 3 gene in transgenic mice" *Nature,* 314:283–286 (1985).

Sher et al., "Voltage–operated calcium channels in small cell lung carcinoma cell lines . . . " *Cancer Res.,* 50:3892–3896 (1990).

Sikorav et al., "Complex alternative splicing of acetylcholinesterase transcripts in Torpedo electric organ . . . " *EMBO J.,* 7:2983–2993 (1988).

Soreq et al., "Molecular cloning and construction of the coding region for human acetylcholinesterase reveals a G,C rich . . . " *Proc. Natl. Acad. Sci. USA,* 87:9688–9692 (1990).

Soreq et al., "A role for cholinesterases in tumorigenesis?" *Cancer cells,* 3:511–516 (1991).

Soreq et al., "Expression and tissue specific assembly of cloned human butyrylcholine esterase in microinjected . . . " *J. Biol. Chem.,* 264:10608–10613 (1989).

Soreq and Zakut "Human cholinesterases and anti–cholinesterases" Academic Press (1993), NY table.

Velan et al., "Recombinant human acetylcholinesterase is secreted from transiently transfected 293 cells . . . " *Cell. Mol. Neurobiol.,* 11:143–156 (1991a).

Velan et al., "The effect of elimination of intersubunit disulfide bonds on the activity, assembly and secretion . . . " *J. Biol. Chem.,* 266:23977–23984 (1991b).

Zakut et al., "Acetylcholinesterase and butyrylcholinesterase genes coamplify in primary ovarian carcinomas" *J. Clin. Invest.,* 86:900–908 (1990).

Zakut et al., "Modified properties of serum cholinesterases in primary carcinomas" *Cancer,* 61:727–737 (1991).

Zakut et al., "In vivo gene amplification in non–carcerous cells; cholinesterase genes and oncogenes . . . " *Mutation Research,* 276:275–284 (1992).

Zakut et al., "Chorionic villus cDNA library displays expression of butyrylcholinesterase . . . " *Prenatal Diagnosis,* 11:597–607 (1991).

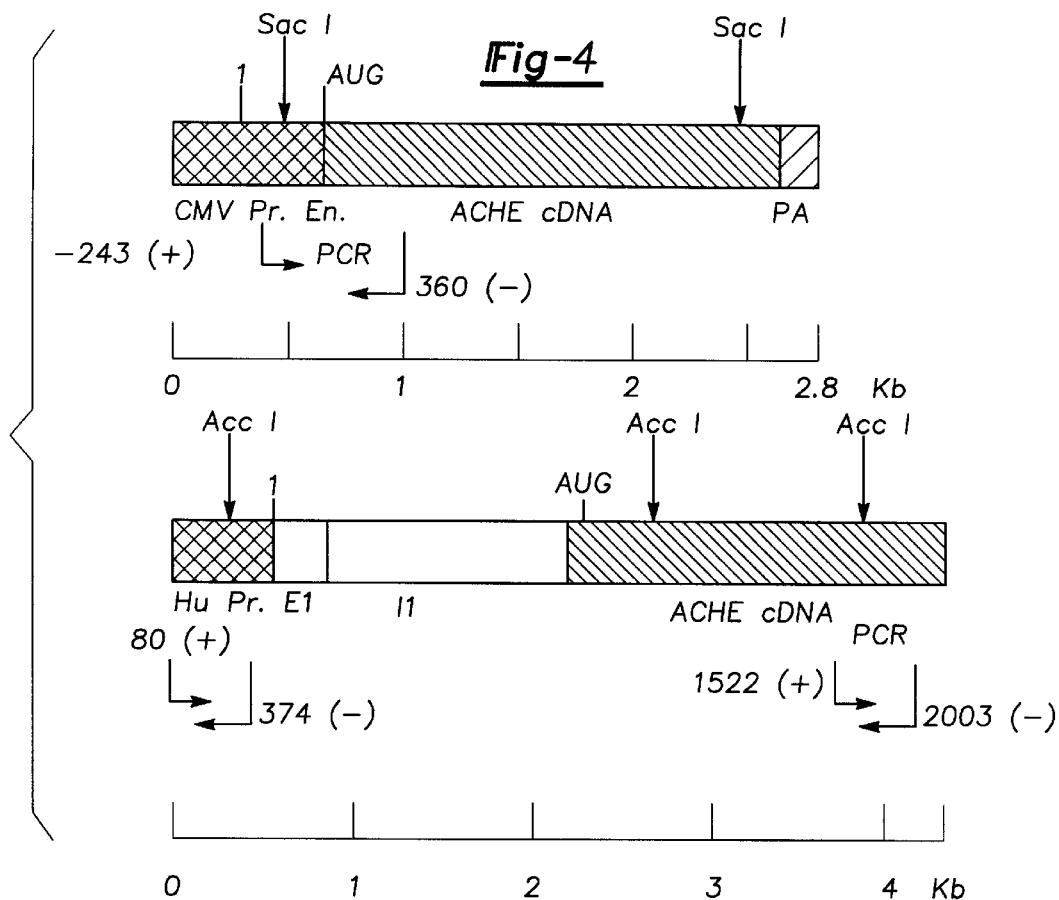
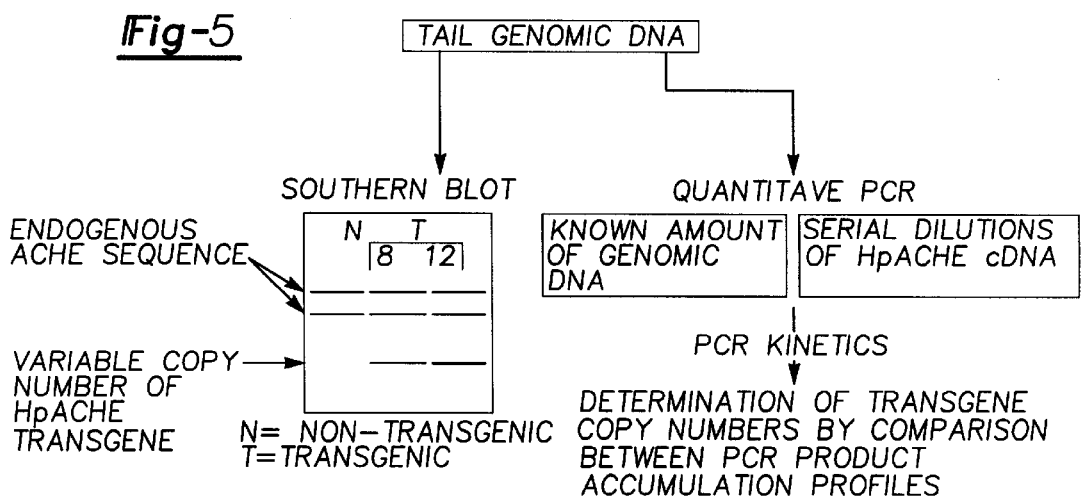

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
(A) LENGTH: 2256 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "ACHE gene comprising exons 2, 3, 4 and 6"

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO:1:

```
CCTCTCTCCC CTCATCTTTG CCAACCTGCC CCACCTCCTC TGCAGCTGAG CGATAACCCT      60
TGGGCCGACA GTGCCCTAAT CTCCTCCCTC CTGGCTTCTC GACCGACCCT TCACCCTTTC     120
CCTTTCTTTC TCCCAGCAGA CGCCGCCTGC CCTGCAGCCA TGAGGCCCCC GCAGTGTCTG     180
CTGCACACGC CTTCCCTGGC TTCCCCACTC CTTCTCCTCC TCCTCTGGCT CCTGGGTGGA     240
GGAGTGGGGG CTGAGGGCCG GGAGGATGCA GAGCTGCTGG TGACGGTGCG TGGGGGCCGG     300
CTGCGGGGCA TTCGCCTGAA GACCCCCGGG GGCCCTGTCT CTGCTTTCCT GGGCATCCCC     360
TTTGCGGAGC CACCCATGGG ACCCCGTCGC TTTCTGCCAC CGGAGCCCAA GCAGCCTTGG     420
TCAGGGGTGG TAGACGCTAC AACCTTCCAG AGTGTCTGCT ACCAATATGT GGACACCCTA     480
TACCCAGGTT TTGAGGGCAC CGAGATGTGG AACCCCAACC GTGAGCTGAG CGAGGACTGC     540
CTGTACCTCA ACGTGTGGAC ACCATACCCC CGGCCTACAT CCCCCACCCC TGTCCTCGTC     600
TGGATCTATG GGGGTGGCTT CTACAGTGGG GCCTCCTCCT TGGACGTGTA CGATGGCCGC     660
TTCTTGGTAC AGGCCGAGAG GACTGTGCTG GTGTCCATGA ACTACCGGGT GGGAGCCTTT     720
GGCTTCCTGG CCCTGCCGGG GAGCCGAGAG GCCCCGGGCA ATGTGGGTCT CCTGGATCAG     780
AGGCTGGCCC TGCAGTGGGT GCAGGAGAAC GTGGCAGCCT TCGGGGGTGA CCCGACATCA     840
GTGACGCTGT TTGGGGAGAG CGCGGGAGCC GCCTCGGTGG GCATGCACCT GCTGTCCCCG     900
CCCAGCCGGG GCCTGTTCCA CAGGGCCGTG CTGCAGAGCG GTGCCCCCAA TGGACCCTGG     960
GCCACGGTGG GCATGGGAGA GGCCCGTCGC AGGGCCACGC AGCTGGCCCA CCTTGTGGGC    1020
TGTCCTCCAG GCGGCACTGG TGGGAATGAC ACAGAGCTGG TAGCCTGCCT TCGGACACGA    1080
CCAGCGCAGG TCCTGGTGAA CCACGAATGG CACGTGCTGC CTCAAGAAAG CGTCTTCCGG    1140
TTCTCCTTCG TGCCTGTGGT AGATGGAGAC TTCCTCAGTG ACACCCCAGA GGCCCTCATC    1200
AACGCGGGAG ACTTCCACGG CCTGCAGGTG CTGGTGGGTG TGGTGAAGGA TGAGGGCTCG    1260
TATTTTCTGG TTTACGGGGC CCCAGGCTTC AGCAAAGACA ACGAGTCTCT CATCAGCCGG    1320
GCCGAGTTCC TGGCCGGGGT GCGGGTCGGG GTTCCCCAGG TAAGTGACCT GGCAGCCGAG    1380
GCTGTGGTCC TGCATTACAC AGACTGGCTG CATCCCGAGG ACCCGGCACG CCTGAGGGAG    1440
GCCCTGAGCG ATGTGGTGGG CGACCACAAT GTCGTGTGCC CCGTGGCCCA GCTGGCTGGG    1500
CGACTGGCTG CCCAGGGTGC CCGGGTCTAC GCCTACGTCT TTGAACACCG TGCTTCCACG    1560
```

```
CTCTCCTGGC CCCTGTGGAT GGGGGTGCCC CACGGCTACG AGATCGAGTT CATCTTTGGG      1620

ATCCCCCTGG ACCCCTCTCG AAACTACACG GCAGAGGAGA AAATCTTCGC CCAGCGACTG      1680

ATGCGATACT GGGCCAACTT TGCCCGCACA GGGGATCCCA ATGAGCCCCG AGACCCCAAG      1740

GCCCCACAAT GGCCCCCGTA CACGGCGGGG GCTCAGCAGT ACGTTAGTCT GGACCTGCGG      1800

CCGCTGGAGG TGCGGCGGGG GCTGCGCGCC CAGGCCTGCG CCTTCTGGAA CCGCTTCCTC      1860

CCCAAATTGC TCAGCGCCAC CGACACGCTC GACGAGGCGG AGCGCCAGTG GAAGGCCGAG      1920

TTCCACCGCT GGAGCTCCTA CATGGTGCAC TGGAAGAACC AGTTCGACCA CTACAGCAAG      1980

CAGGATCGCT GCTCAGACCT GTGACCCCGG CGGGACCCCC ATGTCCTCCG CTCCGCCCGG      2040

CCCCCTAGCT GTATATACTA TTTATTTCAG GGCTGGGCTA TAACAGAC GAGCCCCAGA       2100

CTCTGCCCAT CCCCACCCCA CCCCGACGTC CCCCGGGGCT CCCGGTCCTC TGGCATGTCT      2160

TCAGGCTGAG CTCCTCCCCG CGTGCCTTCG CCCTCTGGCT GCAAATAAAC TGTTACAGGC      2220

CAAAAAAAAA AAAAAAAAAA AAAAAAAAAA AAAAA                                 2256
```

(2) INFORMATION FOR SEQ ID NO:2:

(i) SEQUENCE CHARACTERISTICS:
        (A) LENGTH: 614 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:2:

```
Met Arg Pro Pro Gln Cys Leu Leu His Thr Pro Ser Leu Ala Ser Pro
1               5                  10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
        195                 200                 205
```

```
Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240

Gly Met His Leu Leu Ser Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
        275                 280                 285

Pro Pro Gly Gly Thr Gly Gly Asn Asp Thr Glu Leu Val Ala Cys Leu
    290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
            340                 345                 350

His Gly Leu Gln Val Leu Val Gly Val Val Lys Asp Glu Gly Ser Tyr
        355                 360                 365

Phe Leu Val Tyr Gly Ala Pro Gly Phe Ser Lys Asp Asn Glu Ser Leu
    370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
            420                 425                 430

Val Gly Asp His Asn Val Val Cys Pro Val Ala Gln Leu Ala Gly Arg
        435                 440                 445

Leu Ala Ala Gln Gly Ala Arg Val Tyr Ala Tyr Val Phe Glu His Arg
    450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
    515                 520                 525

Pro Gln Trp Pro Pro Tyr Thr Ala Gly Ala Gln Gln Tyr Val Ser Leu
530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
            580                 585                 590

Ser Tyr Met Val His Trp Lys Asn Gln Phe Asp His Tyr Ser Lys Gln
        595                 600                 605

Asp Arg Cys Ser Asp Leu
    610

(2) INFORMATION FOR SEQ ID NO:3:
```

(i) SEQUENCE CHARACTERISTICS:
  (A) LENGTH: 3096 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "Alternatively spliced AChE
      comprising exons 2, 3, 4 and 5 as well as the translated
      portion of Intron 4 (readthrough)"

(vi) ORIGINAL SOURCE:
  (A) ORGANISM: Homo sapiens (ix) FEATURE:
  (A) NAME/KEY: CDS
  (B) LOCATION: 160..1959

(xi) SEQUENCE DESCRIPTION: SEQ ID NO:3:

```
CCTCTCTCCC CTCATCTTTG CCAACCTGCC CCACCTCCTC TGCAGCTGAG CGATAACCCT        60

TGGGCCGACA GTGCCCTAAT CTCCTCCCTC CTGGCTTCTC GACCGACCCT TCACCCTTTC       120

CCTTTCTTTC TCCCAGCAGA CGCCGCCTGC CCTGCAGCC ATG AGG CCC CCG CAG          174
                                            Met Arg Pro Pro Gln
                                             1               5

TGT CTG CTG CAC ACG CCT TCC CTG GCT TCC CCA CTC CTT CTC CTC CTC         222
Cys Leu Leu His Thr Pro Ser Leu Ala Ser Pro Leu Leu Leu Leu Leu
              10                  15                  20

CTC TGG CTC CTG GGT GGA GGA GTG GGG GCT GAG GGC CGG GAG GAT GCA         270
Leu Trp Leu Leu Gly Gly Gly Val Gly Ala Glu Gly Arg Glu Asp Ala
         25                  30                  35

GAG CTG CTG GTG ACG GTG CGT GGG GGC CGG CTG CGG GGC ATT CGC CTG         318
Glu Leu Leu Val Thr Val Arg Gly Gly Arg Leu Arg Gly Ile Arg Leu
     40                  45                  50

AAG ACC CCC GGG GGC CCT GTC TCT GCT TTC CTG GGC ATC CCC TTT GCG         366
Lys Thr Pro Gly Gly Pro Val Ser Ala Phe Leu Gly Ile Pro Phe Ala
 55                  60                  65

GAG CCA CCC ATG GGA CCC GTT CGC TTT CTG CCA CCG GAG CCC AAG CAG         414
Glu Pro Pro Met Gly Pro Arg Arg Phe Leu Pro Pro Glu Pro Lys Gln
 70                  75                  80                  85

CCT TGG TCA GGG GTG GTA GAC GCT ACA ACC TTC CAG AGT GTC TGC TAC         462
Pro Trp Ser Gly Val Val Asp Ala Thr Thr Phe Gln Ser Val Cys Tyr
                 90                  95                 100

CAA TAT GTG GAC ACC CTA TAC CCA GGT TTT GAG GGC ACC GAG ATG TGG         510
Gln Tyr Val Asp Thr Leu Tyr Pro Gly Phe Glu Gly Thr Glu Met Trp
            105                 110                 115

AAC CCC AAC CGT GAG CTG AGC GAG GAC TGC CTG TAC CTC AAC GTG TGG         558
Asn Pro Asn Arg Glu Leu Ser Glu Asp Cys Leu Tyr Leu Asn Val Trp
        120                 125                 130

ACA CCA TAC CCC CGG CCT ACA TCC CCC ACC CCT GTC CTC GTC TGG ATC         606
Thr Pro Tyr Pro Arg Pro Thr Ser Pro Thr Pro Val Leu Val Trp Ile
    135                 140                 145

TAT GGG GGT GGC TTC TAC AGT GGG GCC TCC TCC TTG GAC GTG TAC GAT         654
Tyr Gly Gly Gly Phe Tyr Ser Gly Ala Ser Ser Leu Asp Val Tyr Asp
150                 155                 160                 165

GGC CGC TTC TTG GTA CAG GCC GAG AGG ACT GTG CTG GTG TCC ATG AAC         702
Gly Arg Phe Leu Val Gln Ala Glu Arg Thr Val Leu Val Ser Met Asn
                170                 175                 180

TAC CGG GTG GGA GCC TTT GGC TTC CTG GCC CTG CCG GGG AGC CGA GAG         750
Tyr Arg Val Gly Ala Phe Gly Phe Leu Ala Leu Pro Gly Ser Arg Glu
            185                 190                 195

GCC CCG GGC AAT GTG GGT CTC CTG GAT CAG AGG CTG GCC CTG CAG TGG         798
Ala Pro Gly Asn Val Gly Leu Leu Asp Gln Arg Leu Ala Leu Gln Trp
        200                 205                 210
```

```
GTG CAG GAG AAC GTG GCA GCC TTC GGG GGT GAC CCG ACA TCA GTG ACG        846
Val Gln Glu Asn Val Ala Ala Phe Gly Gly Asp Pro Thr Ser Val Thr
215                 220                 225

CTG TTT GGG GAG AGC GCG GGA GCC GCC TCG GTG GGC ATG CAC CTG CTG        894
Leu Phe Gly Glu Ser Ala Gly Ala Ala Ser Val Gly Met His Leu Leu
230                 235                 240                 245

TCC CCG CCC AGC CGG GGC CTG TTC CAC AGG GCC GTG CTG CAG AGC GGT        942
Ser Pro Pro Ser Arg Gly Leu Phe His Arg Ala Val Leu Gln Ser Gly
                250                 255                 260

GCC CCC AAT GGA CCC TGG GCC ACG GTG GGC ATG GGA GAG GCC CGT CGC        990
Ala Pro Asn Gly Pro Trp Ala Thr Val Gly Met Gly Glu Ala Arg Arg
            265                 270                 275

AGG GCC ACG CAG CTG GCC CAC CTT GTG GGC TGT CCT CCA GGC GGC ACT       1038
Arg Ala Thr Gln Leu Ala His Leu Val Gly Cys Pro Pro Gly Gly Thr
        280                 285                 290

GGT GGG AAT GAC ACA GAG CTG GTA GCC TGC CTT CGG ACA CGA CCA GCG       1086
Gly Gly Asn Asp Thr Glu Leu Val Ala Cys Leu Arg Thr Arg Pro Ala
295                 300                 305

CAG GTC CTG GTG AAC CAC GAA TGG CAC GTG CTG CCT CAA GAA AGC GTC       1134
Gln Val Leu Val Asn His Glu Trp His Val Leu Pro Gln Glu Ser Val
310                 315                 320                 325

TTC CGG TTC TCC TTC GTG CCT GTG GTA GAT GGA GAC TTC CTC AGT GAC       1182
Phe Arg Phe Ser Phe Val Pro Val Val Asp Gly Asp Phe Leu Ser Asp
                330                 335                 340

ACC CCA GAG GCC CTC ATC AAC GCG GGA GAC TTC CAC GGC CTG CAG GTG       1230
Thr Pro Glu Ala Leu Ile Asn Ala Gly Asp Phe His Gly Leu Gln Val
            345                 350                 355

CTG GTG GGT GTG GTG AAG GAT GAG GGC TCG TAT TTT CTG GTT TAC GGG       1278
Leu Val Gly Val Val Lys Asp Glu Gly Ser Tyr Phe Leu Val Tyr Gly
        360                 365                 370

GCC CCA GGC TTC AGC AAA GAC AAC GAG TCT CTC ATC AGC CGG GCC GAG       1326
Ala Pro Gly Phe Ser Lys Asp Asn Glu Ser Leu Ile Ser Arg Ala Glu
375                 380                 385

TTC CTG GCC GGG GTG CGG GTC GGG GTT CCC CAG GTA AGT GAC CTG GCA       1374
Phe Leu Ala Gly Val Arg Val Gly Val Pro Gln Val Ser Asp Leu Ala
390                 395                 400                 405

GCC GAG GCT GTG GTC CTG CAT TAC ACA GAC TGG CTG CAT CCC GAG GAC       1422
Ala Glu Ala Val Val Leu His Tyr Thr Asp Trp Leu His Pro Glu Asp
                410                 415                 420

CCG GCA CGC CTG AGG GAG GCC CTG AGC GAT GTG GTG GGC GAC CAC AAT       1470
Pro Ala Arg Leu Arg Glu Ala Leu Ser Asp Val Val Gly Asp His Asn
            425                 430                 435

GTC GTG TGC CCC GTG GCC CAG CTG GCT GGG CGA CTG GCT GCC CAG GGT       1518
Val Val Cys Pro Val Ala Gln Leu Ala Gly Arg Leu Ala Ala Gln Gly
        440                 445                 450

GCC CGG GTC TAC GCC TAC GTC TTT GAA CAC CGT GCT TCC ACG CTC TCC       1566
Ala Arg Val Tyr Ala Tyr Val Phe Glu His Arg Ala Ser Thr Leu Ser
455                 460                 465

TGG CCC CTG TGG ATG GGG GTG CCC CAC GGC TAC GAG ATC GAG TTC ATC       1614
Trp Pro Leu Trp Met Gly Val Pro His Gly Tyr Glu Ile Glu Phe Ile
470                 475                 480                 485

TTT GGG ATC CCC CTG GAC CCC TCT CGA AAC TAC ACG GCA GAG GAG AAA       1662
Phe Gly Ile Pro Leu Asp Pro Ser Arg Asn Tyr Thr Ala Glu Glu Lys
                490                 495                 500

ATC TTC GCC CAG CGA CTG ATG CGA TAC TGG GCC AAC TTT GCC CGC ACA       1710
Ile Phe Ala Gln Arg Leu Met Arg Tyr Trp Ala Asn Phe Ala Arg Thr
            505                 510                 515

GGG GAT CCC AAT GAG CCC CGA GAC CCC AAG GCC CCA CAA TGG CCC CCG       1758
Gly Asp Pro Asn Glu Pro Arg Asp Pro Lys Ala Pro Gln Trp Pro Pro
        520                 525                 530
```

```
TAC ACG GCG GGG GCT CAG CAG TAC GTT AGT CTG GAC CTG CGG CCG CTG      1806
Tyr Thr Ala Gly Ala Gln Gln Tyr Val Ser Leu Asp Leu Arg Pro Leu
    535                 540                 545

GAG GTG CGG CGG GGG CTG CGC GCC CAG GCC TGC GCC TTC TGG AAC CGC      1854
Glu Val Arg Arg Gly Leu Arg Ala Gln Ala Cys Ala Phe Trp Asn Arg
550                 555                 560                 565

TTC CTC CCC AAA TTG CTC AGC GCC ACC GGT ATG CAG GGG CCA GCG GGC      1902
Phe Leu Pro Lys Leu Leu Ser Ala Thr Gly Met Gln Gly Pro Ala Gly
                570                 575                 580

AGC GGC TGG GAG GAG GGG AGT GGG AGC CCG CCA GGT GTA ACC CCT CTC      1950
Ser Gly Trp Glu Glu Gly Ser Gly Ser Pro Pro Gly Val Thr Pro Leu
            585                 590                 595

TTC TCC CCC TAGCCTCGGA GGCTCCCAGC ACCTGCCCAG GCTTCACCCA              1999
Phe Ser Pro
        600

TGGGGAGGCT GCTCCGAGGC CCGGCCTCCC CCTGCCCCTC CTCCTCCTCC ACCAGCTTCT    2059

CCTCCTCTTC CTCTCCCACC TCCGGCGGCT GTGAACACGG CCTCTTCCCC TACGGCCTAC    2119

AGGGGCCCCT CCTCTAATGA GTGGTAGGAC CTGTGGGGAA GGGCCCCACT CAGGGATCTC    2179

AGACCTAGTG CTCCCTTCCT CCTCAAACCG AGAGACTCAC ACTGGACAGG GCAGGAGGAG    2239

GGGCCGTGCC TCCCACCCTT CTCAGGGACC CCCACGCCTT TGTTGTTTGA ATGGAAATGG    2299

AAAAGCCAGT ATTCTTTTAT AAAATTATCT TTTGGAACCT GAGCCTGACA TTGGGGGAAG    2359

TGGAGGCCCG GAAACGGGGT AGCACCCCCA TTGGGGCTAT AACGGTCAAC CATTTCTGTC    2419

TCTTCTTTTT CCCCCAACCT CCCCCTCCTG TCCCCTCTGT TCCCGTCTTC CGGTCATTCT    2479

TTTCTCCTCC TCTCTCCTTC CTGCTGTCCT TCTCGGCCCC GCCTCTGCCC TCATCCTCCC    2539

TCTCGTCTTT CGCACATTCT CCTGATCCTC TTGCCACCGT CCCACGTGGT CGCCTGCATT    2599

TCTCCGTGCG TCCTCCCTGC ACTCATACCC CCCCTTCAAC CCGCCCAAAT GTCCGATCCC    2659

CGACCTTCCT CGTGCCGTCC TCCCCTCCCG CCTCGCTGGG CGCCCTGGCC GCAGACACGC    2719

TCGACACGCT CGACGAGGCG GAGCGCCAGT GGAAGGCCGA GTTCCACCGC TGGAGCTCCT    2779

ACATGGTGCA CTGGAAGAAC CAGTTCGACC ACTACAGCAA GCAGGATCGC TGCTCAGACC    2839

TGTGACCCCG GCGGGACCCC CATGTCCTCC GCTCCGCCCG GCCCCCTAGC TGTATATACT    2899

ATTTATTTCA GGGCTGGGCT ATAACACAGA CGAGCCCCAG ACTCTGCCCA TCCCCACCCC    2959

ACCCCGACGT CCCCCGGGGC TCCCGGTCCT CTGGCATGTC TTCAGGCTGA GCTCCTCCCC    3019

GCGTGCCTTC GCCCTCTGGC TGCAAATAAA CTGTTACAGG CCAAAAAAAA AAAAAAAAA    3079

AAAAAAAAAA AAAAAAA                                                   3096

(2) INFORMATION FOR SEQ ID NO:4:

(i) SEQUENCE CHARACTERISTICS:
        (A) LENGTH: 600 amino acids
        (B) TYPE: amino acid
        (D) TOPOLOGY: linear (ii) MOLECULE TYPE: protein (xi) SEQUENCE DESCRIPTION: SEQ ID NO:4:

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
        35                  40                  45
```

```
Arg Gly Ile Arg Leu Lys Thr Pro Gly Pro Val Ser Ala Phe Leu
 50                  55                  60

Gly Ile Pro Phe Ala Glu Pro Pro Met Gly Pro Arg Arg Phe Leu Pro
 65                  70                  75                  80

Pro Glu Pro Lys Gln Pro Trp Ser Gly Val Val Asp Ala Thr Thr Phe
                 85                  90                  95

Gln Ser Val Cys Tyr Gln Tyr Val Asp Thr Leu Tyr Pro Gly Phe Glu
                100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
130                 135                 140

Val Leu Val Trp Ile Tyr Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
                180                 185                 190

Pro Gly Ser Arg Glu Ala Pro Gly Asn Val Gly Leu Leu Asp Gln Arg
            195                 200                 205

Leu Ala Leu Gln Trp Val Gln Glu Asn Val Ala Ala Phe Gly Gly Asp
210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
            275                 280                 285

Pro Pro Gly Gly Thr Gly Gly Asn Asp Thr Glu Leu Val Ala Cys Leu
290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
                340                 345                 350

His Gly Leu Gln Val Leu Val Gly Val Val Lys Asp Glu Gly Ser Tyr
            355                 360                 365

Phe Leu Val Tyr Gly Ala Pro Gly Phe Ser Lys Asp Asn Glu Ser Leu
            370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
                420                 425                 430

Val Gly Asp His Asn Val Val Cys Pro Val Ala Gln Leu Ala Gly Arg
            435                 440                 445

Leu Ala Ala Gln Gly Ala Arg Val Tyr Ala Tyr Val Phe Glu His Arg
450                 455                 460

Ala Ser Thr Leu Ser Trp Pro Leu Trp Met Gly Val Pro His Gly Tyr
465                 470                 475                 480
```

```
Glu Ile Glu Phe Ile Phe Gly Ile Pro Leu Asp Pro Ser Arg Asn Tyr
            485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
            515                 520                 525

Pro Gln Trp Pro Pro Tyr Thr Ala Gly Ala Gln Gln Tyr Val Ser Leu
        530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Gly Met
            565                 570                 575

Gln Gly Pro Ala Gly Ser Gly Trp Glu Gly Ser Gly Ser Pro Pro
            580                 585                 590

Gly Val Thr Pro Leu Phe Ser Pro
            595                 600
```

(2) INFORMATION FOR SEQ ID NO:5:

(i) SEQUENCE CHARACTERISTICS:
        (A) LENGTH: 3016 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Alternatively spliced AChE
            comprising exons 2, 3, 4, 5 and 6"

(vi) ORIGINAL SOURCE:
        (A) ORGANISM: Homo sapiens (ix) FEATURE:
        (A) NAME/KEY: CDS
        (B) LOCATION: 160..2010

(xi) SEQUENCE DESCRIPTION: SEQ ID NO:5:

```
CCTCTCTCCC CTCATCTTTG CCAACCTGCC CCACCTCCTC TGCAGCTGAG CGATAACCCT      60

TGGGCCGACA GTGCCCTAAT CTCCTCCCTC CTGGCTTCTC GACCGACCCT TCACCCTTTC     120

CCTTTCTTTC TCCCAGCAGA CGCCGCCTGC CCTGCAGCC ATG AGG CCC CCG CAG       174
                                            Met Arg Pro Pro Gln
                                              1               5

TGT CTG CTG CAC ACG CCT TCC CTG GCT TCC CCA CTC CTT CTC CTC CTC      222
Cys Leu Leu His Thr Pro Ser Leu Ala Ser Pro Leu Leu Leu Leu Leu
                10                  15                  20

CTC TGG CTC CTG GGT GGA GGA GTG GGG GCT GAG GGC CGG GAG GAT GCA      270
Leu Trp Leu Leu Gly Gly Gly Val Gly Ala Glu Gly Arg Glu Asp Ala
            25                  30                  35

GAG CTG CTG GTG ACG GTG CGT GGG GGC CGG CTG CGG GGC ATT CGC CTG      318
Glu Leu Leu Val Thr Val Arg Gly Gly Arg Leu Arg Gly Ile Arg Leu
        40                  45                  50

AAG ACC CCC GGG GGC CCT GTC TCT GCT TTC CTG GGC ATC CCC TTT GCG      366
Lys Thr Pro Gly Gly Pro Val Ser Ala Phe Leu Gly Ile Pro Phe Ala
    55                  60                  65

GAG CCA CCC ATG GGA CCC CGT CGC TTT CTG CCA CCG GAG CCC AAG CAG      414
Glu Pro Pro Met Gly Pro Arg Arg Phe Leu Pro Pro Glu Pro Lys Gln
70                  75                  80                  85

CCT TGG TCA GGG GTG GTA GAC GCT ACA ACC TTC CAG AGT GTC TGC TAC      462
Pro Trp Ser Gly Val Val Asp Ala Thr Thr Phe Gln Ser Val Cys Tyr
                90                  95                 100

CAA TAT GTG GAC ACC CTA TAC CCA GGT TTT GAG GGC ACC GAG ATG TGG      510
```

-continued

| | | | | | | | | | | | | | |
|---|---|---|---|---|---|---|---|---|---|---|---|---|---|
| Gln | Tyr | Val | Asp | Thr | Leu | Tyr | Pro | Gly | Phe | Glu | Gly | Thr | Glu | Met | Trp |
| | | | 105 | | | | 110 | | | | 115 | | |

```
AAC CCC AAC CGT GAG CTG AGC GAG GAC TGC CTG TAC CTC AAC GTG TGG            558
Asn Pro Asn Arg Glu Leu Ser Glu Asp Cys Leu Tyr Leu Asn Val Trp
        120                 125                 130

ACA CCA TAC CCC CGG CCT ACA TCC CCC ACC CCT GTC CTC GTC TGG ATC            606
Thr Pro Tyr Pro Arg Pro Thr Ser Pro Thr Pro Val Leu Val Trp Ile
        135                 140                 145

TAT GGG GGT GGC TTC TAC AGT GGG GCC TCC TCC TTG GAC GTG TAC GAT            654
Tyr Gly Gly Gly Phe Tyr Ser Gly Ala Ser Ser Leu Asp Val Tyr Asp
150                 155                 160                 165

GGC CGC TTC TTG GTA CAG GCC GAG AGG ACT GTG CTG GTG TCC ATG AAC            702
Gly Arg Phe Leu Val Gln Ala Glu Arg Thr Val Leu Val Ser Met Asn
                170                 175                 180

TAC CGG GTG GGA GCC TTT GGC TTC CTG GCC CTG CCG GGG AGC CGA GAG            750
Tyr Arg Val Gly Ala Phe Gly Phe Leu Ala Leu Pro Gly Ser Arg Glu
                185                 190                 195

GCC CCG GGC AAT GTG GGT CTC CTG GAT CAG AGG CTG GCC CTG CAG TGG            798
Ala Pro Gly Asn Val Gly Leu Leu Asp Gln Arg Leu Ala Leu Gln Trp
                200                 205                 210

GTG CAG GAG AAC GTG GCA GCC TTC GGG GGT GAC CCG ACA TCA GTG ACG            846
Val Gln Glu Asn Val Ala Ala Phe Gly Gly Asp Pro Thr Ser Val Thr
        215                 220                 225

CTG TTT GGG GAG AGC GCG GGA GCC GCC TCG GTG GGC ATG CAC CTG CTG            894
Leu Phe Gly Glu Ser Ala Gly Ala Ala Ser Val Gly Met His Leu Leu
230                 235                 240                 245

TCC CCG CCC AGC CGG GGC CTG TTC CAC AGG GCC GTG CTG CAG AGC GGT            942
Ser Pro Pro Ser Arg Gly Leu Phe His Arg Ala Val Leu Gln Ser Gly
                250                 255                 260

GCC CCC AAT GGA CCC TGG GCC ACG GTG GGC ATG GGA GAG GCC CGT CGC            990
Ala Pro Asn Gly Pro Trp Ala Thr Val Gly Met Gly Glu Ala Arg Arg
                265                 270                 275

AGG GCC ACG CAG CTG GCC CAC CTT GTG GGC TGT CCT CCA GGC GGC ACT           1038
Arg Ala Thr Gln Leu Ala His Leu Val Gly Cys Pro Pro Gly Gly Thr
        280                 285                 290

GGT GGG AAT GAC ACA GAG CTG GTA GCC TGC CTT CGG ACA CGA CCA GCG           1086
Gly Gly Asn Asp Thr Glu Leu Val Ala Cys Leu Arg Thr Arg Pro Ala
        295                 300                 305

CAG GTC CTG GTG AAC CAC GAA TGG CAC GTG CTG CCT CAA GAA AGC GTC           1134
Gln Val Leu Val Asn His Glu Trp His Val Leu Pro Gln Glu Ser Val
310                 315                 320                 325

TTC CGG TTC TCC TTC GTG CCT GTG GTA GAT GGA GAC TTC CTC AGT GAC           1182
Phe Arg Phe Ser Phe Val Pro Val Val Asp Gly Asp Phe Leu Ser Asp
                330                 335                 340

ACC CCA GAG GCC CTC ATC AAC GCG GGA GAC TTC CAC GGC CTG CAG GTG           1230
Thr Pro Glu Ala Leu Ile Asn Ala Gly Asp Phe His Gly Leu Gln Val
        345                 350                 355

CTG GTG GGT GTG GTG AAG GAT GAG GGC TCG TAT TTT CTG GTT TAC GGG           1278
Leu Val Gly Val Val Lys Asp Glu Gly Ser Tyr Phe Leu Val Tyr Gly
        360                 365                 370

GCC CCA GGC TTC AGC AAA GAC AAC GAG TCT CTC ATC AGC CGG GCC GAG           1326
Ala Pro Gly Phe Ser Lys Asp Asn Glu Ser Leu Ile Ser Arg Ala Glu
        375                 380                 385

TTC CTG GCC GGG GTG CGG GTC GGG GTT CCC CAG GTA AGT GAC CTG GCA           1374
Phe Leu Ala Gly Val Arg Val Gly Val Pro Gln Val Ser Asp Leu Ala
390                 395                 400                 405

GCC GAG GCT GTG GTC CTG CAT TAC ACA GAC TGG CTG CAT CCC GAG GAC           1422
Ala Glu Ala Val Val Leu His Tyr Thr Asp Trp Leu His Pro Glu Asp
                410                 415                 420

CCG GCA CGC CTG AGG GAG GCC CTG AGC GAT GTG GTG GGC GAC CAC AAT           1470
```

```
Pro Ala Arg Leu Arg Glu Ala Leu Ser Asp Val Val Gly Asp His Asn
        425                 430                 435

GTC GTG TGC CCC GTG GCC CAG CTG GCT GGG CGA CTG GCT GCC CAG GGT          1518
Val Val Cys Pro Val Ala Gln Leu Ala Gly Arg Leu Ala Ala Gln Gly
            440                 445                 450

GCC CGG GTC TAC GCC TAC GTC TTT GAA CAC CGT GCT TCC ACG CTC TCC          1566
Ala Arg Val Tyr Ala Tyr Val Phe Glu His Arg Ala Ser Thr Leu Ser
        455                 460                 465

TGG CCC CTG TGG ATG GGG GTG CCC CAC GGC TAC GAG ATC GAG TTC ATC          1614
Trp Pro Leu Trp Met Gly Val Pro His Gly Tyr Glu Ile Glu Phe Ile
470                 475                 480                 485

TTT GGG ATC CCC CTG GAC CCC TCT CGA AAC TAC ACG GCA GAG GAG AAA          1662
Phe Gly Ile Pro Leu Asp Pro Ser Arg Asn Tyr Thr Ala Glu Glu Lys
                490                 495                 500

ATC TTC GCC CAG CGA CTG ATG CGA TAC TGG GCC AAC TTT GCC CGC ACA          1710
Ile Phe Ala Gln Arg Leu Met Arg Tyr Trp Ala Asn Phe Ala Arg Thr
            505                 510                 515

GGG GAT CCC AAT GAG CCC CGA GAC CCC AAG GCC CCA CAA TGG CCC CCG          1758
Gly Asp Pro Asn Glu Pro Arg Asp Pro Lys Ala Pro Gln Trp Pro Pro
        520                 525                 530

TAC ACG GCG GGG GCT CAG CAG TAC GTT AGT CTG GAC CTG CGG CCG CTG          1806
Tyr Thr Ala Gly Ala Gln Gln Tyr Val Ser Leu Asp Leu Arg Pro Leu
535                 540                 545

GAG GTG CGG CGG GGG CTG CGC GCC CAG GCC TGC GCC TTC TGG AAC CGC          1854
Glu Val Arg Arg Gly Leu Arg Ala Gln Ala Cys Ala Phe Trp Asn Arg
550                 555                 560                 565

TTC CTC CCC AAA TTG CTC AGC GCC ACC GCC TCG GAG GCT CCC AGC ACC          1902
Phe Leu Pro Lys Leu Leu Ser Ala Thr Ala Ser Glu Ala Pro Ser Thr
                570                 575                 580

TGC CCA GGC TTC ACC CAT GGG GAG GCT GCT CCG AGG CCC GGC CTC CCC          1950
Cys Pro Gly Phe Thr His Gly Glu Ala Ala Pro Arg Pro Gly Leu Pro
            585                 590                 595

CTG CCC CTC CTC CTC CAC CAG CTT CTC CTC CTC TTC CTC TCC CAC              1998
Leu Pro Leu Leu Leu His Gln Leu Leu Leu Leu Phe Leu Ser His
        600                 605                 610

CTC CGG CGG CTG TGAACACGGC TCTTCCCCT ACGGCCTACA GGGGCCCCTC               2050
Leu Arg Arg Leu
        615

CTCTAATGAG TGGTAGGACC TGTGGGAAG GGCCCCACTC AGGGATCTCA GACCTAGTGC         2110

TCCCTTCCTC CTCAAACCGA GAGACTCACA CTGGACAGGG CAGGAGGAGG GGCCGTGCCT        2170

CCCACCCTTC TCAGGGACCC CCACGCCTTT GTTGTTTGAA TGGAAATGGA AAAGCCAGTA        2230

TTCTTTTATA AAATTATCTT TTGGAACCTG AGCCTGACAT TGGGGGAAGT GGAGGCCCGG        2290

AAACGGGGTA GCACCCCCAT TGGGGCTATA ACGGTCAACC ATTTCTGTCT CTTCTTTTTC        2350

CCCCAACCTC CCCCTCCTGT CCCCTCTGTT CCCGTCTTCC GGTCATTCTT TTCTCCTCCT        2410

CTCTCCTTCC TGCTGTCCTT CTCGGCCCCG CCTCTGCCCT CATCCTCCCT CTCGTCTTTC        2470

GCACATTCTC CTGATCCTCT TGCCACCGTC CCACGTGGTC GCCTGCATTT CTCCGTGCGT        2530

CCTCCCTGCA CTCATACCCC CCCTTCAACC CGCCCAAATG TCCGATCCCC GACCTTCCTC        2590

GTGCCGTCCT CCCCTCCCGC CTCGCTGGGC GCCCTGGCCG CAGACACGCT CGACACGCTC        2650

GACGAGGCGG AGCGCCAGTG GAAGGCCGAG TTCACCGCT GGAGCTCCTA CATGGTGCAC         2710

TGGAAGAACC AGTTCGACCA CTACAGCAAG CAGGATCGCT GCTCAGACCT GTGACCCCGG        2770

CGGGACCCCC ATGTCCTCCG CTCCGCCCGG CCCCTAGCT GTATATACTA TTTATTTCAG         2830

GGCTGGGCTA TAACACAGAC GAGCCCCAGA CTCTGCCCAT CCCCACCCCA CCCCGACGTC        2890

CCCCGGGGCT CCCGGTCCTC TGGCATGTCT TCAGGCTGAG CTCCTCCCCG CGTGCCTTCG        2950
```

```
CCCTCTGGCT GCAAATAAAC TGTTACAGGC CAAAAAAAAA AAAAAAAAAA AAAAAAAAAA        3010

AAAAAA                                                                  3016
```

(2) INFORMATION FOR SEQ ID NO:6:

(i) SEQUENCE CHARACTERISTICS:
        (A) LENGTH: 617 amino acids
        (B) TYPE: amino acid
        (D) TOPOLOGY: linear (ii) MOLECULE TYPE: protein (xi) SEQUENCE DESCRIPTION: SEQ ID NO:6:

```
Met Arg Pro Pro Gln Cys Leu Leu His Thr Pro Ser Leu Ala Ser Pro
 1               5                  10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
        195                 200                 205

Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
        275                 280                 285

Pro Pro Gly Gly Thr Gly Gly Asn Asp Thr Glu Leu Val Ala Cys Leu
    290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335
```

```
Asp Phe Leu Ser Asp Thr Pro Glu Ala Leu Ile Asn Ala Gly Asp Phe
            340                 345                 350

His Gly Leu Gln Val Leu Val Gly Val Val Lys Asp Glu Gly Ser Tyr
            355                 360                 365

Phe Leu Val Tyr Gly Ala Pro Gly Phe Ser Lys Asp Asn Glu Ser Leu
            370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
            420                 425                 430

Val Gly Asp His Asn Val Val Cys Pro Val Ala Gln Leu Ala Gly Arg
            435                 440                 445

Leu Ala Ala Gln Gly Ala Arg Val Tyr Ala Tyr Val Phe Glu His Arg
            450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
            485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
            515                 520                 525

Pro Gln Trp Pro Pro Tyr Thr Ala Gly Ala Gln Gln Tyr Val Ser Leu
            530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Ala Ser
            565                 570                 575

Glu Ala Pro Ser Thr Cys Pro Gly Phe Thr His Gly Glu Ala Ala Pro
            580                 585                 590

Arg Pro Gly Leu Pro Leu Pro Leu Leu Leu His Gln Leu Leu Leu
            595                 600                 605

Leu Phe Leu Ser His Leu Arg Arg Leu
            610                 615

(2) INFORMATION FOR SEQ ID NO:7:

(i) SEQUENCE CHARACTERISTICS:
        (A) LENGTH: 35060 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Cosmid including ACHE
            promotor, ACHE gene and ARS gene"

(iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: 7q22

(ix) FEATURE:
        (A) NAME/KEY: promoter
        (B) LOCATION: 4089..22464
```

```
       (D) OTHER INFORMATION: /function= "ACHE Promotor"
           /standard_name= "ACHE Promotor"

(ix) FEATURE:
       (A) NAME/KEY: exon
       (B) LOCATION: 22465..22537
       (D) OTHER INFORMATION: /function= "non-translated"
           /gene= "ACHE"
           /number= 1

(ix) FEATURE:
       (A) NAME/KEY: exon
       (B) LOCATION: 24090..25177
       (C) IDENTIFICATION METHOD: experimental
       (D) OTHER INFORMATION: /function= "(translation start:
           24110)"
           /evidence= EXPERIMENTAL
           /gene= "ACHE"
           /number= 2

(ix) FEATURE:
       (A) NAME/KEY: exon
       (B) LOCATION: 25524..26009
       (C) IDENTIFICATION METHOD: experimental
       (D) OTHER INFORMATION: /evidence= EXPERIMENTAL
           /gene= "ACHE"
           /number= 3

(ix) FEATURE:
       (A) NAME/KEY: exon
       (B) LOCATION: 27005..27274
       (C) IDENTIFICATION METHOD: experimental
       (D) OTHER INFORMATION: /evidence= EXPERIMENTAL
           /gene= "ACHE"
           /number= 4

(ix) FEATURE:
       (A) NAME/KEY: exon
       (B) LOCATION: 27255..28007
       (C) IDENTIFICATION METHOD: experimental
       (D) OTHER INFORMATION: /evidence= EXPERIMENTAL
           /gene= "ACHE"
           /number= 5

(ix) FEATURE:
       (A) NAME/KEY: terminator
       (B) LOCATION: 27385..27387

(ix) FEATURE:
       (A) NAME/KEY: exon
       (B) LOCATION: 28008..28129
       (C) IDENTIFICATION METHOD: experimental
       (D) OTHER INFORMATION: /evidence= EXPERIMENTAL
           /gene= "ACHE"
           /number= 6

(ix) FEATURE:
       (A) NAME/KEY: terminator
       (B) LOCATION: 28129..28131

(ix) FEATURE:
       (A) NAME/KEY: exon
       (B) LOCATION: complement (34528..34895)
       (D) OTHER INFORMATION: /function= "arsenite resistance
           gene"
           /gene= "AR"
           /number= 1

(ix) FEATURE:
       (A) NAME/KEY: exon
       (B) LOCATION: complement (34092..34358)
       (D) OTHER INFORMATION: /gene= "AR"
           /number= 2

(ix) FEATURE:
       (A) NAME/KEY: exon
       (B) LOCATION: complement (33779..33963)
       (D) OTHER INFORMATION: /gene= "AR"
           /number= 3
```

-continued

```
(ix) FEATURE:
    (A) NAME/KEY: exon
    (B) LOCATION: complement (33493..33591)
    (D) OTHER INFORMATION: /gene= "AR"
        /number= 4

(ix) FEATURE:
    (A) NAME/KEY: exon
    (B) LOCATION: complement (33297..33408)
    (D) OTHER INFORMATION: /gene= "AR"
        /number= 5

(ix) FEATURE:
    (A) NAME/KEY: exon
    (B) LOCATION: complement (32959..33094)
    (D) OTHER INFORMATION: /gene= "AR"
        /number= 6

(ix) FEATURE:
    (A) NAME/KEY: exon
    (B) LOCATION: complement (32569..32628)
    (D) OTHER INFORMATION: /gene= "AR"
        /number= 7

(ix) FEATURE:
    (A) NAME/KEY: exon
    (B) LOCATION: complement (32386..32468)
    (D) OTHER INFORMATION: /gene= "AR"
        /number= 8

(ix) FEATURE:
    (A) NAME/KEY: exon
    (B) LOCATION: complement (31894..32080)
    (D) OTHER INFORMATION: /gene= "AR"
        /number= 9

(ix) FEATURE:
    (A) NAME/KEY: exon
    (B) LOCATION: complement (31363..31534)
    (D) OTHER INFORMATION: /gene= "AR"
        /number= 10

(ix) FEATURE:
    (A) NAME/KEY: exon
    (B) LOCATION: complement (31131..31284)
    (D) OTHER INFORMATION: /gene= "AR"
        /number= 11

(ix) FEATURE:
    (A) NAME/KEY: exon
    (B) LOCATION: complement (30816..31011)
    (D) OTHER INFORMATION: /gene= "AR"
        /number= 12

(ix) FEATURE:
    (A) NAME/KEY: exon
    (B) LOCATION: complement (30470..30626)
    (D) OTHER INFORMATION: /gene= "AR"
        /number= 13

(ix) FEATURE:
    (A) NAME/KEY: exon
    (B) LOCATION: complement (30187..30274)
    (D) OTHER INFORMATION: /gene= "AR"
        /number= 14

(ix) FEATURE:
    (A) NAME/KEY: exon
    (B) LOCATION: complement (29945..30073)
    (D) OTHER INFORMATION: /gene= "AR"
        /number= 15

(ix) FEATURE:
    (A) NAME/KEY: exon
    (B) LOCATION: complement (29664..29856)
    (D) OTHER INFORMATION: /gene= "ARS"
        /number= 16

(xi) SEQUENCE DESCRIPTION: SEQ ID NO:7:
```

-continued

```
GATCAGTTGA AGCCAGGAGT TCGAGACCAG CCTAGCCAAC ATAGTGAAAT TTCATCTCCA      60

ATAAAAATAC AAAAATTAGC CAGACATGGT AATGCACACC TGTAATCCCA GCTACTTGGG     120

TGGCTGAGGC ACAAAAATTG CTGGAGCCTG AGAGGCAGAG GTTGCAGTGA GTGCCACTGC     180

ACCCCAGCCT GGGCAACAGA GTGAGACTCT GCCTAAAATA AAATAAAATA AAATGTATAA     240

AAGCTGTAAA CCAACCACCT TGGGCACCTG TTCTTAGGAC TTTTAGGGGC TATGTCATGG     300

GCCTTGGTCA CTCATATTTG GCTCAGCATA AATCTCTTTA AATATTTTAG AGTTTAACTC     360

TTTTTGTCAA CACATCAGTT GACAGTGATC AGTAGTCTAC CTAAAACTGC CTTTGTGAAA     420

ATTTTATCAC TGAGAAAAAT TATAATAGTA AGCAGAGTTA ACACCCTCCA CCTGCACCAC     480

CTTGCCTTTC CCTTGATTAT TTGGGGGCTA TTGGGCCAAG CTAACTTTGG AAGACATTTT     540

AGGTTATCAT TTAAATGATA ACAGGCCTTG CCCTGAAACT CCTCTCCTCC CCAAAGCCTT     600

TTGTAAAGCC AATGGGAGAC CATCAGGCTT GGAGGAGAGG AGCTTGAGTC CTAAGATTGG     660

CCTTTTGAGA TGTCTTTTCA GGATTTTTGC ATGTCAGACA TCCATGGCTC CACCTGAACC     720

CACCTGAATC CCCCACCAAA CCCACCCCTG TGGCCCTGCC CAGAAGCAAT TCTGCCTGCA     780

GGAGGCAGAA TTTCATCTCC ACCCCAACCA ATCAGCAGCA AGCACCTATT ACCTGGCCAC     840

CCTCATCCCT TTGTGGAGTC CTAATTAGGG AAAGGGAACC AGGCTGGTGG AACCAAGAGA     900

AAGCAAAAAG AGAAAGCAGA TAAGCAACAA GTCTGTCTTT CTTCATGATC CAGGACACAC     960

AGCCCTCCTG CACAAGTAAC TTACAACCTT TCCTGCACCC AGCTATCACC AGACACCTGC    1020

AAGTTAGCTC ACTGCAACTT TGATGTTATC AGTACTACAT AAAGCCCTCT TCAACAGAGA    1080

GCATAAACAC TACCCTATAA AATCTCCAGC GAGTCTTTGT TTTTTGCAGT CAGTTTCTCT    1140

TCTGCTGGTA GCCCGTTATC TCTCTGGCAG TGTATTTTCC TACTTTGTCT AATAAATTTG    1200

GCTTCCTTTA CTTACAACTG TCTTCACAAA TTCTTTTACC CCACACCACC AGCTGTCGTT    1260

TTCCCATGAC ACCCCTAACA TACAAGCTTT GGACAAGATG ATTTGAATGC TAACTCCATC    1320

TCCCATGTGG CATGGCGAGC CTTGTGTCTA TTAAACTCTT TCTCTACTAC AATGCCATGG    1380

TGTTTCTTTA CGCAGCAGGC AAGAAGAACC TCTCAGGTGG TTACACATCC TCCTGCTCTC    1440

CTTTCCAAGC TAGCTGCTGC TGAAGAAGAA CTAGAGGCAA AGCTGAGTGC CCTGGTGGAG    1500

GGGAGGACAG CTGCTTGCAC TCAGAAGCCT GCACAGATAC AGAGAGGTCA GCCACCATGG    1560

GAGTAGGGAT GAGAAATTCT GTCCTGCCAA AACCCCCACC AACCCAAAGA CAAAAGGAAA    1620

AGTTTGGCTG CCACGAGGAA GGACAGATAT GCTGAGAAAT TCCATCCCCA AGACCCAGGA    1680

GCAAAAAACT TGCCTGAGAC AGAGACTAGC CCTGAAGAAA TGGAATACCA TGCCTCTGTC    1740

AGAGGCAGGT GAACCAGAGC AACTCCATCT TGAATAGGAA CTGGGTAAAA TGAGGCTGAG    1800

ACCTACTGGG TGCATTCTCA GATGGTTAAG GCATTCTAAG TCACAGGATG AAATAGAAGG    1860

TCGGCACAAG ATACAGGTCA TAAAGACCTT GCTGATGAAA CAGGTTTTGT AGCAGGACAA    1920

GCCGCAGACA CAACCCCTCA GACACTGAGT TAAAGAAGAA AGGGCTTTAT TCAGCCAGGA    1980

GCTTCAGCAA GACTCACGTC TCCAACAACC GAGCTCTCTG AGTCAGCAAT TCCTGTCCCT    2040

TTTAAGAGCT CACAATTCTA AGCGGGTCTG CATGAGAGGG TCGTGATTGA TTGAGCAAGC    2100

AGAGGGTACG TGACTGGGGG CTGCATGCAC CGGTAATTAG AATGGAACAG GACAGGGATT    2160

TTCACAGTGC TTTTCTATAC AATAGCTGTA ATCTATAGAT AACATAACCA ATTAGGTCAG    2220

GGGTCAATCT TTAACAACCA GGCCCAGTGT GTGGCACTGG GCTGTCTTTT AGAAATGAAA    2280

TGTGGATTTC ATTTCTGCCT TTTAGTTTTT ACTTCTTCTT TCTTTGGAGG CAGAAATTGG    2340

GCATAAGACA ATATGAAGGG TGGTCTCCTC CCTTAGTTTC AGTAAAGAAG CCGGCCAAAA    2400
```

```
CCCACCAAAA CCAAGATGGT GAAGAGAGTG ACCTCTGGTC GTCCTCACTG CTACACTCCC    2460

ACCAGCGCCA TGACAGTTTA CAAATGCCAT GGCAACGTCA GGAAATTACG CTATATGGTC    2520

TAAAAAGAGG AGGCATGAAT AATCCACCCC TTGTTTAGCA TGTCATCAAG AAACAACCAT    2580

AAAAATGGTC AACCAGCCAC CCTCAGGGCT GCTTTGTCTA TGGAAAGGCC ATTATTTTAT    2640

TTCTTTATTT TCCTAATAAA CTTGCTTTCA CTTTACGGAC TCACCCTGAA TTCTTATGCA    2700

AAATCCAAGA ACCCTCTCTT GAAGGGTCTG GATTGGGACT CCTTTCCTGT AACACCTCTA    2760

CCATGAGCCT CACACCAAGT AACCCACAAG AACAGTCCCA AGCTGTTGGC AGGGTGAGGA    2820

AAGCAAGAAC ATGGGAAGAG ATCTTGCTTT GAAAGCCCCC AACTAAATGG GGGTTTCCGT    2880

AGCAGAGCAG CTAGTAACCC TGCTTTAATG GGAAATGAAG GACATGGTGT TTGCAGTGTC    2940

CCTTTCATGG GTTGCTTCTT TTGTTAGCAG CAGCGAATCC ACACGGGTCT GCAGCAATTC    3000

AATTCTTGCC TCCTCGAAGG AAATAATTCC TCTGAGGGGC ATAAGGCAGA GTGAGAGACT    3060

GAGGCAAGTT TTTGAGCAGG AGTCAGAGTT TATTAAAAAG TTTTAGAACA GGAACGAGGC    3120

CGGGCACGGG ACAGCTCATG CCTATAATCC CAGCACTTTG GGAGGCTGAG ATGGGCGGAT    3180

TGCTTGAGGC CAGGAGTTCA AGACCAGCCT GGCCAACATG GCGAAACCCC GTCTCTACTA    3240

AAAATACGAA AATTTGCCAG GCGTGGTGTC GGGCGCCTGT AATCTTAGCT ACTGGGGAGG    3300

CTAAGGCAGG AGAATCACTT GAACCCAGGA GGCAGAGGTT GCAGTGAGCT GAGATCACAC    3360

CACTGCACTC CAGCCTGGAT GACACAGCAA GACTCTGTCT CAAAAATAAT TAATTAATAT    3420

AAATTTTTAA AAAAGTTTT AGAGGAAAGA AAGGAAGTAA AGTACACTTG GAAGAGGGCC    3480

AAGCAGGCAA CTTGAGAGAT TCAAGTGCAC TGTTGAGCCC CTGACTTGGG GTTTTATACA    3540

TTGGCATGGT TCCGGGGGTT GCGTCTCTTC TCCCTTGATT TTCCCTTGGG GTGGGAACAG    3600

TATATTTACT GAAGTTGTGC ACATGCTCGT TTGAGGCGTT CTTCCCCTAC CAGCTGAGGG    3660

TTCCTGGGAA GACATAGATC TGTTGGCCAA GTGCAGTGGC TCACGCCTGT AATCCCAACA    3720

CTTTGGGAGG CCAAGGCAGG AGGATTGCTT GAGGTCAGGA GTTCAAGACC AGCCTGGCTA    3780

ACATGGTGAA ACCCCCTCT ACTAAAAATA TAAAAACTAG CTGGGGCCGG GCGCGGTGGC    3840

TCGCACCTGT AATCCCAACA CTTGGGAGGC TGAGGCAGGC AGATCATGAG GTCAAGAGAT    3900

CAAGACCATC CTGGCCAACA TGGTGAAACT CCGTCTCTAC TAAAAATAAA AAAAAAAAT    3960

TAGCTGGGCG TTGTGGTGTG TACCTGTAAT CCCAGCTACT TGGGAGGCTG AGGCAGGAGA    4020

ATCCCTTGAA CCTGGGAGTT GGAGATTGCA GTGAGCCGAG ATCACTCCAC TGCACTCCAG    4080

CCTGGGCGAC AGAGCAAGAC TCCATCAAAA ACAAAACAAA AAAGAAATAC CACTTAAACT    4140

CTGCCATGTT GCCTCTTAGT GCACATGCTT GAGCCCACTC ACCCAACTCC TGAGATCTTA    4200

TCAGGAAGCT GCTTATCACC AGCCTCAGGT GTTTTCTGTC TATTGGGAAA CCACCTTTCC    4260

CTGGCGCCAG CTACAACCAA TTATTATTTC AGAAAGACAG TTTAACAACC ACTTGACCAC    4320

CACCTATTTG TCACTTGACA TTACTGGGGA AGGGAATGGG GCATCCTCTC CTACCCTCCT    4380

CATGTCTGCC TAGATACCTA CTCTAACATA ACCAGCCACG GCAGGCCCAA GCTACTGGGG    4440

AGCGGGGCGA GCAAGAACAT GGAAAGACAC CCTGCTTTGA GAGCTACATG AGGGTCTCAG    4500

TAGCAGAGCG GCTAGCAAAC CTGCTTTAAG GAGAAATGAA GGGAAGCTGG GTGTAGTGTT    4560

CACAGCGGGC TTTTCACAGG ATACTTATTT ACCTAATGGA TGGCCTAATG CTTAGGGATC    4620

CCTAAAGGTC CCTTACTTGG GAAACTTGCT TATACTGGCA GACACCTCGT GGCTTTTGTG    4680

TGACCCACCA CGTCCAGTTT ATGCCTGCTG GATGGTCTCT CTGGCTCTGG GAGCCCAATC    4740

TTATGTTCCC CCAGGCGCCC CAGGGAAAAC CCAGCCTCAG ATTTCCCCTA GTTCTTCAGA    4800
```

```
TGGAAGTTGA AAATTCAGGA AAGCACTTTT ACCGGAAACA GGTCCTAATT CAGTCCGCAA    4860

GAGAGGGTTC TTGGATCTTG TGCAAGAAAG AATTTGGAAG GGCCAGGCGC AGTGGCTCAC    4920

GCCTGTAATC CCAGCACATT GGGAGGCTGA GGCGGGCGGA TCACGAGGTC AGGAGATCGA    4980

GACCATCCTG GCTAACACGG TGAAACCCCG TCTCTACTAA ATACAAAAAA TTAGCCGGGC    5040

GTGGTGACAG GCATGCCTGT AGACCCAGCT ACTCGGGAGG CTGAGGCAGG AGAATGGCAT    5100

GAACCCAGGA GGCGGAGCTT GCAGTGAGCT GAGATCATGC CACTGCACTC CAGCCTGGGT    5160

GACAGAGCGA GACTCCGTCA AAAAATAAAA AAAATAAAAA AATAAAAAAA TTGGAGTGAG    5220

TCCACAGAGT GAAGTGAAAG CAAGTTTATT ACAGAAGTGA AAAAACGTGA GAATGGCTGC    5280

TTCATAGACA GAGCAGCCCC GATGGCTGCT GGTTGGCCAT TTTTGTTTCG TTTTGTTTTT    5340

TATTGTTTGT TCTTCTTTTT TTATTAGTTT GTTTGTTTTG TTGGTTGGCT ATTTTCTAAT    5400

GGTTATTTAT TGATCGTATG CTAAAGAAGG GGTGGATTAT TCATGAGTTT TCCAGAAGAG    5460

GGGTAGGAAT TTCCCAGAAC TGAGAATTCC TCCCCCTTTT AGACCATATA GGGTAACTTC    5520

TGGGCATTGC TATGGCATTT GCAAACAGTC ACAGCACTGG TGGGAGTGCC ATTTAGCAAG    5580

CTAATGTATT ATAATTAGCA TATTATGAGC AGTGAGGACA GCCAGAGGTC ACTCTTGTTG    5640

CCATCTTGGT TTTGGCGAGT TTTGGCCGGC TTTTGTTGAG ACGGAGTTGC TCTTTCGCCC    5700

AGGCTGGAGT GCAATGGCAC AATCTCAGCT CACTGCAGCC TCCACCTCCC GGGTTCAAGT    5760

GATTCTCCTG CCTCAGCCTC CTGAGTAGCT GGGATTACAG GGCCCGCCA CCACGCCCGG    5820

CTAATTTTTT GTACTTTTAG TAGAGATAGG GTTTCACTAT GTTGGCCAGG CTGGTCTCGA    5880

ACTCCTGATC TTGTGATTCG CCCGCCTCAG CCTCCCAAAG TGCTGGGATT ACAGATGTGA    5940

GCCAAAGCAC GTGGCCATGG CTGGCATTTT TTTTATTGCA TCCTGTTTTA TCAGGGTCTT    6000

TGTAACCTAC ATCCTATCTC ATCCTGTGAC TAAGAACGCC TAACCTCTTG GGATGCAGCC    6060

CAGCAGGTCT CAGCCCATTC TACCCAGTCC CTACTCAAGA TGGGGTCGCT CTGGTTCAAA    6120

TGCTTCTGAC ACCATCACAA TAGGAAACAA GTTCAAAGAT TTCTTTTTAT TATTATTATT    6180

TTATAGAGAT GGAGTCTCAC CGGCCGGGTG CAGTGGCTCA CGCCTGTAAT CCCAGCACTT    6240

TGGGAGGCCG AGGCGGGCGG ATCACGAGGT CAGGAGATCG AGACCATTCT GGCCAACACA    6300

GTGAAACCCC GTCTCTACTG AAAATACAAA AAAATTAGCC AGGTGTGGTG GCGGGCGCCT    6360

GTGGTCCCAG CTACTCGGGA GGCTGAGGCA GGAGAATGGT GTGAACCCAG GAGGTGGAGC    6420

TTGCAGTGAG CTGAGGTCGT GCCACTGCAC GCCAGCCTGG GCGACAGAGT GAGACTCCAT    6480

CTCAAAAAAA AAAAAAAAAA GAGATGGAGT CTCACCATGT TGCCCAGGCT GGTCTTGAAC    6540

TCCAGGGCTC AAGTGATCCT CCTGCCTTGG CCTCCCAAAG TGCTGGGATT AAAGAAATGA    6600

GCCACTGTGC CTGGCCCCAG AGATTTTTTA CAGACAATAA ATAAGGGCCT CCTAGGCAGG    6660

AAGGGCACCA TGAGTCAGGA GGGCACCATG AGTTGGGAAA ACACCATGAG TCAGGAGGGC    6720

ACCATGAGTT AGGAGAACAG TCCTCCATCC CCAGGTCAAG TAGAGAAAGA GAGAATAGGA    6780

GTAGAGTCGA GTGGAGAGAG CATGTGGCAA CTAGCAGTAC ATATATAGAG AGGGGAATAC    6840

AGTGCCAGTC ACTTGAAGTT CAAGGGCAGA TGTCTAAATG CTCCACTTAA AGAAAGTGGT    6900

GGGGGCTGGG CGCGGTGGTT CATGCCCATA ATCCCAGCAA TTTGGGAGGC CAAGAGGCCG    6960

AGACGGGTGG ATCACTTGAA GAGAAGAGTT TGAGACTTGA GGTCAGGAGT TCGAGGCCTG    7020

GGCAACAGGG CAAGACTCTC TCAAAGAAAG AAAGAAAGAA AGAACCTCGT GGAGGTAGAG    7080

AGTTCGAGAC CTGGCCAGCC TGGTGAAACC CCATCTCTAC TAAAAATATA AAATTAGCC    7140

AGGCCTGGTC ACTTGCGCCC ATAGTCCCAG CTACTCAGGA GACTGAGGCA GGAGAATCGC    7200
```

```
TTGAACCTGG GAGGCAGAGG TTGTAGTGAG CTGAGATCGC ACCATTGCAC CCCAGCCTGG      7260

GCAACAGAGC AAGACTCTGT CTCAGAAAAA AAAAAAAAAA AGGAAGAACC TCGTGGAGGT      7320

AGAGTAGACT GACAGTTATC AGAGTGTAGG GAGGGGGCAG TGAAGAGAGG TTGGTTGATA      7380

GCTACAAAAA TACAATTAGA TAGAAGAAAT AGGCCGGGCA CAGTGGCTCA TGCCTGTAAT      7440

CATAGCACTT TGGGAGGCCG AGGCGGGTGG ATCACCTGAA GTCAGGAATT CAAGACCAGC      7500

CTGGCCCACA TGGTGAAACC TCATCTCTAC TAAAATTACA AAAATTAGCC GGGTGTGGTG      7560

GCATGTGCCT GTAATCCCAG CTATTCAGGA GGCTGAGGCA GGAGAATCGC TTGAGCTCAA      7620

GAGGCGGAGG TTGCAGTGAG CCAAGACTGC GTCATTGCAC TTCAGCCTGG GTGACAGAGT      7680

GAGACTCCGC CTAAAAAAAA AAAAAAAAAA GGAAATTGAA AAACAGGAAG CAAAAAACAA      7740

AGTCCTCCAC AATCACCAGC ATTTTACAGC TTGACATTCC TTCTAGGGTC CTGGGTGTAG      7800

GCAGAACATC CAATCTCATA GGACTGAGAT CACACAATAC GTATTATGCT TTTTCACGCA      7860

TCATGAATAT TTACCCATTC AAAACCTAAA GCTATGTGAG CATTTTGGTA ACCAAGAATA      7920

CACATCACCA ACTCAATCTG TTAAGGAAAA AAAATGTAAT CCTGCTTTTC TTGAGACAAA      7980

AATTTCATAG AAGACAAAAG TGGCAATAGG CATCTAGATA AAAAGCATTG GCAGAGTTCT      8040

GATTAAAAGA CTGCATTCCC TTAATGCTCA ATTTAAAATA AAAACGTAGA CCAGACACAG      8100

TGGCTCACTT CTGTAATCCC AGCACTTTGG GAGGCTGAGG CGGGCAGATT GCTTGAGCTC      8160

ACGAGTTCGA GACCAGCCTG GGCAACATAG CAAGACCCCT TCTCTACAAA AAATGCAAAA      8220

ATTAGCCCAG CGGGGTGGCA CACACCTGTA GTCCCAGCTA CTGGGGAGGC TGAGGTGGGA      8280

GGCTCACTTG AGCCCAGGAG TTTGAGGCTG CAGTGAGCTA TGATTATGCC ACTGTACTAC      8340

AGCCTGGGTG ACAGAGCAAG ACCCTGTCCC TTAAAAAGAA AAAATAGAT TTGGGGAAAA      8400

GTAGATCTTT ATAGAGCCGA ACACCTTTTT ATTTATTTAT TTATTTATTT ATTTATTTAT      8460

TTTGAGACAG AGTCTCGCTG TGTTGCCCAG GCTGGAGGGC AGTGGTGCGA TCTCGGCTCA      8520

CTGCAACCTC TACCTCCTAG ATTCAAGCAA TTCTCCTGCC TCAGTCTCCC AAATAGCTGG      8580

GATTACAGGC GCCCGCCACC AGGCCCAGAT AATTTTTTGT ATTTTTTAGT AGAGACAGGG      8640

TTTTGCCATG TTGGCCAGGC TGGTCTTGAA CTCCTAACCT CAGGTGATCC ACCCACCTCG      8700

GCCTCTCAAA GTACTGGGAT TACAGGCATG AGCCACCACA CCCAGCCTTT TTTTTGAGAC      8760

AGAGTCTCAC TCTGTCACCC AGGCTGGAGT GCAGTGGTGC GATCTTGGCT CACTACAGCC      8820

TCCACCTCCC AGGTTCAAGT GATTCTCCTG CCTCAGCCTC TTGAGCAGCT GGGATTACAG      8880

GCACCTGCCA TCATGCCCGG CTAATTTTTG TATTTTTAGT AGAGACGGGG TTTGGTCATG      8940

TTGGCCAGGC TGGTCTCACA CTCCTGACCT CAGGTGATCC ACACACCTCG GCCTCCCAAA      9000

TGCTGGATTA CAGGCATGAG TCACCACGCC TGGCCTTAAA TTCTTACTTA AATTTATTAA      9060

ACTTATTCTT ATTTAAATTC TTTTATTCCT CAATTCCTTT CTATAAATTT TCATTATTTT      9120

ACTTTGAAAT ATCTGCCAGG ACTTTCAAGA ATCATAATTT TGGCAACCCA TATGCCAGCC      9180

TTATGTGTCT CACAATTAAA GCACAATGTT TTGAGCATTG AAAAGAACCA ATATGTTGAT      9240

TCACACTCAC AGTTGCAAAA CAAACGTGTT AGGCCATTCT TGCATTGCTA TAAATGCCTA      9300

AGACTGGGTG ATTTATAAAG AAAAAAAGTT TATTTGGCTC ACGGTTCTGC AGGCTGTACA      9360

GGAAGCACGG TGCCAGCATT TGCTTCTGGT GAGGACCTCA GGAAGCTTCC ACTTACAGGG      9420

GAAGTTGAAG GGGAGCTGGC ATGTCACAGG GCAAGAGAGA GAGCAAGAGA GAGTGCGGGA      9480

GGGAGGTGCC ACACTCTTAA ACAACCAGAT CCCACTCACT ATTGCAGAAA CAGCACCAAG      9540

GGGTTGGCAC TGAACCATTC ATGAGAGATC CACCCCCATG AGCCAAATAC CTCCAACCAG      9600
```

```
                                           -continued

GGCTCATCTC CAACACTGGG GATTACATCT CGACGTGCAA TCTGGAAAGG ACAAACATCC    9660

AAACTATATC AACAAATGAA GGCTGGAGAA ATCCAAGGAC TGAAGGACAT CCTGGTTATA    9720

ATTCCTACAT TTAAGTCACA TTGAGATGTG ACATAGTATT GTACAACAGA ATTTTTAAAT    9780

CTTATTTGCC ATGCCTTAGA ATCTTTTTCT TTTGAGACGG AGTCTCGCTC TATCGCCCAG    9840

GCTGGAGTGC AGTGGCACAA TCTCGGCTCA CTGCAACCTC TGCCACCCAG GTTCAAGCAA    9900

TTTTCCTGTG TCAGCCTCCC AAATAGCTGG GATTACCAGT GCCCACCACA ATGCCCAGCT    9960

AATTTTTATA ATTTCAGTAG AGACAGGGTT TCACCATGTT GGCCAGGCTG GTCTCAAAAT   10020

CCTGGCCTCA AGTGATCTGC CCACCTCAGC CTCCCAAAGT GCTGGGATTA CAGATGTGAG   10080

CCACCTCACT CAGCCAGAAT CCCTTCCAAA TTAAAAATCA AACAGAAACC CCACAGAATC   10140

ACATTTGTTT GGCATTGCTC TAGTAATATG TGCATCTTGG GTGCAAGCGT CTAAATTGCT   10200

AAACCTGCAT CTGCAGTTTT ACATTTTAAG ATGCTTCCGG CCAGGCGTGG TGGCTCACGC   10260

CTGTAATCCC AGCACTTTGG GAAGCCGAGG CAGGTGGATC ACTTCAGGTC AGGAGTTCGA   10320

GACTAGCCTG ACCAACATAG TGAAACCCCA TCTCTACTAA AAAATACAAA ATTAGCCAGG   10380

TGTGGTGGCG CATGCCTGTA ATCCCAGCTA CTCAGGAGGC TGAGGCAGGA GAATTGCTTG   10440

AACCCGGGAG GCAGAGATTG TAGTGAGCTG AGATTGCACC ATGGCACTCC ATCCTGGGCA   10500

ACAGGAGCAA AACTCCGTCT CAAACAAACA AAACAAACAG AAAAAAGATG CTTCCGGCTG   10560

GGTGCCGTGG CTCACACCTG TAATCCCAAC ACGGTGGGAG GCTGAGGCGG GAGGATCACC   10620

TGAGGTCAGG AGTTCAAGAT CAGCCTGACC AACATGGCAA AACCCGATCT CTACTAAAAA   10680

TACAAAAATT AGCTGGGTGT GGTGGCGGGT GCCTGTAATC CCAGCTACTT GGGAGGCTGA   10740

GGTAGGAGAA TTGCTTGAAC CGGGAGATGG AGGTTGCAGT GAGCTGAGAT CGTGCCACTG   10800

CACTCCAGCC TGGGAGACAG TGTGAGACTC CATCTAAAAA AAAAAAGATG CTTCCATCCA   10860

CTGTTCATCT CAGATTAAAT GAAGACCAAG GCTAGGCACA GTGGTTCACG CCTGTAATCC   10920

CAGCACTTTG GGAGGCCCAG GTGGGTGGAT CACTTGAGGT CAGGAGTTCA AGACCAGCCT   10980

GGCAAACATG GCGAACCCCC TCTCTACGAA AAACACAAAA ATTAGCCGGG CGTGGTGGTG   11040

GGTGCCTGTA GTCCCAACTA CTTGAGAGGC TGAGGTAGGA GAATCACTTG AACCTGGGTG   11100

GTGGAGGCTG CAGTGAGCCA AGTGAGCCGA GATCACACCA CTGCACTCCA GCCTGGGCGA   11160

CAGAGCAAGA CTCTGTCTCA AAAAAGTAAA AATTTTTAAT ATAAATAATG TGATACTTAT   11220

TAACCCAGTG ATTGGGACAA ATCCAAATTG AGGGACATTC TACAAAGTAA CTGGCCAGTG   11280

GTCTTCAAAC GTGTCAAGGT CATGAAAGAC AAAGAATGAG GAAGTGTCCA AAACACAGGG   11340

CACTAGTCGG GCATGGTTGC TCACGCCTGT AATCCTAGCA CTTTGGGAGG CTAAGGTGGA   11400

CAGATTACCT GAGGTCAGGA GTTCAAGACC AGCCTGGCCA ACATGGTAAA ACCCCATCTC   11460

TGCTAAATAC AAAAATTAGC CAGTTGTGGT GGCAGACGCC TATAATCCCA GCTACTCAGA   11520

AGGCTGAGGC AGGAGAATCA CTTGAACCCG GGAGGCGGAG GTTACAGTGA GCCAAGATCG   11580

CGCCACTGCA CTCCAGCCTG GTTGCCAAAG CAAGACTCCA TCTCAAAAAA AAAAAAAAG    11640

AAAATAGAAA TAATGAAAAG AATACAGATA AGGCCTCCAG GATACAGCAA AAGCAATGCT   11700

TAGAGGACAA TGTATAGCAT TAAAGTAATT AGGTCAATAA ATAAGAATGA AAATAAATAA   11760

ACAGCCAAGT GTGGTGGCGC ACCTACAGAC CCAGCTACCG AGGTGGGAGG ATCACTTGAG   11820

CCCAGGAATT CTGAGCTATA GTGCACTATG CCAATCCAGT GTCTGCACTG AGTTTGGCAT   11880

CAATGTAGGG ACCTCCTGGG AGCGGGGCAC CACCAGATTG TCTAAGGACG GGTGAACCTG   11940

CCCAGGTCAG AAGCAAAGCA GGTCAAAACT CCCTGCAGAT CAGTAGTAGG ATTGTACCTG   12000
```

```
TAAATAGCCA CTGAACTCCA GTCTGGGCAA CATAGCAAGA GCCCCTCTCT AAAAAATAAA   12060

TAAATAAATA AAATTAATTA GAAATCCAAT TCCAGAAGTT GTAAAACAAA CAATAAAATA   12120

AACCTATAAA CCTGAGAGAG CACATAGACG TTAATAAAGA TAAGAGCGGA ACTTAATAAA   12180

CCGGAAAACT GGAAAACACA TGAAAGATG CTCAAATTTC CTCATAATAG AAAGTAGGCC    12240

AGGTGCGGTG GCTCATGCCT GTAATCCTAG CACTTTGGGA GGCCAAAGTG AGTGGATCAC   12300

CTGAGGTCAG GAGTTCAAGA CCAGACTGGC CAACATGACA AAACCCCGTC TCTACTAAAA   12360

ATACAAAAAT TTGCTGGACA TGATGGCACA TGCCTGTAAT CTCAGCTACT CGGGAGACTG   12420

ACACAAGAGA ATCAGTTGAA CCCGGGAGGC AGCGATTGCA GTGGGCAAAG ATTACACTGA   12480

GCCGAGATAG CACCACTGCA CTCCAGCCTG GGTGACAGGG CAAGACTCTG TCTCAAAAGA   12540

AATAGGAAAA ATTAAGCTAA TTAAACCCTT AATGCTTACT GAATTAAATA TATTAATTTA   12600

AAAATTAATT AATTTTTAAT TTTTAAAAAA ATAAAGTAAC TGGCCTGGTG CAGTGGCTCA   12660

CGCCTGTAAT CCCAGCACTT TGGGAGACCA AGGCAGGCAG ATCACGAGGT CAGGAGTTCA   12720

AGACCAGCCT AGCCAACATG GTGAAACCCC GTCTCTACTA AAAATACAAA AATGAGCTGC   12780

GCATGGTGGC GCGCGTCTGT AATCCCAGCT ACTCAGGAGC GCGCTTGAAC CTGGGAGGCG   12840

GAGGTTGCAG TGAGCCAAGA TTGTGCCACT GCACTCCAGC CTGGGTGACA GAGCAAGACT   12900

CTGTCTCAAA ATAAATAAT AAATAAATAA AGTAAAGCTG TACTGAAATA CCATTCACCT    12960

CTTAAATGGG ACAATTTTTT TTGTTTTGTT TTTGGAGTTT GTTGAGACAG GTTCTCACTC   13020

TCTCATGCAG GCTGGAGTAC AGTAGCATGA TCACAGATCA CTGCAGCCTC AAACTCCTGG   13080

GCTCAAGCGA TCCTCCCACC TCAGCCTCCC AAGCAGCTGT GACTACAGGC ACAAGCCAGC   13140

ACACTCAGCA ATTTTTTATT TTTTGGAGAG CTGGGAGTCT CACTATGTTG CTCATGCTGG   13200

TCTTGAACTC CTGGGCTCAA GCGATCCTCC CACCTCAGCC TCCCAAAGTG CTGGGATTAC   13260

AGGCATAAGC CACCACATCC AGCCAATTTT ATTTTACTTT TAAATATACT ATGTTGGCAA   13320

AACTATAGGC AACCAATAAC TAGTGACCCA GTAATACATG TTGAGGAATT TATCCCAGGG   13380

ATATACTTGC AACACTGCAA AATTATTTGT GCACTAAGTT TGTAATAGCA AGTAACTGAA   13440

AGCAACTTAA ATGCTCATCA GTAGGGACA AATTAAATTA TGTTACTTTC AACTGGGCAA     13500

GGTGGCTCAT GCCTGTAATC CCAGCACTTT GGGAGGCCAA GGCGTGCAGA TCACCTGAGG   13560

TCGGGAGCTC GAGACCAGCC TGACCAACAT GGAGAAACCC CGTCTCTACT AAAAATAAAA   13620

AATTAGCCGA GAGTGGTGGC ACATGCCTGT AATCCCAGCT ACTCAGGAGG CTGAGGCAGG   13680

AGACTCGCTT GAACCTGGGA GGCGCAGGTT GTGGTGAACT GAGATCGCAC CATCGCACTC   13740

CAGCCTGGGC AACAAGAGCA AAACTCCGTT TCCAAATAAA TAAATAAATA AATAAAATTA   13800

TGTTACTTTC ATGCAATATA AAGTATGCAG CTTTTCATTA AACAGGCAAA AAATAAAGAA   13860

TGAGGGCCAG GTGTGGTGGC TTATGCCTGT AATCCTAGCA CTTTGGGAAG CCAAGGCAGG   13920

TGGATCACTT GAGGTCAGGA GTTCAAGACC AGCCTGGCCA ATATGCAGAA ACCCTGCCTC   13980

TACTAAAAAT GGAAAAATTA GCCAGGTGTG GTGGCAGGCG CCTGTAATCC CAGCTACTTG   14040

GGAGGCTGAG GCAGGAGAAT CGCTTGAACT CTGGGGGCG GAGGTTACAG TGATTGGAGA    14100

TCACGCCACT GCACTCCAGC CTGGGTGACA GAGCTAAACT CCGTCTAAAA AAAAAAAAA    14160

ATGAGAAAGT CTATGATGTA CAAATCTGGA ACTATCCTTA AGATACACTG TTAGCTAGGT   14220

TTCTTTCTTT TTTTTTTAAG TCAAGTACAG AAGAGTGTGT AAAGGATGCT ACAATTATGT   14280

AAAAACATGG ATTCAGGGCA GAAAAATACC TGTTGATGAT ATATGCATGT ACCTGTTTGG   14340

GCTACAGAAA AAAATGAAGA AAAAAAGTGG GTAATATATG CAATATAGGA CCACAGTTAA   14400
```

```
CACTGCTTTA GGAATGAATA CTGGGTCGAG GAAGGCAGGG AAGAGGAGAA CTTTTCACTT    14460

TATACGTTTT CAATTTTATG AATTCACTAA CTGTCCAAAT AAATAAAATA TAACTTTTTT    14520

TTTTTTTTTT TAGGACAGGG TTTCCCTTTA TCCCCTAGGC TGGAGTGCAG TGGCACGATC    14580

TCAGCTCACT GCAGCCTTGA CTTCCTAGGC CCAAGCCATC CTCCCACCTC AGCCTCCTGA    14640

GTAGCTGGGA CCACAGCCAC GCACCGCCGC ACCCAGCTAA TTTTTGTATT TTTGGTAGAG    14700

AAGGGGTCT CCCTATGTTG CCCAGGCTGA TCTCAAACTC CTGGGCTCAA ACGATCCACC     14760

CACCTCGGCC TCCCGAAGTA CAGGGATTAA AGGCATGAGC CACTGTGCCT GGCCCAAAAT    14820

GTAACTTAAA AAAGGATATT CCCCAGCCAG GAAATAACTT CTCCCCACTC ATCTAAGATC    14880

TTTCCCCTCT CATTTCCCGC CATCACTGTT GCCTGCAGCA CAGACATTTG TTAAGTGCGC    14940

CCAGGACGAG GATGGGAGGG TGTCACAACT GAATGAAAGT AGGGAAGCCA GGCGCGGTGG    15000

CTCACACCTG TAATCGATTC CAGCTACTCA GGAGGCTGAA GGCAGGAGGA TCGCTCAAGC    15060

CCAGGAGTTC AAGGCCAGCC TGGGCAACAT AGCGAAACCC TGTATCTATC CAAAAAAAAA    15120

AAAAATAGCC AAGCTTGGTG CATGGGTCT GTAGTCCCAG CTACTCAGGA GGCTGAGGTG     15180

AGAGGATCCT TTGAGCCCAA GAGGTCAAGG CTACGGTGAG CTACAATCGC ACCACTACAC    15240

TCCAGCCTGG GTGACAGAGT GAGACCCCCA TCTCTTTTTT AAAAATTAAA AATTTAAAAA    15300

TAAAGGAGGA GGAGTCCCGC CCTAGATGCA GAGAGCCCCC AGATGTTCTG AGCTGATCCA    15360

TTTTCTGCTG TAGCTCCCAT GTGTCAATGG CCCAAAGCTT CCCAGCACAG CCCCAGCCCC    15420

GACCCTGGCC CTGCTGGGCA CCTCTCTAGT GAGGAGGGGA GGAAGCACCT GCCACTGCCC    15480

ACATGCCACC ACTCTAGGAC CCCAGGGTTC CCCACCCTCC CCTGTGGCAG AGCCCCAGTC    15540

TCTAAGTCAG TTAGGGAGAG GAAGGGTAGG GAGACAGGGC AGGCGCAGAG AGGGGCTAGG    15600

AAGTAATTGT CATCTCAATA TTTAAACTCG GGCCGGGCGC AGTGGCTCAT GCCTGTAATC    15660

CCAACACTTT GGGAGGCCGA GGCAGGCAGA CCACAAGGTC AGGAGTTCAA GACCAGCCCG    15720

GCCAACATGG TAAAACCCCG TCTCTACTAA AAATACAAAA ATGAGCTGGG TGTGGTGGCA    15780

CGCGTCTGTA ATCCCAGCTA CTCAGGAGGC TGAGGCAGGA GATTCGCTTG AACCCGGGAG    15840

GCAGAAGTTG CAATGAGGGG AAATCGCACC ACTGAACTCC AGCCTGGGCA ATAGAGTGAG    15900

ACTCTGTCTC AAAAAAAAAA AAAAAGAGG AGGAAGAACT TGGGGGAGAA TGGGAGGCAG     15960

AAGATAATCA TCTCCCAGGA AGCACAGGGA CTTGGGCAGG GACCCCCACC CCGCAACAAT    16020

GCACACACCC CACACCTCTC TCCTTGGAAG GGAGGGGCCA GGAGGGCCTG AGAGACTCTA    16080

CTTGATTTTC CAGAAGTTAC AGGAGAGAGT CGCTGCAAAA CAGCCCAGCC CATCCAGGTC    16140

AGAGTTCTCA CCCAAAGTCC AAAGCCTGCA ATTTACCAGC TGATGAAACG AAACAACCTC    16200

TGTATGATTA CCTGTATGTT AATGCCTCTG GGCATCAGTT TCAGTTTCCC AGCTGTTAAA    16260

TTGTACTAAA AATAGCCTGG GTGTGGTGGC TTATGCTCAT AATCTCAGCA CTTTGGGAGG    16320

CCAAGGCAGG TGGATCAGCT GAGGTCAGGA GTTGGAGACC AGCCTGGCCA ACAGGGTGAA    16380

ACCCCGTTAC TACTCAAAAT GCAAAAATTA GCTGGGCGTG ATGGCATGCG CCTGTAATCC    16440

CAGCTACTCA GGAGGCTGAG ACAGGAGAAT CGCTTGAACC CAGGAGGTAG TGAGCCGAGA    16500

TCACACCATT GTACTCCAGC CTGGGTGACA GAGTGAGACT CTATCTCAAA AAAAAAAAA    16560

AATTGTAATG AAAATACAGC CTACCCACTG GGGCTGGGCG CAGTGGCTCA CGCCCGTAAT    16620

CCCAACACTT TGCGAGGCCG AGGCGGGCGG ATCACCTGAG GTCAGGAGTT CGAGACCAGC    16680

CTGGCCAACA TGGTGAAACC CCGTCTCTAC TTAAAATACA AAAATTAGC CGGGCGTGGT    16740

GGTATGCACC TATAATCCCA GCTACTCGGG AGGCTGAGGC AGGAGAATCA CTTGAACCCG    16800
```

```
GGAGGCAGAG GTTGCAATGA GCCAAGATCA TGCCATTGCA CTCCAGCCTG GGCAACAAAA    16860

GCGAGACTTC GTCTAAAAAA AAAAAAAAAA AAGGCAAAGA AAATACAGCC TACCCCATTT    16920

GAATGCTACA AGTGAGAATT AAATGAAATG ATATTTAGCA AAGCATTCAG GAAGCGGCTG    16980

GCAAACAAGC TCTTCTTCCC CATACATGCT ACTGTGAAAG CAACATTGGA TCTGGGCTAC    17040

TCTTCCACTC CACCCTGTTG TCCCCAGTGT TGTGGACATT TAAGGGATCC AGCTGACCAC    17100

TGGGCCAACC TCACAGCCAG CCTGCACTGT CCCCAAGCCA GGTGGCAGAA TCCCAAACCA    17160

GTCCTCCTCA CTTCTGCACC AATCTTGTGT TAAATACTCA GTGTCCCTGG AAACCCCAGC    17220

CAAGGTCATC TATGGAACCT GTGCTTCCGG CACAGCTCTC ACTTGGCCAC TTGATACCTG    17280

CAGGGCAGCC AGGAGTGACC AGGAGCTCTC TGGGTGTCAA ACATCTATAG CACCTAGTGT    17340

AACCTCACCA GCTATTTCCA AGAAGCCATT CAAGATGCAC TGCTAACATT TAAACTGAAA    17400

ACCGAGTCAG GGTTGGCTGG AACCTGTGAG ACCAGGAACT GACAGCCAGT TGGACCAGCA    17460

TGCCAGGGAC CATGTCAGAT GGATGTCAGG TCATACCAGG GAAGATGAGT GGCAACATGG    17520

CGTTCAATGT ACTACTGGTG AATTAAATTG CATATTTCAC TCCTTTCAGA AGCACTCAAG    17580

TTCATGGGCA AAAGGAATG CCAAGAAAAG TACTGATCAG TTCTGATGGC CGGGCGCAGT    17640

GGCTCACACC TATAATCCCA GCACTTTGGG AGGCAGAGGT GGGAGGATCG CTTGAGCCCA    17700

GGAGTTCAAG ACCAGCCTGG GCAACATAGC AAGACCCCGT CTCTACAAAT TAATAAAATA    17760

TTTAAAAATT AGCTGGGCAT GGTGGTGCCA CCTGTGGTCC CAGCTATTCA GAAGGCTGAA    17820

GGAGGGTTAC TGCTTGAGCC CAGGACTTCA AGGCTGCAAT GAGATATGAT CACACCATTT    17880

CACTCCAACC CCGGGTGACA GCATGAGACC AAAAAAAAAA AAATTCTGAG CACAAGGGTA    17940

TGCCACCCGC ACTCCACTCT ACCCCCGGCC AGAAAAGAGG CTAAACTAAG CAAAAGGTTA    18000

TTTGGCGAAT TGCATGGGAA ATACTGTATA CTCGTTAAAT AAATAACAAA ATTGTGAAAA    18060

TAAAGTAAGA CTTTGTAGAG ACAAGCTATA AAAAATGTGT GAAATGCTCA TAACTAGCAA    18120

GAGAGAAAAG GGTAAAAAGG ATGGATAAGC CGCAAAGAGA AATCATCCTA TCCTGTGTAG    18180

GATGACGTAA CTTGGATCCA GCAGGAAGGC TGGCCCAACA TTAAGTAGGG GACATAGGAA    18240

GGGGTGGGTA GAGGGAGGAA AGTCCTTTGT GTGGCCTCAG GCTCCCAATT CTGCCAGGTT    18300

ACAATCTCGA TTAATGGGGG GTTGGGCAAA GGCTCATCAT TAAAGGAAGA GTTCGGCCGG    18360

ATATGGTTGC TCAGGCCTGT AATCCCAGCA CTTTGGGAGG CTGAGGCAGG TGGATCACTT    18420

AAGGCCAGGA GTTTGAGACC AGCCTGGCCA ACATGGTGCA ATCTCATCTC TACTAAAAAT    18480

ACAAAAAATT AACCAGGCAT GGTGGTGCGC ACCTGTAATC CCAGCTACTC AGGAGGCTGA    18540

GGTGGGAGAA TCACTTGAAC CTGGGAAGTG GAGGTTGCAG TGAGCCGAGT GCCACTGCAC    18600

TCCAGCCTGG GGCGACAGAG TGAGACTCTG TCAAATAAAT AAATAAATAG GAGATACTGT    18660

TCTTCAGCCC CTCCTCCTTC CTGCTGGCTG GAATGTAGAT GTGATGGCTG ATGTTCCAGC    18720

AGCCATTCTA TGCCATGCGG TAGAAGTCAC ATGCTGAAGA TGGTGCAGTA ACAAGATACT    18780

GTGCAAGGAG CAACAGGGTT CCGTGTAAAG AAGCCTGGAC CCTGACATTG AGGGCACCAT    18840

GCCAACCCTG CAAGACTCAT TTCTAGGTCT CTTTTTTTTT TTTTTAAGA CAGAGTCTCC    18900

CTCTGTCACC CAAGCTGGAG TGCAGTGGCG AGATCTTGGC CCACTGCAAT CTCCGCCTCC    18960

CAGGTTCAAG CAATTCTTGT GCCTCAGCCT CCCAAGTAGC TAGGAGTACA CGCACGCACC    19020

ACCATACCAA GCTAATTTTT GTATTTTTAG TACAGACAAG GTTTTACCAT GTTGCCCAGG    19080

CTGGTCTCAA ACTCCTGGCC TCAAGTGATC CTCCTGCCTC AGCCTCCCAA GTAGCTAGAA    19140

CTATAAGTAT GCACCACCAC ACCCAGCTAA TTATTTTTAT TTTTTGTAGA GACAGGGTCT    19200
```

```
CACCACATTG GCCATGCTGG CCTCATACTC CTGGCCTCAA GTGATCCTCT CTCCTTGTCC    19260

TCCCAAAGTT CTGGGACGAC AGTCACTGCA CCTGGCCCAA GAAATACATT TCTATTATTT    19320

TTTTTTTTTT TTGAGACAGA GTTTCGCTCT TGTTGCCCAG GCTGGAGTAC AATGGCATGA    19380

TTTCCGCTCA CTGCACCCTC CACCTCCTGG GTTCAAGCGA TTCTCCTGCC TCAGCCTCCT    19440

GAGTAGCTGG GATTACAAGC ATGGGCCACC ATGCCCAGCT AATTTTTTTG TATTTTTAGT    19500

AGAGACAGGG TTTCTCCATG TTGGTCAGGC TGGTCTTGAA CTCCCAACCT CAGGTGATCT    19560

GCCTGCCTCA GCCTCCCAAA ATACTGGGAT TACAACAGGC ATGAGCCACC ATGCCCGGCC    19620

TCTATTATAT CTTGTTAAAG CCATTATTTG GTTTTTGGTC TCATACAGCT GAATTGAATA    19680

TTAACCAATA AATAGAGGAA ATAAGAATCT TTTGTGTTAG AAGATGTGGA TCAAGGTCTG    19740

TAATAGAAGT GGGGTTCCCT GCCAGGCATG GCAGCTCATG CCTGTAATCC CAACACTTTG    19800

GGAGGCTGAG GCAGGAGGAT CACCTGAGGT CAGGAGTTCG AGACCAGCCT GGCCAACATG    19860

GTGAAACCCC ACCTCTGCTA AATATACAAA AATTAGCCAG GTGTGGTGGC AGGCGCCTCT    19920

AGTCCCAGCT ACTCAGGAGG CTGGGAAAGG AGAATCCTTG AGCCCAGGAG GCAGAGGTTG    19980

CAGCGAGCTG AGATGGCATC ATCTCTACAC TCTAGCCTGG GCGACAGAGC GAGACTCTGT    20040

CTAAAAAAAA AAAATGGCGC TTCCTTCCAA GGTGGGAGAC AGAGATAAAA GAGGGGTAGG    20100

GAAATTCTCT GAATTGGCAG AACTGGTAGT AGAAGCAAGG CTCATTCCTG GATAAACAGA    20160

AATGGTGAGA GAAGAAATGG GAAAAATCAA GGACATCCCT GCAGTGACAG CTGTGGAGGG    20220

TGGGGAGTTT ACTATGCTAG ACTATGTAGG GAAACGCCTC CTGGCTTGAC AGGTTAGGTG    20280

CCTGTGTTGA CAACGGTTGC TGAGAGCTCA AGGTGAAAAG AGGGATAGTT CCAGGAAATG    20340

ATAACCCTGG TGATAAACTA TCCCTGCCCT CCCTATCTTC ATTGTACAGG CCTAGAAACT    20400

CGTGACGACA GAGGTTAGGT GACACCTGCG TGGCACAGTT CGTCTGGAGG GTGACAGGGG    20460

CAAGCCTTCA TCACTAGCAG GGCCAAAAAT CCCTAAAGCC TCAGGACTGG GGCAGGCCTC    20520

AGAGCACTCG TTCACAGTTT GTTTCCATCA TTTTATTTTT TTGCGGAGAA GGGAGTCTCG    20580

CTATGTTGCC CAGGCTAGTC TCCAACTCCT GGACTGAAGC GATCCTCCTG TCTCGGCCTC    20640

CCAGAGTGCT GGGATTACAG GCACCGCACT AGGGGCCACA CGCGGCCCCA TCATTTTAAT    20700

AATTCATAAT TACCACGCTT AGAAACCTGC CTCAGATTCA TTCCCCCCGC AGCAACACCC    20760

ACCATCCACC CTCCTGTCCC CTCCCCCATG CACAGCCCTT ACATCTGCTC TTCAGGGATC    20820

TCAACTAGGG CACATGGTCT GGCCAGTGAG GAGCCTTCAA CTAGTGCGGC CAGAACGCTG    20880

AAGGCCGGAT ACAAGGAGCC TCGGTGTCCA GGCAGGGGAT TTGGGGTTGC CTGAGATTGG    20940

GGCGGGGAAA GCCGGAGACA GTGGGCACAG ATGGCGAGGG GTTCACCTCC CCAACACCCC    21000

CAACCCAGCC CAGTCTCCGA GGCCCGAGTG GCTGCTTTTT GCGCCACCTG GCGGCCGTCT    21060

CCAGCGAGCG GAGCGCGGGT GACCGTGCCT GCGGGACCCG GTTCCCGTGG GGCGAGCGGG    21120

CGTGGGGCCC GCCCAGCTTG GAGAGCCGGG AACCGCGCGG CCCAGGGACT GGCAAGACTC    21180

CGGATTCAAC CCCTGCGAGG CCCCGCAACC CGGTGCCCGC GGTCCCTGGC GGCGGCGCCC    21240

GCGTGCCCGA GGCGCTGCGG GGCGCTGCGG GGCGCGCGGC GGTTAGAGCG AGCGTGTGCG    21300

CACGCGCCCA CCCCACGCCG CGCCCCGCAC CGCCGCGCGC GCGCACGCAC GCCCGACGCT    21360

GGCCTGCGCC GGCCGCTCTC CCACGCGGGG TCTCGGGGGC TCCTGAGCCG GCCGCCTCCA    21420

GGAAGCAGGC GCCGCGCGGT ATTGCCGCAT GCACCTCGGT CGTGGGGACC CCGCTGCAGC    21480

AGCCCTGTCC ACACGGGTGA ACTCCTGGAG GGCGGGGCG GGGGCAATCT GCGCGGGTCA    21540

GGCCCCTCGG AGCAGGCTGG GGGCGCCCGA GCCAGGCCGC TCCCACCTGC CAGCCGCGTG    21600
```

```
GCCAATGAAT GCTAGGCCTG GTGATGTCAT GCCCCGACCG GACCCTGGTG ACGAAAGTCC   21660
GAAGTCACCC GTCAGGGAAC CAGCACAGAC CCACCCGCGG GGGTTCCAGA AGTTTCCACT   21720
GCCGCCGCGG AGTGCGGCCT CGCCCAGCAG CCTTGCGCGT GCTACCACGC TGTCCTGCCT   21780
TCTCAGGTGT CCCAAGTCAC CCCTTCCTCC CCCAGGGGTC TCCTGTCTCC ATGCCCTCCC   21840
ACCTCATTTC CACTAGCGAT CCCATTTTAC ATCTCCATTC CCACAGGTGT CCTTTCATCC   21900
CCAGGAGTGT CCCACGTCAC CTTTTCTGCA CCCGTGCCAC CTGGACCCCT AAGGGGACGG   21960
TACTCTGCCA CACTCCCACA TGCCTCTCCT CCCATGCCAC CCGTCTGTGT CGTGGCCGGG   22020
GATGCATGAC CCCTTGGCCT TGCGCTAACT TCACCAGCCT CGAGCGAGAC CGACAGGGTG   22080
TCCAAGTGTG TCCGTCCGTC TGTGAAAGTC GTCCCTGCGT TTGTCTGTGC CTGTCACTGC   22140
ATGAGGTCGT CCGTCTGCGC GTGTCTGTCT CCACGGGCTT CTGTCCGTCT GTCTGTCACG   22200
TGGGTGTCTA CTCCGCCGCT GCAGGTCTTT GGGTCGCGTC TGTCACTGCG CTCTGTCGTC   22260
GGTCGGCGTC TGGCACTGGA GTGCGTCTGG GCCCCGGGGT CTCCGGGTCT CGGCTCCAAG   22320
GGAGGGAGAG AGAGGGGAGG TGGCCACCCG GGAGAGCGGG GAGGGCGGGG GCGGAGACA    22380
GTGGGCGGGG GCGGGCGGGG GCGCTGTGAG GCCCGGAGGG GGTGTGTGCG GGGGGCCGGA   22440
GGCGGCGGCT GTCAGAGTCG GCTCAGCCTG CGCCGGGGAA CATCGGCCGC CTCCAGCTCC   22500
CGGCGCGGCC CGGCCCGGCC CGGCTCGGCC GCCTCAGGTG AGTCTCCCTC CCCGCCCGGG   22560
ACTCTCCTTA AGGCCCGGGT CCGGGGCACC GTGCGCTCCC CGAGGGGTCC AGGCCCCCCT   22620
AACGGGACGG CTCCCGCTTC CCCGGGCCTG CCCCGCGCCG CCCTCCGCTG CCCCGCACTC   22680
GTCCGGAACT CTTCCCCGGC CGCCTCACAC TCACCGACGC CCACGCAGGA GCCCGAGCCC   22740
GCGGGAACGG CCGCCGCCTC TGCGCTCCGA TTCCCGCGGG GACCCCCGAG CACCCCTTCC   22800
CCGATCGCTC CCTAGTCCGG GGCCACTGGA AGACACCCCC TAATTGGGGC GGTACCCGAG   22860
CTGCGCAGGT TCCCGGCGCC GGGCTGGGCA CCCCCATCCC CAGGGCCACA AGCCCAGCGC   22920
CCCTGCGCAG CGCCCCGCAG AGGCCCCCTC CGAGGCCCAG GACGCCCCCT CCCGCGGAGA   22980
CTCCATCTCT ATTTTTTGGG AAGGGGAGGC TCGGCGGAAG CCCCGAGTTA TAATTAGCGC   23040
CACTCGGGTT TCCTAGTTAA TCTCCAGCAG CACCACCACC CCCCGCTCAG GGCGGCGGGG   23100
GCTGGGCTAG GAGTGACCGG CGGGAGAGGG GGGAGTTCCC ACCCGGGGAA TTTTGATCCT   23160
TTGGCTGGAG ATGCCGGAAC CGTAGCAGCT GCTGCCCCCA AAATAGCGCC CCCGCCCCTG   23220
CAGCCGGGGA TCTCCGGAGT CCCGGGAACG CAGGAGTCCC GGCTCGCCCT TCAGGCGGCT   23280
CTGCAAGGCC CTCGAGCCCC CAGGCCCCCT CCCCAAGTTC CCGGCTCCTG GCTCGGGGCG   23340
GGGAGCGCCG ACCTTTTCTC GGTCTCTACT GCCCTCCGCC GGCGGCGGCG TGCACGGCAG   23400
CTTCAGACGG ATGGGGGGCT CTCGAGTCCT GGGGGACGCG GGCTGGCGAG CCTGTTTGCT   23460
GGGGCTGCGC TGGGAGCGTG CGCAGCTGAT GGGAACCCGC GGGCATCAGC GCTCGGTGCC   23520
AGACATTGGA TGAGAAGGGG CAGGGTTGGG TGGGAGTGG  ACTAGGCAGG ATTTGGGGA    23580
CCCCGGGACC TGAGGCTTCC ACACCCTGAA TGCCCAGCCC ACCGCCCCCC AGGGCCCCGG   23640
GTCTGGCCGA CCCAGGAGAG CGGGGATGCG CCTTCAGGCC GCCGCAAGCT CCCCCAGCGG   23700
CGCTGCCCGT CCGTGAGGCC GCGCCCCTGT CGGGTGGCCT GTTCGTGGAC TGAGGCTTCT   23760
GGTGCCCTCA CTGCACGAGC TGGGCCCGGC CCAGTTCCGG GAAGAGGTGA GGGCAGTGGA   23820
CCCCTGCGGA GCAGAAAGGG TGCTCCTCTC TGTTCCCTGC ATTTGTCTGG ATATGGGTGT   23880
CTGCCTGATC TCTTTCCCCT CCTGCCCGCT GGCCTGTGTC CTTGTCTCTG CCTGTCTCCT   23940
TCCCTCCCTC CCTCTCTCCC CTCATCTTTG CCAACCTGCC CCACCTCCTC TGCAGCTGAG   24000
```

```
CGATAACCCT TGGGCCGACA GTGCCCTAAT CTCCTCCCTC CTGGCTTCTC GACCGACCCT   24060

TCACCCTTTC CCTTTCTTTC TCCCAGCAGA CGCCGCCTGC CCTGCAGCCA TGAGGCCCCC   24120

GCAGTGTCTG CTGCACACGC CTTCCCTGGC TTCCCCACTC CTTCTCCTCC TCCTCTGGCT   24180

CCTGGGTGGA GGAGTGGGGG CTGAGGGCCG GGAGGATGCA GAGCTGCTGG TGACGGTGCG   24240

TGGGGGCCGG CTGCGGGGCA TTCGCCTGAA GACCCCCGGG GGCCCTGTCT CTGCTTTCCT   24300

GGGCATCCCC TTTGCGGAGC CACCCATGGG ACCCCGTCGC TTTCTGCCAC CGGAGCCCAA   24360

GCAGCCTTGG TCAGGGGTGG TAGACGCTAC AACCTTCCAG AGTGTCTGCT ACCAATATGT   24420

GGACACCCTA TACCCAGGTT TTGAGGGCAC CGAGATGTGG AACCCCAACC GTGAGCTGAG   24480

CGAGGACTGC CTGTACCTCA ACGTGTGGAC ACCATACCCC CGGCCTACAT CCCCCACCCC   24540

TGTCCTCGTC TGGATCTATG GGGTGGCTT CTACAGTGGG GCCTCCTCCT TGGACGTGTA   24600

CGATGGCCGC TTCTTGGTAC AGGCCGAGAG GACTGTGCTG GTGTCCATGA ACTACCGGGT   24660

GGGAGCCTTT GGCTTCCTGG CCCTGCCGGG GAGCCGAGAG GCCCCGGGCA ATGTGGGTCT   24720

CCTGGATCAG AGGCTGGCCC TGCAGTGGGT GCAGGAGAAC GTGGCAGCCT TCGGGGTGA   24780

CCCGACATCA GTGACGCTGT TTGGGGAGAG CGCGGGAGCC GCCTCGGTGG GCATGCACCT   24840

GCTGTCCCCG CCCAGCCGGG GCCTGTTCCA CAGGGCCGTG CTGCAGAGCG TGCCCCCAA    24900

TGGACCCTGG GCCACGGTGG GCATGGGAGA GGCCCGTCGC AGGGCCACGC AGCTGGCCCA   24960

CCTTGTGGGC TGTCCTCCAG GCGGCACTGG TGGGAATGAC ACAGAGCTGG TAGCCTGCCT   25020

TCGGACACGA CCAGCGCAGG TCCTGGTGAA CCACGAATGG CACGTGCTGC CTCAAGAAAG   25080

CGTCTTCCGG TTCTCCTTCG TGCCTGTGGT AGATGGAGAC TTCCTCAGTG ACACCCCAGA   25140

GGCCCTCATC AACGCGGGAG ACTTCCACGG CCTGCAGGTA ACTAGTGGCT AGCTGGCGTG   25200

AAGCTGGCTC CTCTGGGTCC CAACGGTCCC TCCCCTCCCT GCAGGGACCC AGGCATGAGG   25260

GCTTCTCCAG GCCCATTCCC AGAAGTCCCA GAAGTCCTCC CTGAGGGCTC AGATCCCAGG   25320

GTGGTCAGCA GGGCAGACAG GAAAGCCACC ATGGGTCTAT TTTCTCTTTC TCTGCATCCC   25380

TCCCCTGATC TCGTCCTCTC TCTGTCCATG GTTCCGGGTC TGTAACTGTT CATCTCTCTG   25440

GCTCTTTGTC TGTCCATCTG TTTCTGTCTA CTTGTCTGTC TGTGCCTGTC GCTCCATCCC   25500

ACCCCCCTCT CCCTCACCCC CAGGTGCTGG TGGGTGTGGT GAAGGATGAG GGCTCGTATT   25560

TTCTGGTTTA CGGGGCCCCA GGCTTCAGCA AAGACAACGA GTCTCTCATC AGCCGGGCCG   25620

AGTTCCTGGC CGGGGTGCGG GTCGGGGTTC CCCAGGTAAG TGACCTGGCA GCCGAGGCTG   25680

TGGTCCTGCA TTACACAGAC TGGCTGCATC CCGAGGACCC GGCACGCCTG AGGGAGGCCC   25740

TGAGCGATGT GGTGGGCGAC CACAATGTCG TGTGCCCCGT GGCCCAGCTG GCTGGGCGAC   25800

TGGCTGCCCA GGGTGCCCGG GTCTACGCCT ACGTCTTTGA ACACCGTGCT TCCACGCTCT   25860

CCTGGCCCCT GTGGATGGGG GTGCCCCACG GCTACGAGAT CGAGTTCATC TTTGGGATCC   25920

CCCTGGACCC CTCTCGAAAC TACACGGCAG AGGAGAAAAT CTTCGCCCAG CGACTGATGC   25980

GATACTGGGC CAACTTTGCC CGCACAGGGT CAGCAGTGCA GAGGGAGAGA AGGCTGGGGA   26040

GGACAGGAGT CGGGGGCGGG AGGACACACA AAGGCAGACA CACGGAGACA GAAAGGACGG   26100

GTGGGACAGG GGCAGGATAG AACAGCCAGA GAGGGATATG CTCACAAAGT AGATAAAAGG   26160

GGAGAGAAAA AGAAAGGAGA CAGAGAAGGC AGAGGGGGTC TTGCAGAGAC AGAGGCAAAG   26220

GAAAGTGAGG AGGAGACGAG GTAGACATGG AGGGGCGGG GCACAGTGGC TCACCCCTGT    26280

AATTCCAGCC CTTTGGGAGG CCAAGGTGGG AGGATCCCCT GAGACCAGGA GTTTGAGACC   26340

AGACTGGACA ACATAACAAG ACCCCGACTC TTAAAAAGAA AAAAAATACA AAACTTAGCC   26400
```

```
AGGCACGGTG GCTCGTGCCT CTAGTCCCAG CTACTTGGGA AGGTGAGGCA GGAGGATTGC   26460
TTGAGCCTGG GAGGTTGAGG CTGCAGTGAG CTATGATGGC ACCACTGCAC TCCAGCCTGA   26520
GTGGCCCTAT CTCTGGAAAA AAAAAAAAAA AAAAAAAGG  GAGACCAAGA CAAAGGAGTT   26580
GGAGCTGGAT TAAGTCAAAC CAGTGATGAT TCACTAGCAG TGACACATTC TCTCACACAC   26640
ACACCAGTTT ACCTGGATCG AGAAGAGGAC AATGAAATCT AGCATTGGAT GGGTGTTGTT   26700
AAAAAATGTG ATGTTTGTAG ACATAGGACC CGTCCTGGTT ATTTAGGAAA GTCTCAAGAC   26760
ATCCTAGCCA TTTTTTTAGT GAGAGAAACA AAGATGGAAC AGAAAAGCTG AGGGAAACGG   26820
AAGGAGACGG AGCGCTTGAG GAAGGGAAGA CCCCAATGAC CGCGCACATT GGAGAAAGTG   26880
GTGGGAGGGA GGGGACGGGT TCTCTGGGGC TCTCCGCTGA GCTGAAGAGT CCGGGATCCC   26940
GTGGAGTTGG GGGCCACCTC CTCCCACTGC CCGTCTGGAC TGAGCCTTCC CTTCCTTCCG   27000
CAGGGATCCC AATGAGCCCC GAGACCCCAA GGCCCCACAA TGGCCCCCGT ACACGGCGGG   27060
GGCTCAGCAG TACGTTAGTC TGGACCTGCG GCCGCTGGAG GTGCGGCGGG GGCTGCGCGC   27120
CCAGGCCTGC GCCTTCTGGA ACCGCTTCCT CCCCAAATTG CTCAGCGCCA CCGGTATGCA   27180
GGGGCCAGCG GGCAGCGGCT GGGAGGAGGG GAGTGGGAGC CCGCCAGGTG TAACCCCTCT   27240
CTTCTCCCCC TAGCCTCGGA GGCTCCCAGC ACCTGCCCAG GCTTCACCCA TGGGGAGGCT   27300
GCTCGGAGGC CCGGCCTCCC CCTGCCCCTC CTCCTCCTCC ACCAGCTTCT CCTCCTCTTC   27360
CTCTCCCACC TCCGGCGGCT GTGAACACGG CCTCTTCCCC TACGGCCACA GGGGCCCCTC   27420
CTCTAATGAG TGGTCGGACC GTGGGGAAGG GCCCCACTCA GGGATCTCAG ACCTAGTGCT   27480
CCCTTCCTCC TCAAACCGAG AGACTCACAC TGGACAGGGC AGGAGGAGGG GGCCGTGCCT   27540
CCCACCCTTC TCAGGGACCC CCACGCCTTT GTTGTTTGAA TGGAAATGGA AAAGCCAGTA   27600
TTCTTTTATA AAATTATCTT TTGGAACCTG AGCCTGACAT TGGGGGGAAG TGGGAGGCCC   27660
CGGACGGGGT AGCACCCCCC ATTGGGGCTA TAACGGTCAA CCATTTCTGT CTCTTCTTTT   27720
TCCCCCAACC TCCCCCTCCT GTCCCCTCTG TTCCCGTCTT CCGGTCATTC TTTTCTCCTC   27780
CTCTCTCCTT CCTGCTGTCC TTCTCCGGCC CCGCCTCTGC CCTCATCCTC CCTCTCGTCT   27840
TTCGCACATT CTCCTGATCC TCTTGCCACC GTCCCACGTG GTCGCCTGCA TTTCTCCGTG   27900
CGTCCTCCCT GCACTCATAC CCCCCCTTCA ACCCGCCCAA ATGTCCGATC CCCGACCTTC   27960
CTCGTGCCGT CCTCCCCTCC CGCCTCGCTG GGCGCCCTGG CCGCAGACAC GCTCGACGAG   28020
GCGGAGCGCC AGTGGAAGGC CGAGTTCCAC CGCTGGAGCT CCTACATGGT GCACTGGAAG   28080
AACCAGTTCG ACCACTACAG CAAGCAGGAT CGCTGCTCAG ACCTGTGACC CCGGCGGGAC   28140
CCCCATGTCC TCCGCTCCGC CCGGCCCCCT AGCTGTATAT ACTATTTATT TCAGGGCTGG   28200
GCTATAACAC AGACGAGCCC CAGACTCTGC CCATCCCCAC CCCACCCCGA CGTCCCCCGG   28260
GGCTCCCGGT CCTCTGCATG TCTCAGGCTG AGCTCCCTCC CCCGCGGTGC CTTCGCCCCT   28320
CTGGGCTGCC AATAAACTGT TACAGCCACG GGAGTGTGCG CGACTAGGGA GCCAGGGGTA   28380
GAGGCAGAAC GCCGGAATCA CGGGGGCCGA GTCTATGCAG GAGCGGGGCT GGAGGGCAAG   28440
AAACAGGCGA GCTCCGAGGC GGGCGCAAGG CAAAGGCCAA CCCCTAGCCC TGCCCTGCCG   28500
GGCGGAGCTC GCGCCTGCGT AATGAGGCCC GCAGGCAGGC TAGCTGGCAC GGCGGAGGGG   28560
AGGAGAGGGG AGGGGAGGGG AGGGGAGGGG CGGGGCGGGG CGCGGCGGAG CATTGTGGGA   28620
GCTCCTCGGT CGGTGCCGGT CGGTGGCTGC CTATTGCGGC CTGCGGTGAT CAACGAGGCC   28680
CGGGGAGCGC GTCCCCAGTC TGCGCGCCGG TCCTGCGGCA GCTGGCCCAA GACCCGGAGC   28740
CGAAAGGAAG TGTTGGAGCC TGAGGTCGCT CCGCGCCGCT AGGAGGACGC TGTGCCTGGC   28800
```

```
CTGGGACCTC CGCTCCCGCC CACCGCCCTG GAGCCGCTGA GGGACGTCCA CGTGGGCCTG    28860

TCCCCGCCGA GCCGCGGCCC TGTCCGCCTG GCGCTGCTCT CGGGCCACTA CCTCTACTAC    28920

CACTACGGCT GCGACGGCCT GGACGACCGC GGCTGGGGCT GCGGCTACCG CACTCTGCAG    28980

ACGCTGTGCT CGTGGCCAGA GGGCCAGCCC GCGGGCGTAC CTGGACTGGC CGCCGTACAG    29040

GCGGCCCTGG AGGACATGGG CGACAAGCCC CCCGGCTTCC GGGGCTCCCG GGACTGGATC    29100

GGCTGCGTGG AGGCCAGCCT CTGCCTCGCT CACTTCGGAG GGCCCCAGGG ACGCCTCTGC    29160

CACGTACCCC GGGGAGTGGG GCTGCACGGG GAGCTGGAGA GGCTTTACTC GCACTTCGCA    29220

GGGGGTGGGG GCCCAGTCAT GGTTGGGGGG GACGCAGATG CCAGGTCCAA GGCCTTGCTG    29280

GGAGTCTGCG TAGGGTCAGG CACGGAAGCC TATGTCCTGG TATTGGACCC TCACTACTGG    29340

GGCACTCCAA AAAGCCCCAG TGAACTACAG GCTGCTGGGT GGGTGGGCTG GCAAGAGGTG    29400

AGTGCAGCCT TTGACCCCAA CTCCTTCTAC AACCTGTGCT TGACCAGCCT TAGCTCCCAA    29460

CAGCAGCAGC GCACCTTGGA CTGAGGACGA AGTTACAGAA CTGAGATTCT CGGGTCCCAG    29520

ACACGCACCT ATGTACCTCC CACTGGTGTC CCTGCAAAGC CTGGCGCTTT TGACATCAAT    29580

AATAAAAGTG GCAGGGCTGA GCAACACCTC AGGAGTTACT CTGGAAGGAT GGAGGAGTTA    29640

TGTAACACAC GAGAGTCAGG AGCCCTGTGG AAGTGCTTTT ATTAGCAGTA AGGCTGATCG    29700

TACAAAAAAT TCTCAGAGCT TCATAGGACA AGGTAGTACA AGTATGGATG ATACAGGACT    29760

GAGGAACGGG GGACGGCTCA AAAGAAATCT ACATCGTCTG GGGCATCCAG GTCCCGATAT    29820

TCCACAATGG CCCTTGGGTC TCCACGAACC ATCCTGTGAG GTGAGAGGTA CAGGATGAGA    29880

GCTGAGGGCT CCCAAAAGGG AGTCTGCAGG CGTCAACAAA GCTTGGGCGT CTGCCCTCCT    29940

CACCTGTTGC GAGGTTTCCC AGGATAACCT CCCTGGCCTC GGAAGGCATC ATAGTTCCCT    30000

CGACCAGCAC CATACGGGGC ATGGGGGTAT GGAGGGCCTC CTGTGGGGAC TGCAGGGCGG    30060

ACAGCACCAG CTATGACAGA GATCAGTGTT GAGTTGCAAA ACTATGTCCT CAATTCCATC    30120

CTCTGTTTTC TTCTCCCAAA GCCACACACT CACCAAGCCC CTTCATCTCC CTCCTGTACT    30180

TACCTCCATA GCCCAAGATC GGGGGCCGGG GCTGACCATA GGGCATCAGG CCCTGGGGAG    30240

TCTGGTGTGG GTAGGGGAGT CCTGGGGTCA AACCTGGGGG GAGTACAACA CGGACAGGGA    30300

CATGAATTAC TGCGGGGGCG GGGAGGGGGA TACGGGTACA ATTGACTTCT AGGGCTATGG    30360

CCTGAGGATG GGGCAGAAAC TTCTCGGGGT GACACGTTAA AGAGAAACAG GAGTCCCTGG    30420

GTAGTCAAGG AAGAGGGCAC ATGCGACCTT CATGGATCGT ATCTTACTCT GGGCGGGGCC    30480

AGGTGGCTGG GCTGGCTTGA TCTCAGGCAG AGCTGGGCGC TTAGCATCAG TGAGGAAGTT    30540

GTTAAAAAAC GCGACTTCCT TTTTCACTTC CTCAATTTTC TCTGCATGCT TGTTGAAGAT    30600

ATGTTTGCGC ACAAACTCAG GACCCTGGGT GGAGAGAGGA GAGGGGTCAG GACAGCCACA    30660

TAAGGGTTGC CTCGCTCCCA GGCCCGAGCT GGAAGGATTC CCAGCTCCCG CCTGCCAGTG    30720

CAGTAAGCAG TTCCCCCACC CCTGCCCAGG GGGCTTCCTG TCTCAACCCC ACCTCCCACC    30780

ACCGTAGCAC GGCCATTCTC CAACATCCCA CACCTTGAAT TTCTTGCCAC TGAGAGGACA    30840

CAGCCACTTA TCCTTGCCCA GTTCCTGCGT GTTGGAGGTG ACGAACTTCT CCACTTCCTG    30900

CTCTGGGTCT TTGCGCCCCA TCTTCTGGGC CTCTTCCTCT GAGAGTGACT CCCGCACACT    30960

CAGCAACGGC GTGAGCTTCT CCTCAAAAGT CTTCTGCCAC TCCAGCACTG TGGTTTGGGA    31020

ACAGAGGAAG GAAGGTTGGC AAGGGAGCCA GAAGGAAGGA TGGTGGCAAG GGGCTGGAGG    31080

ACCAAGGCCA GGGGCAGCCG GGAACAAAGG GGAACCTGGA GCTCACCTTC CCCGTGACTG    31140

ATGCGGTTGG GTGGCATGGG CCCCCGAACG TGGATGATCC CACAGCGATT GGGCATCTCG    31200
```

```
TCCTCGTTGG GGTACTCACA GGTGTTGTAA TAATCCAAGG AATGCACGAT GCGCAGGTAA    31260

AGGAGGAGCT TGTCCAAGAC CTAAGGGAAG TGAATGCGAG CGTTCAGCTC CTGCCCTCAC    31320

CGCCCGAGCC CCCACGTGCC CCGCGCTGCC ACTGGCACCT TAATCAACTT CTCATCCCGC    31380

TCCACGTTGA TCTCTGCCGG GTTCCCTTCC TTAGGAGGCT CCTCAGGAGG AGCGCCCCCG    31440

CTGCTCCCCA GCAGCTCCTC CTCCTCGGCG CTTACTTCCT CGATCAGGTA GTCGGTGATA    31500

TTCTTCAAGA TCGGGTTTTG CGAGGGCAGG CTCTGATGGG AGGAAGAGAA GCAAGTAAGG    31560

CAGAGAAGAC CTTCAGAGGA GGTAACCTGA GACTTTCCAC AAGTGAAAGA GCAGCGAGGG    31620

GACAGGAGTT CACCGGACAT AAATGGCACC TTTTGCCCCC TTGAGATTTG TCTTTATTTT    31680

AGCTTTTGTT CCACCCCAGC CACAAATGAT CACTAGCATC CCCCCAGTTC TGCTGGAATC    31740

TGGAGGTGCT GCTACCCACA CACGAAGGGG CAAATGAGTG AGCAGGCGAG TGGGTGCAAG    31800

GGTTCAAGGC TACAGATAGG TAAGGTCAGA GGTGCCCACA GCAGAGGCAC TACCAGTTGC    31860

TTCTGACAAA GTCCTTTGGG GAGTCACTGA CCGTGGGCAG GGGAGGCGTC CCTGGTTCTG    31920

AGGCCCAAAG CTGTGTCCTG TCATCCAGCG TGTGGATCAG CTTGGCCGCC AGCTTGATGT    31980

CGTTGCGCAC AATCTGCTTG TGCTGGGTGA TGCCGTTGAT GTTGCGAACG CGCCGGGTCA    32040

GGTCCCTGTT CACACCAGGG CTCAGCTCAC ACTCCCGGAG CTGGAGGGCA GACATCATCA    32100

GCAGCTTACC CCACTTACCC CGCTTGCCAG AGAAACAGCA GCTCTAAGAC CCTTCCCTCT    32160

TGAGCACCAG CGATTGATCA GACTGCGAGC TCCCTGGGGA CGGGGACCAC ATAGGTTCCG    32220

TCCATGCTAA CGCCCTAGAG CCTTGCCCAG AGACAACGTA GCCAGACAAA ACGGTCAAAG    32280

AGTGTGCAGA ACAACCAAAC TATCAGATGA ACAAAGTCAC ACAGAGGTCC CGTGTGGCAC    32340

AGAGTCTCCC TTCCTCTTCC CCACAGTCCC ACCCCCAGCA CTCACACGGA TGTTCTGCAG    32400

GTTCCAACAG ATCTCTTTAA TGTTAACACT GCGGTCGAAG GTCACCCAGC CACGACGGAA    32460

AAACCTACAC AAGAAAGAAA ATGTTAGCAT AGTCAAGCGA GGGAGTTGGT GTTGGCCATT    32520

AACGTTCCCC TGCACTTTTC CCTCCAACGC ACCGAGTTAC TCACCTCCTC TCTGGCTGGG    32580

GCTCTGAGAG CGCCACCCGC ATAAAGCCTG GGTACCTTTT ACAAAGCTGC AAGAAGCAGA    32640

AAAGCAGCCC CACAGTGACT CAAGGATTCA TTCGCTTCTT CCTCCAATCC CCCACTGCCC    32700

TCAGAACCCT AGGGACTAAC TGCCTTATCA CTCTTCCCAT CCTTGGGCAG GGAAAAACCA    32760

CTAAAGGGCT TCAGAACACC AGCACCTGAA AGCCAATGGC GCTATCAGGA CTAGTCCTCG    32820

GAGGCCATGG AACCTGGGGA AGGGGCCTCC CTAGCAGGTG AAACGGGGGC ATCTGTCACA    32880

GGCAGGGCCC CACTGCCTTC CCTCTACCCT CCACTTCTCC ATCAGCCCTG CCCTGACTCC    32940

ACGGGTCCCC ACTCACGGAG ATGATCTCGG CCCGGGAGAT GTTGGGCGCG ATGTTGCGCA    33000

TGAAGAGGGA GCAGGTCTTA TGCAGCGGCC GCGGCTTGCA CTCCAGCCCC GCGGCGTCCT    33060

TGGGCTTCTC CCATTCTTCT TCCTTGGGCT TCTCCTTCTC CTTGAGCGCT TCTTCTAGGC    33120

AGGAAGGGGG GTAGGAAGGA GTTGGTGCAT TTTTATTACT GATTGTGGTG GGGAGGATAC    33180

AGAAGCTTTC CCCTAAAAGC CACCCACCCT CCCGTCAATG TCGCCAACCT CTCACCTCCC    33240

CACCCGCATT AGGAGAACGC ACTTTAAAGC AGAAAAGAAA CCCTACCGGC CTCCTCCTTC    33300

TCCTCCTCAG CCTGGCCGCT CTCTGACTCC GACTCAGACT CTGACACGCT GCCCTCGTCA    33360

AAGCTGTCGT CACCACTGTG CTTCCGGTTC CGCTTCTTGC TACTCTGTGT GAGCCACAGC    33420

AGAGGGGACA AGTCAGCGTG CCAGAACCCC AGCCCCAACA CTCTGACCCC AGGCCACAGA    33480

CACCTCACCT TTTTGGCTTC CTTCTCGGAG TCTTCTTTCT TCTCTTCCTT GTCCCCATCA    33540

CCCTCCGACT TCTTTGTTTT GTCATCATTA GAACTGTCAT TCTCAGCCTA TGGTAAGAGA    33600
```

-continued

```
CAACCACTGG GGATGTCAAA CCTCCCCTCC CACCTTTATC AGAGGGCCCC CACCCCCACA    33660

GCTGAGGCCA CAGGTTCATT TTCCCCAGCC CCCTACTTCT AGCTCCTATG GACCCCTACC    33720

CGCCCCCCTC CCCCAGGCTG CCAGGGACAA CACTAGGAGA CCCAGGGCTC GGACCTGCTT    33780

GCCGTCTTCC TTCTTCTCAT CCTTGTCGTT GGTTTTGCGC TCCCCGTCCC CTAGGCCTGC    33840

TCCAGCCCGT CCTTCTTCTT TCTTGCTGGG CTCCCCAGGC TTTCCTGCCT GCTCCTCCTC    33900

CTCCTCCTGC TCCAGGATGC GAAGATCATT CTCCGTGCCT CCTTCCATCT TAATCACGGC    33960

TACCAACAAA GGGAACAGAG GTCATGACCC CAGGGCCCTG GCTCCTGTCA ACCGGCTTCT    34020

ACCTGATCCC CAGACACCCC CACCCCCATG GGGCCCAGAT GCCTGCCACC CCTCCAAATC    34080

CGCACACCTG CATCCAGCAT CTTGACAATG GCATCAGCTT TGTCTATGTC CAGGAGAAGG    34140

TTATCAAACC AGCCAGTCTC CATGAGGGAC AGGAAGACCC TCAGTCGGTT TTGCAGGGCC    34200

CCCCGGGCCT CCTGCCGACG CTTCCCCACC TCATCTGGGT GGTACTTAGA CCGAAACCTG    34260

GGAACGAAGC GGGGGAGGGA AAGACAAAAC AGTTATTGGA AGCCAAGGCC AGGATGTGGG    34320

AAGGGGCCCA GGAAAGACAG GGCATATCCC CCTTCCTCTC ACAACCACAA AAGGTCATCA    34380

AAATAGAGAG ATTAAGGGAT AGGGGTGCGC TAGAACCACC CAACACCCCA AAAGGAACCA    34440

GAAGTTGTGT TCTGTGAAGA TTTGGGGGAG AACCAGGAAC TAAGAGCTCT GGATTTGGGA    34500

AGACCAATGA CTACAGGGGG ACGCCAGGGT AGGAGAGGCA GATTTACCAC TTTAAATCTC    34560

TGGGAAACAC TAACGTAGTA AAAAGGTGTC ATTTCCCAAA GCTTCAGAGA GGAAGGCTCA    34620

GGAAATAGCA GGCCCTGAAG AACCTCCCTC TCCTCACCAA CCCCAAACTG CAGTCATTCA    34680

AAAACTGCTC CCGCCAACTC CCTCCACCCC GAGGTGGAAG ACAGAGGGCC AGATAGCAAA    34740

AGCCCAGAGG CAGGGCACCT TTCTCCACCC GTGGGAAGAT AAGCAAGACG GTGAAGGGAC    34800

AGGAAAGACC GAAGGGAGAC ACTGGAGTGC CCTTTAGAGC CTCAGGTCCT GCCCACAGGG    34860

GGAGAGAGAG GAGAGGGCTG GAAGGTTAGG GAGAAGAAAA ATAAAACATT TCAAATAGGA    34920

CCTCAGAGGG AAAACAGAAG AAATGAGGAG TATGAGGAAA AGGGGAAAGG GAGGAAAGGG    34980

GAGAGTGTGA GAAAGTCCCA GAAACCGAAA ACAAAGGGAA AAACTAAAGA TCCTAAGCTT    35040

GGGTCTCCCT ATAGTGAGTC                                                35060
```

TRANSGENIC ANIMAL ASSAY SYSTEM FOR ANTI-CHOLINESTERASE SUBSTANCES

This application is a Continuation-In-Part of U.S. Ser. No. 08/370,156 filed Jan. 9, 1995 now U.S. Pat. No. 5,932, 780 which is a Continuation-In-Part of U.S. Ser. No. 08/202, 755 filed Feb. 28, 1994 now abandoned and U.S. Ser. Nos. 60/031,194 filed Nov. 20, 1996, 60/035,266 filed Dec. 12, 1996 and Provisional Application filed Feb. 13, 1997.

GRANT REFERENCE

Research in this application was supported in part by U.S. Department of the Army Contract DAMD17-86-C-6010. The U.S. Government has a nonexclusive, nontransferable, irrevocable paid-up license to practice or have practiced this invention for or on its behalf as provided by the terms of Contract DAMD17-86-C-6010 awarded by the U.S. Department of the Army.

FIELD OF THE INVENTION

The present invention is generally in the field of cholinesterase enzymes and assays for anti-cholinesterase substances. More specifically, the present invention concerns new human acetylcholinesterase (AChE) encoding DNA sequences and use of these AChE sequences to provide transgenic animals which are capable of expressing human AChE, and which can be used to assay the effects of various anti-cholinesterase substances in vivo.

BACKGROUND OF THE INVENTION

Humans have two genes that encode acetylcholine-hydrolyzing enzymes, AChE and BChE (Soreq and Zakut, 1993). The ACHE and BCHE genes, although drastically different from each other in base composition, are thought to be derived from a common ancestral gene. ACHE, mapped to chromosome 7q22 encodes the primary enzyme, acetylcholinesterase (AChE, E.C. 3.1.1.7), which terminates neurotransmission at synapses and neuromuscular junctions. BCHE, mapped to 3q26 encodes butyrylcholinesterase (BChE or alternatively BuChE, E.C. 3.1.1.8), a homologous serum esterase with somewhat broader substrate specificity. BuChE acts as a scavenger of natural and man-made poisons, including organophosphate and carbamate pesticides, that are increasingly a threat to human health (Loewenstein et al., 1993). Yet, individuals with no BuChE activity (silent phenotype) in their serum are apparently healthy.

The book *Human Cholinesterases and Anticholinesterases* by Soreq and Zakut (Academic Press, Inc., 1993) provides a summation of the biochemical and biological background as well as the molecular biology of human cholinesterase genes. The book in its entirety is incorporated herein by reference. Further, the book *Transgenic Xenopus* by Seidman and Soreq (Humana Press, 1996) provides a summation of the development of the Xenopus transgenic animal model. The book in its entirety is incorporated herein by reference.

Briefly, AChE acquires heterogeneous properties in different tumors distinct from those it displays in muscle and nerve, hemopoietic cells, embryonic tissue and germ cells. Monomers of the catalytic AChE subunit were observed in meningiomas and tetrameres in glioblastomas. Inhibition properties different from those of normal AChE were determined for serum AChE in various carcinomas. Moreover, tumorigenic expression of the corresponding ACHE gene was found to be subject to variable control mechanisms. In differentiating neuroblastoma cells, inhibition of mevalonate synthesis, which decreases proliferation rates, increases AChE levels. In PC12 cells, in contrast, nerve growth factor induces the production of hydrophilic AChE, while embryonal, carcinoma cells and thyroid tumor cells produce this enzyme under all conditions examined.

A major hydrophilic form of AChE with the potential to be "tailed" by non-catalytic subunits is expressed in brain and muscle whereas a hydrophobic, phosphoinositide (PI)-linked form of the enzyme is found in erythrocytes. Two sublines of the human erythroleukemic K-562 cells were shown to express the PI-linked form of AChE, however, with different structural properties of the PI moiety. To reveal the molecular mechanisms underlying the heterogeneous tumorigenic expression of AChE, applicants initiated the investigation of alternative splicing in AChEmRNAs from different tumor cells.

Alternative splicing controls the generation of proteins with diverse properties from single genes through the alternate excision of intronic sequences from the nuclear precursors of the relevant mRNAs (Pre-mRNA). It is known to be cell type-, tissue- and/or developmental stage-specific and is considered as the principal mechanism controlling the site(s) and timing of expression and the properties of the resultant protein products from various genes.

Alternative exons encoding the C-terminal peptide in AChE were shown to provide the molecular origins for the amphiphilic (PI)-linked and the hydrophilic "tailed" form of AChE in Torpedo electric organ. The existence of corresponding alternative exons and homologous enzyme forms in mammals suggested that a similar mechanism may provide for the molecular polymorphism of human AChE. However, the only cDNAs reported to date from mammalian brain and muscle encode the hydrophilic AChE form. Nonetheless, RNA-protection and PCR analyses have demonstrated the existence of two rare alternative AChEmRNAs in mouse hemopoietic cells.

More specifically, three alternative AChE-encoding mRNAs have been described in mammals. The dominant brain and muscle AChE found in NMJs (AChE-T) is encoded by an mRNA carrying exon E1 and the invariant coding exons E2, E3, and E4 spliced to alternative exon E6. AChEmRNA bearing exons E1–4 and alternative exon E5 encodes the glycolipid phosphatidylinositol (GPI)-linked form of AChE characteristic of vertebrate erythrocytes (AChE-H). An additional readthrough mRNA species retaining the intronic sequence I4 located immediately 3' to exon E4 was reported in rodent bone marrow and erythroleukemic cells and in various tumor cells lines of human origin (FIGS. 1A and 1B).

AChE is accumulated at neuromuscular junctions (Salpeter 1967) where it serves a vital function in modulating cholinergic neurotransmission (Reviewed by Soreq and Zakut, 1993).

Anti-cholinesterase drugs are employed to treat a variety of diseases including Alzheimer's and Parkinson's diseases, glaucoma, multiple sclerosis, and myasthenia gravis (reviewed in Millard and Broomfield). As a brief summary, glaucoma is a leading cause of blindness. Several different kinds of glaucoma exist, but the most common is primary open-angle glaucoma (POAG). Because little is known conclusively about the etiology of this disease, present medical treatment is purely symptomatic. For at least thirty years, ophthalmologists have been treating advanced POAG with anti-ChE compounds. The most often-used has been echothiophate; other agents have included DFP, neostigmine, physostigmine, paraoxon and tetraethylpyrophosphate (TEPP).

Physostigmine was first reported to mitigate the autoimmune disease, myasthenia gravis (MG), and provided the basis of a diagnostic test that enabled detection of moderate forms of the disease. This work was the impetus for uncovering the cause of organophosphorus nerve agent toxicity and, sixty years later, quaternary carbamate compounds, such as neostigmine and pyridostigmine, are still used in the symptomatic treatment of MG to provide increased neuromuscular transmission and, to some extent, greater muscular strength. Edrophonium, a reversible anti-ChE, also improves MG by compensating for reduction of ACh receptors through elevation of neurotransmitter levels.

Senile demential of Alzheimer type (SDAT) is one of the most common causes of mental debilitation among the elderly. SDAT coincides with selective degeneration of basal forebrain cortical cholinergic neurons and "neurofibrillary tangles" contain both AChE and BuChE activity. Brain AChE activity apparently is reduced in SDAT, a form of cholinergic imbalance. Several reports of specific reductions and increases in different brain AChE isoforms, as well as an abnormal SDAT-associated cerebrospinal fluid AChE isoelectric point variant have been reported. Because of the general destruction of normal presynaptic cholinergic fibers in SDAT, however, local changes in AChE may be quite distal to the cause of injury.

It has been suggested that a procedure to counter SDAT symptoms would be the inhibition of AChE to allow diffusion of ACh to become the rate limiting step of synaptic transmission and, hence, to conserve selectively the "functional" transmitter released. Thus, anti-ChEs would compensate for the diminished ACh released by the surviving cortical neurons. There was initial success in improving SDAT with arecoline and physostigmine but the latter was not sufficient to counteract completely the side-effects of inhibition. 1,2,3,4,-tetrahydro-9-aminoacridine (tacrine) has emerged as a candidate, but it is premature to conclude proof of efficacy and it is possible that it acts by stimulating ACh synthesis, as well as by inhibiting ChEs.

Furthermore, anti-cholinesterase poisons form a broad category of agricultural and household pesticides including organophosphorous and carbamate agents. There are reports of individual sensitivity to these agents and screening methods are needed to determine the safety of the agents.

Retinal photoreceptor degeneration (RD) is the most common symptom of retinitis pigmentosa, a group of inherited human blindness disorders displaying both genetic and phenotypic diversity (reviewed in Shastry, 1994). While little is known about the etiology of RD, progress in understanding this heterogenous disorder has been aided considerably by the utilization of both naturally occurring and transgenic animal strains with known distinct genomic defects, which display retinal degeneration analogous to human RD (Mullen and LaVail, 1976; Pittler and Baehr, 1991; Connell et al., 1991; Sung et al., 1994). Most of these strains carry mutated key proteins that are directly involved in the phototransduction pathway (Humphries et al., 1992). However, it is currently estimated that only 30% of the human RD patients carry mutated phototransduction proteins (Shastry, 1994). This, in turn, raises the question whether other mechanism(s) exist which explain the occurrence of RD with unknown genomic origins. Because of the known association between cholinergic imbalance and neurodeterioration (Bierer et al., 1995), applicants explored the possibility of cholinergic involvement and possible imbalance in RD.

Research and development directed toward the production of new specific, effective, low-toxicity anti-cholinesterase drugs and insecticides are abundant. However, heretofore, no effective in vivo system has been developed which would allow for the rapid, effective and reliable screening of such anti-cholinesterase substances. Applicants have developed a transgenic animal assay system as disclosed in co-pending U.S. Ser. No. 08/370,156 assigned to the same assignee and incorporated herein by reference. Additionally, the book *Transgenic Xenopus* by Seidman and Soreq (Humana Press, 1996) provides a summation of the development of the Xenopus transgenic animal model and Beeri et al. (1994) and Beeri et al. (1995) provide a information on the development of the transgenic mouse model.

However, in developing transgenic models carrying human genes it is useful to have the gene under the human promoter. Examples from other genes demonstrate transcriptionally important regions at distances up to 40 kb from the transcription initiation site (e.g. serum albumin). In the previous studies and in Examples herein below Applicants used the 596 bp region immediately adjacent to the transcription initiation site in the human ACHE gene (Soreq, et al., 1990; Ben Aziz-Aloya et al, 1992). As indicated in the Examples, data shows that the 596 bp partial human promoter appears to be sufficient for directing persistent CNS transcription and therefore useful in establishing transgenic animal models. However, it does not induce AChE production in other tissues (Beeri et al., 1995) or direct developmental variations in the intensity of CNS expression of ACHE. Therefore, it would be useful to isolate an additional promoter to use in the transgenic assay system.

SUMMARY OF THE INVENTION

The present invention provides a transgenic animal assay system which provides a model system for testing for, and treatment of, cholinergic deficits and imbalances in mammals such as cognitive functioning in Alzheimer's patients, certain types of retinal photoreceptor degeneration, hematopoietic disorders, and screening for and susceptibility to anti-cholinesterase compounds.

The present invention provides a recombinant expression vector comprising a DNA sequence encoding a heterologous cholinesterase (ChE) enzyme and promoter. The heterologous cholinesterase (ChE) enzyme can be normal human AChE; normal human BChE; naturally-occurring variants of the AChE and BChE; synthetic variants of the AChE and PChE, the synthetic variants selected from recombinantly-produced point-mutated and deletion, of one or more residues, mutations; and normal insect ChEs.

For human AChE or biologically active derivatives thereof the ACHE gene can be a DNA sequence which has all or part of the nucleotide sequence substantially as depicted in SEQ ID NO:1, and which encodes an amino acid sequence substantially similar or identical to all or part of the sequence of amino acid residues depicted in SEQ ID NO:2; a DNA sequence which has all or part of the nucleotide sequences substantially as depicted in SEQ ID NO:3, and which encodes an amino acid sequence substantially similar or identical to all or part of the sequence of amino acid residues set forth in SEQ ID NO:4; or a DNA sequence which has all or part of the nucleotide sequence substantially as depicted in SEQ ID NO:5, and which encodes an amino acid sequence substantially similar or identical to all or part of the sequence of amino acid residues set forth in SEQ ID NO:6.

The promoter controlling the transcription of the sequence encoding ChE is a eukaryotic host cell compatible promoter such as CMV, CMV-like, ACHE and ACHE-like promoters. In a preferred embodiment for the human ACHE gene, the promoter is a human promoter as set forth in SEQ ID No:7.

The present invention provides eucaryotic cells, transgenic animals and progeny thereof transformed with the recombinant expression vector of the present invention. The animals can be Xenopus or mice.

BRIEF DESCRIPTION OF THE DRAWINGS

FIG. 4 is a schematic depiction presents two DNA constructs with restriction sites, CMV-ACHE and HpACHE, used to prepare transgenic mice, as described in Example 1;

FIG. 5 shows a schematic representation of transformation procedures to prepare transgenic mice and representation of blot hybridization results obtained from transgenic mice, as described in Example 1;

DETAILED DESCRIPTION OF THE INVENTION

The present invention is based on the surprising and unexpected findings, as detailed herein below, that it is possible to obtain transgenic animals, e.g. mice and Xenopus embryos, that are capable of expressing human cholinesterases (e.g. AChE) in substantial amounts. Accordingly, these transgenic animals can be employed for the rapid and efficient screening in vivo of anti-cholinesterase substances. Further the transgenic animals provide a model for testing of treatments for disorders with imbalanced cholinergic signaling.

The system allows the determination if anti-cholinesterase substances such as organophosphates, carbamates, anti-cholinesterase drugs, snake venoms, plant glycoalkaloids, etc. are:

(i) potentially harmful to normal individuals;

(ii) potentially useful as therapeutic agents in anti-cholinesterase indications; and (iii) capable of being scavenged or blocked by modified (natural or synthetic variants) human AChEs or BChEs.

This system provides for testing of new AChEs or BChEs that may be used therapeutically for treating individuals exposed to dangerous levels of anti-cholinesterase substances/toxins and where their own endogenous AChEs or BChEs cannot effectively block such toxins.

Additionally, the present invention would provide for testing of new AChEs or BChEs that will scavenge or block drugs of abuse such as cocaine, heroin and morphine.

The model system also provides for testing of treatments of disorders with imbalanced cholinergic signaling including dementias of the Alzheimer type, hematopoietic disorders and retinal photoreceptor degeneration disorders.

The model system utilizes transgenic animals and progeny thereof. The present invention provides the following transgenic animals:

(i) A transgenic animal having a recombinant DNA expression vector encoding a heterologous cholinesterase (ChE) enzyme selected from the group consisting of:

(a) normal human AChE;
(b) normal human BChE;
(c) naturally-occurring variants of the AChE and BChE of (a) and (b);
(d) synthetic variants of the AChE and BChE of (a) and (b), the synthetic variants selected from recombinantly-produced point-mutated and deletion, of one or more residues, mutations; and
(e) normal insect ChEs,
with the transgenic animal being capable of expressing substantial amounts of the ChE enzyme;

(ii) A transgenic animal of the invention as noted above which has a recombinant expression vector encoding a human AChE or biologically active derivatives thereof selected from:
(a) a DNA sequence which has all or part of the nucleotide sequence substantially as depicted in SEQ ID NO:1, and which encodes an amino acid sequence substantially similar or identical to all or part of the sequence of amino acid residues depicted in SEQ ID NO:2;
(b) a DNA sequence which has all or part of the nucleotide sequences substantially as depicted in SEQ ID NO:3, and which encodes an amino acid sequence substantially similar or identical to all or part of the sequence of amino acid residues set forth in SEQ ID NO:4; and
(c) a DNA sequence which has all or part of the nucleotide sequence substantially as depicted in SEQ ID NO:5, and which encodes an amino acid sequence substantially similar or identical to all or part of the sequence of amino acid residues set forth in SEQ ID NO:6;

(iii) A transgenic animal of the invention as noted above in which the recombinant expression vector contains a promoter controlling the transcription of the sequence encoding AChE selected from the group of eukaryotic host cell compatible promoters consisting of CMV, CMV-like, ACHE and ACHE-like promoters. More particularly, the preferred promoter is the human AChE promoter has a sequence as set forth in SEQ ID No:7.

As described herein, the present invention provides for transgenic gene and polymorphic gene animal and cellular (cell lines) models as well as for knockout models. These models are constructed using standard methods known in the art except as noted herein and as set forth in U.S. Pat. Nos. 5,487,992, 5,464,764, 5,387,742, 5,360,735, 5,347,075, 5,298,422, 5,288,846, 5,221,778, 5,175,385, 5,175,384,5, 175,383, 4,736,866 as well as Burke and Olson (1991), Capecchi (1989), Davies et al. (1992), Dickinson et al. (1993), Huxley et al. (1991), Jakobovits et al. (1993), Lamb et al. (1993), Pearson and Choi (1993), Rothstein (1991), Schedl et al. (1993), Strauss et al. (1993). Further, patent applications WO 94/23049, WO 93/14200, WO 94/06908, WO 94/28123 also provide information.

The present invention provides an isolated substantially pure DNA having a sequence encoding acetylcholinesterase (AChE) selected from the group consisting of:

(a) genomic clones having a nucleotide sequence derived from the genomic region of a human AChE gene;
(b) cDNA clones having a nucleotide sequence derived from the sequence of the genomic clones of (a);
(c) DNA sequences capable of hybridization to the clones of (a) and (b) under moderately stringent conditions and which encode biologically active AChE; and
(d) DNA sequences which are degenerate as a result of mutations to the genetic code of the DNA sequences defined in (a), (b) and (c) and which encode biologically active AChE.

Preferred embodiments of the above DNA sequence of the invention are:

(i) a DNA sequence of the invention as noted above wherein the sequence encodes human AChE or biologically active derivatives thereof;
(ii) a DNA sequence of the invention as noted above which has all or part of the nucleotide sequence substantially as set forth in SEQ ID NO:1, and which encodes an amino acid sequence substantially similar or identical to all or part of the sequence of amino acid residues set forth in SEQ ID NO:2;
(iii) a DNA sequence of the invention as noted above which has all or part of the nucleotide sequences substantially as set forth in SEQ ID NO:3, and which encodes an amino acid sequence substantially similar or identical to all or part of the sequence of amino acid residues set forth in SEQ ID NO:4; and
(iv) a DNA sequence of the invention as noted above which has all or part of the nucleotide sequence substantially as set forth in SEQ ID NO:5, and which encodes an amino acid sequence substantially similar or identical to all or part of the sequence of amino acid residues also set forth SEQ ID NO:6.

The present invention also provides as a preferred embodiment recombinant expression vectors containing any of the above-mentioned DNA sequences of the invention. The recombinant vectors may be any of the well-known eukaryotic expression vectors, and their construction is by any of the standard recombinant DNA (genetic engineering) procedures, such vectors and procedures now being standard to all skilled practitioners. Further, the promoters used in the above vectors to control transcription of the AChE encoding sequences, may also be any of the well-known eukaryotic host cell-compatible promoters (e.g. animal virus, yeast, mammalian promoters). The preferred promoters are the CMV, CMV-like, human AChE and human AChE-like promoters having similar transcription factor binding sites within the promoter region sequence. More particularly, the preferred promoter is the human AChE promoter having a sequence as set forth in SEQ ID No:7.

Another preferred embodiment of the invention is a eukaryotic host cell transformed by any of the above recombinant vectors of the invention and progeny thereof, the host cell being capable of producing (expressing) AChE under suitable culture conditions. Here too, the host cells may be any of the well-known eukaryotic cultured cell lines e.g. yeast, Chinese hamster ovary, etc. The culture conditions for such host cells are the standard well elaborated ones, with standard modifications, if necessary, to ensure that when high levels of AChE are expressed, this will not lead to substantial cell death.

The vectors can be introduced into cells or tissues by any one of a variety of known methods within the art. Such methods can be found as generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), and include, for example, stable or transient transfection, lipofection, electroporation and infection with recombinant viral vectors.

Additional features can be added to the vector to ensure its safety and/or enhance its therapeutic efficacy. Such features include, for example, markers that can be used to negatively select against cells infected with the recombinant virus. An example of such a negative selection marker is the TK gene that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

Figure 1A:
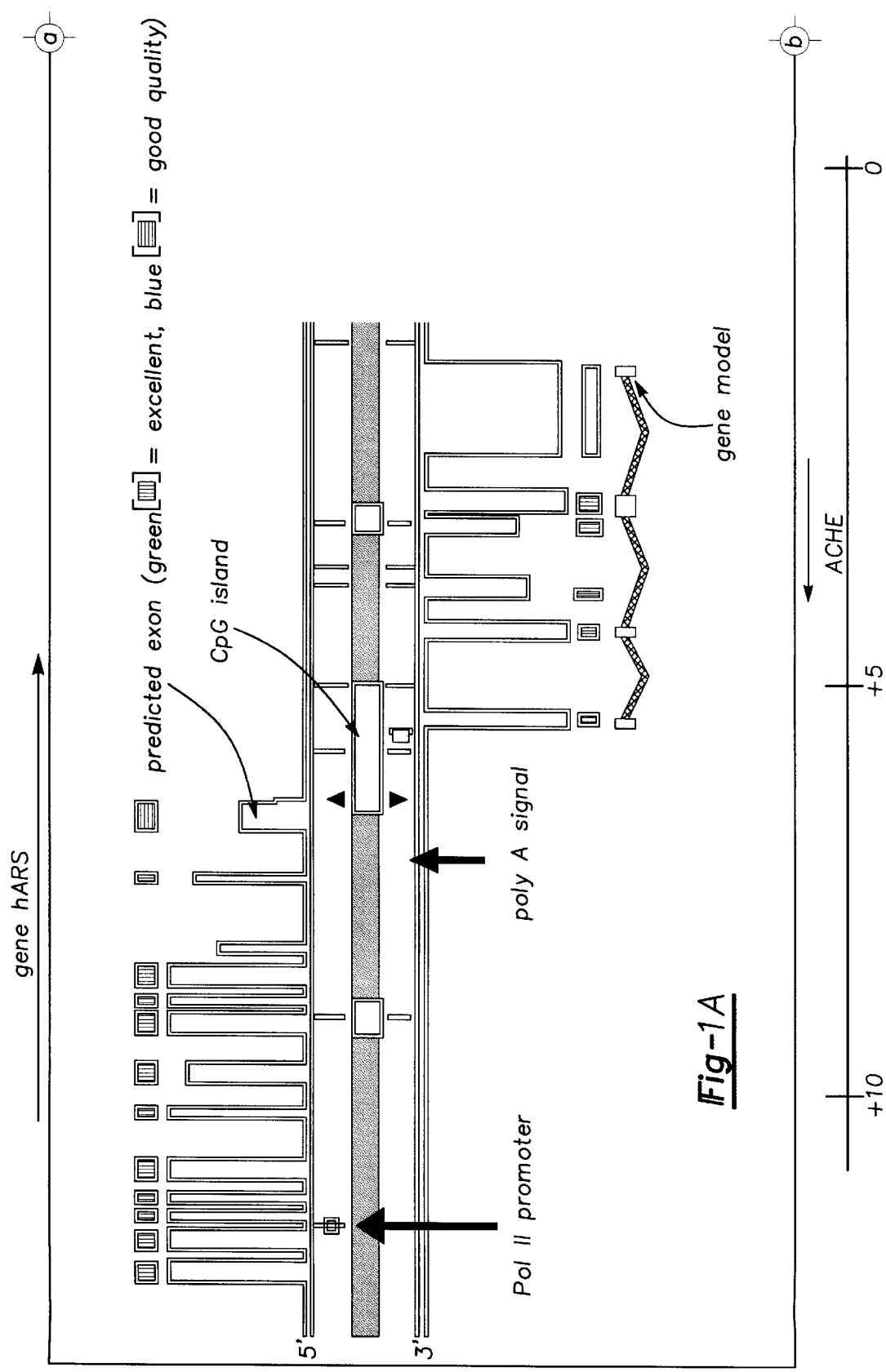
FIGS. 1A,B are schematic diagrams of the human AChE gene and the differently spliced mRNA products.
Figure 1B:
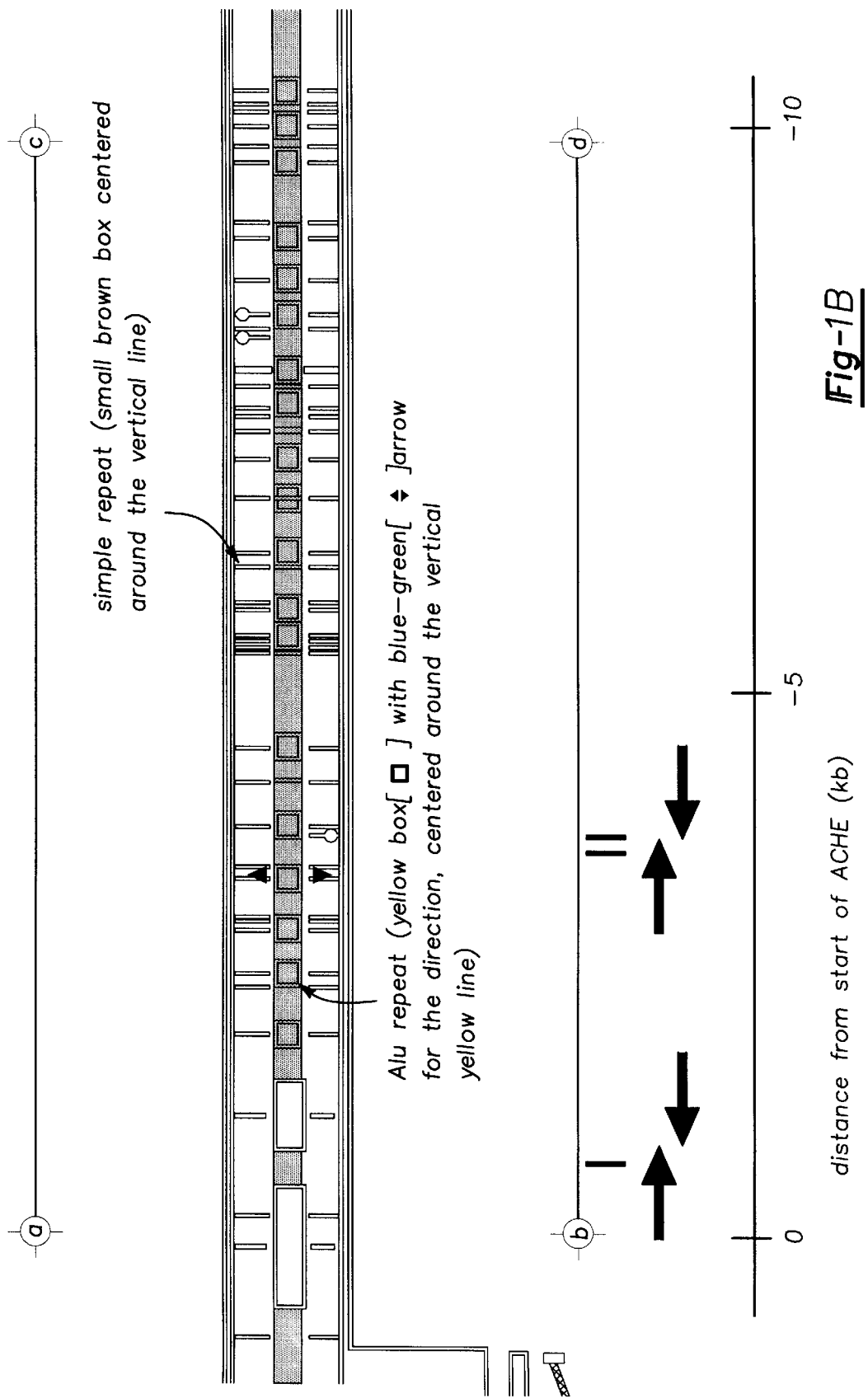
Figure 2:
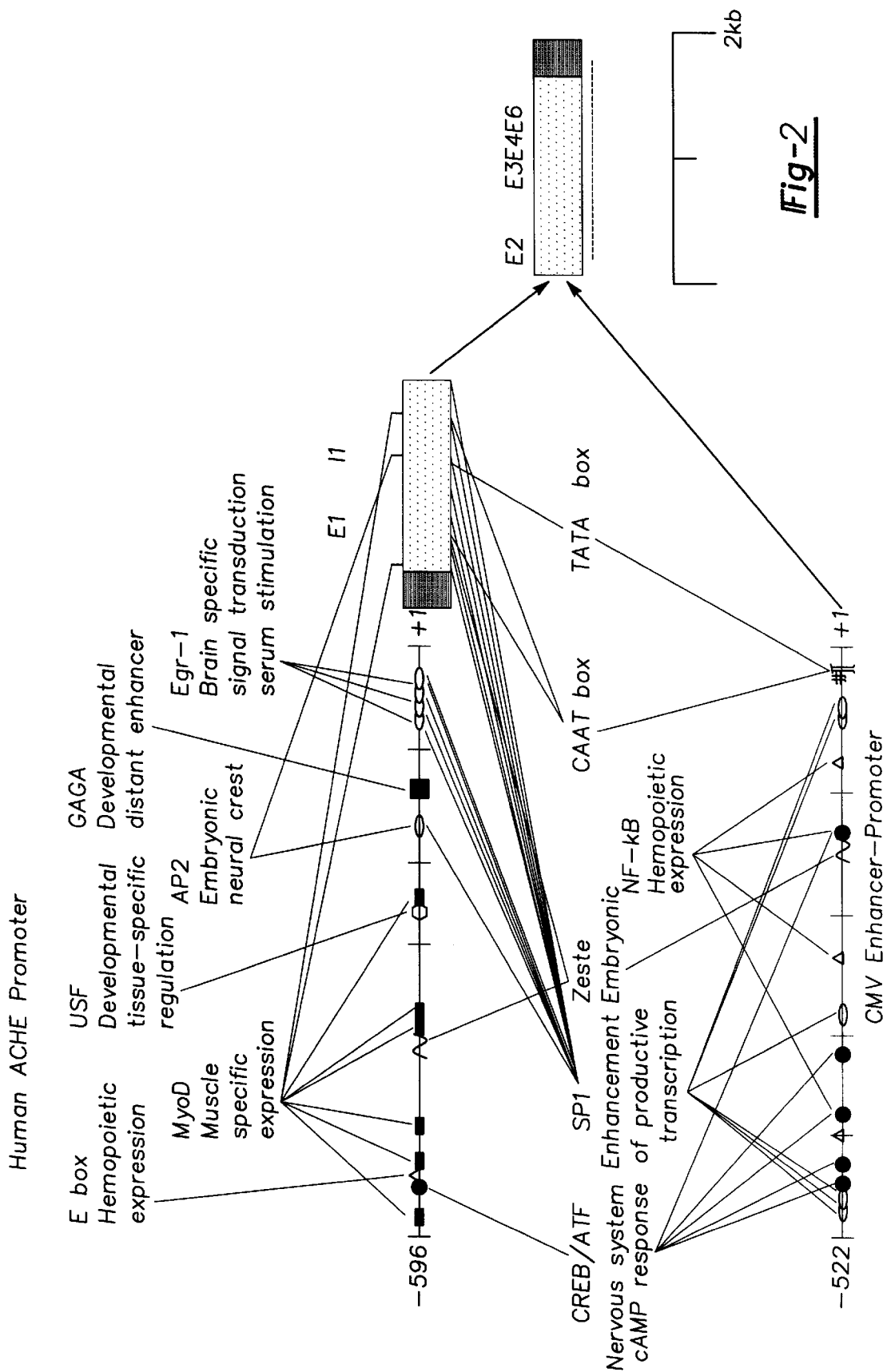
FIG. 2 is a schematic comparison of the human ACHE and the CMV sequences used for AChE production initially in transgenic mice, wherein sequences of the two promoters are presented with schematic localizations of the consensus transcription site binding motifs, sites common to both promoters are presented in the middle, sequences unique to HpACHE are shown on top, for details of each of these motifs, see Ben Aziz-Aloya et al., (1993)

The Examples establish and characterize the transgenic animal assay system of the present invention which provides for determining the anti-cholinesterase activity of substances selected from the group consisting of: organophosphates, carbamates, anti-cholinesterase drugs, plant glycoalkaloids and snake venoms, and comprises a transgenic animal of the invention as noted above. The preferred transgenic animals are Xenopus embryos (Seidman and Soreq, 1996) and mice. In general, two constructs encoding the brain and muscle form of human AChE (Ben Aziz-Aloya et al., 1993) were employed for microinjecting mouse eggs. One of these included the potent ubiquitous promoter of cytomegalovirus (CMV) (Schmitt et al., 1990) and the other a 596 nucleotide long fragment from the authentic promoter of the human ACHE gene, followed by its first intron and the same coding sequence (HpACHE). FIG. 2 presents these two DNA sequences and the transcription factor binding sites identified in them. The present invention further provides in addition to the 596 nucleotide long fragment of the human promoter, the human ACHE promoter as set forth in SEQ ID No:7.

In this transgenic assay system, either Xenopus or mice can be used, mice being advantageous because of their closer relationship, physiologically, to humans. However, Xenopus embryos are advantageous in that mature eggs of *Xenopus laevis* are readily fertilized in vitro. Owing to their large size and resilience, Xenopus eggs are easily manipulated and have proven amenable to a variety of experimental manipulations, including heterologous gene expression through microinjection protocols (see Seidman and Soreq, 1996, for detailed methods). Briefly, fertilized eggs develop rapidly to yield a tailbud embryo with a functional neuromuscular system within 48 hours. By day 3 post-fertilization (PF), reflexive swimming is observed, and continued embryonic development gives rise to a free-swimming tadpole 4–5 days PF. Two-three day old Xenopus embryos can already be exposed to the anti-cholinesterase substances to be tested. Thus, the rapid development of the neuromuscular system in Xenopus makes it an excellent in vivo model for the study of vertebrate myogenesis and synaptogenesis.

Applicants have previously cloned a DNA sequence encoding human AChE and used it to express catalytically active AChE in microinjected Xenopus oocytes and cultures human cells. Placed downstream of either the native human AChE gene promoter or the cytomegalovirus (CMV) enhancer-promoter and introduced into fertilized Xenopus eggs, this DNA led to overexpression of AChE in NMJs of two-day old embryos (Ben Aziz-Aloya et al., 1993).

In contrast to the above mentioned, the present invention concerns the cloning and expression in transgenic Xenopus embryos of constructs encoding the various alternatively spliced recombinant human AChE (rHAChE) of the invention, and also the cloning and expression of AChE in animals in the transgenic assay system of the invention. Moreover, the persistence of the overexpressed rHAChE enzyme in Xenopus neuromuscular junctions (NMJs) has also been shown, in accordance with the present invention, to persist to at least day 3 of embryonic development (Seidman and Soreq, 1996).

The present inventors have also cloned the natural variants of the BChE gene into Xenopus and have prepared site-directed mutants of this gene, also cloned into Xenopus (Seidman and Soreq, 1996). Thus, a very wide range of DNA constructs encoding natural and synthetic (e.g. site-directed mutants, truncated e.g. active fragments, alternatively spliced) human AChEs and BChEs can be prepared by the methods set forth in Seidman and Soreq, 1996, to prepare transgenic Xenopus embryos and as set forth herein below for mice. These transgenic animals may then be used for screening anti-cholinesterase substances, to determine:

(i) the toxicity of such substances if such are intended, for example, for use as pesticides;

(ii) the effectivity and specificity of anti-cholinesterase drugs intended for treatment of various diseases; and (iii) whether various natural or synthetic AChEs or BChEs (or active fragments thereof) may be more useful than others as agents for treating individuals exposed to toxic levels of anti-cholinesterase substances.

Moreover, the present inventors (see Ben Aziz-Aloya et al., 1993) analyzed the 596 bp human ACHE promoter in detail and have discovered a large number of transcription control sites within this promoter region (FIG. 2). Accordingly, by use of this promoter in DNA constructs encoding the above AChEs, it is possible in the transgenic animals, also to determine whether substances can affect AChE expression at the level of transcription, i.e. whether the observed inhibition is via inhibition of the enzyme itself or the production of the enzyme.

Applicants have further determined that the 596 bp human ACHE promoter sufficed to induce AChE accumulation in Xenopus NMJs. When it was inserted into the genome of transgenic mice, expression was particularly prominent in the CNS (Beeri et al., 1995). However, this observation called for extension of this promoter. The proximal 596 bp of this promoter were cloned by Ben Aziz-Aloya et al. (1993), but consensus motifs for binding transcription factors which are specific to some of the tissues where AChE is produced (e.g. hematopoietic) were not found. Applicants therefore continued by cloning and sequencing this promoter in order to improve and control human AChE gene expression in transgenic animals.

To this end, Applicants utilized a genomic clone (20 Kb) carrying the ACHE gene to screen a chromosome 7q cosmid library. Two cosmids were positive for ACHE. PCR analysis revealed that one of those carried the ACHE upstream domain.

Figure 3A:
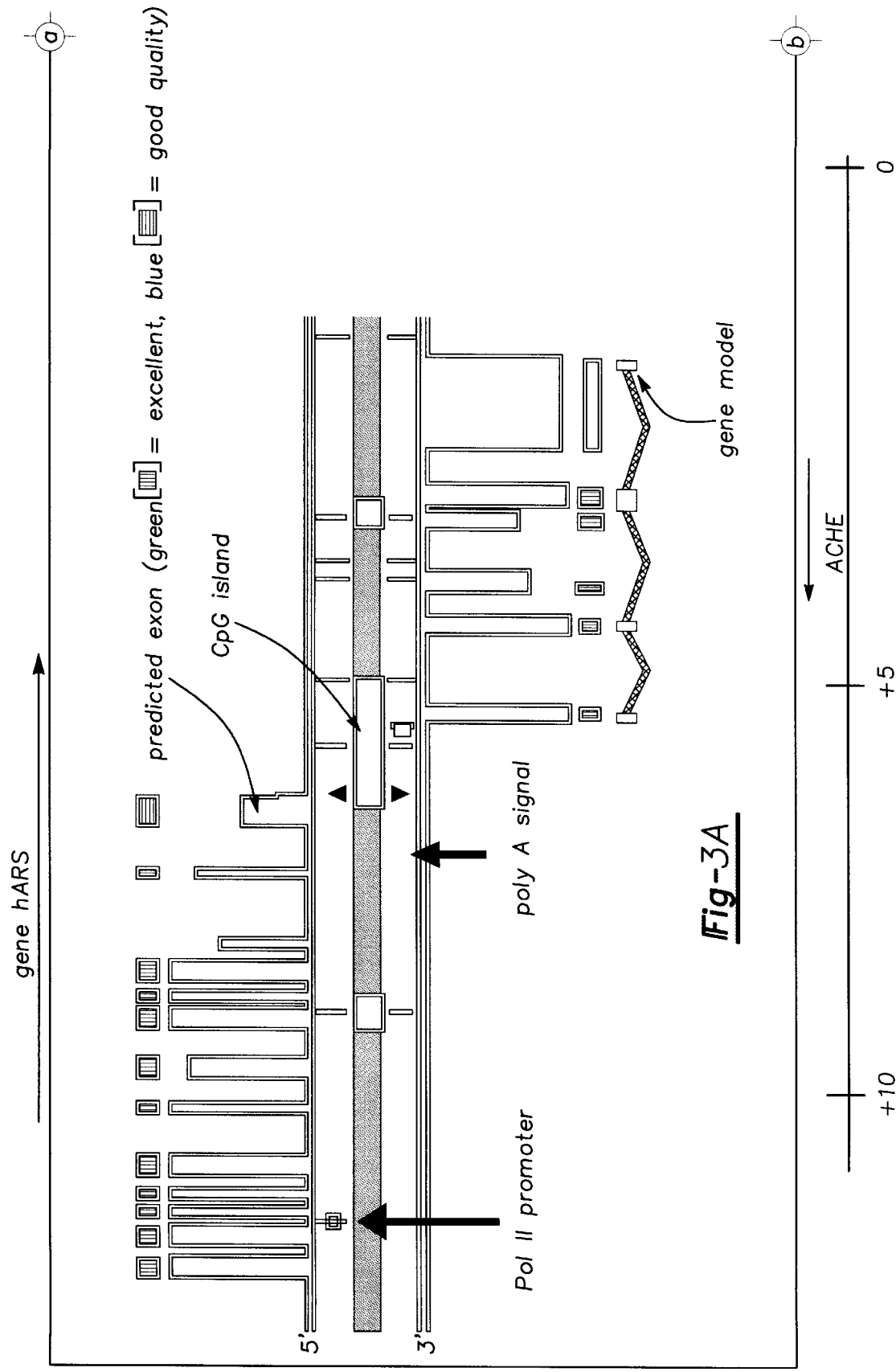
FIGS. 3A–C is a schematic depiction of the 35 kB cosmid (chromosome 7q22 cosmid)
Figure 3B:
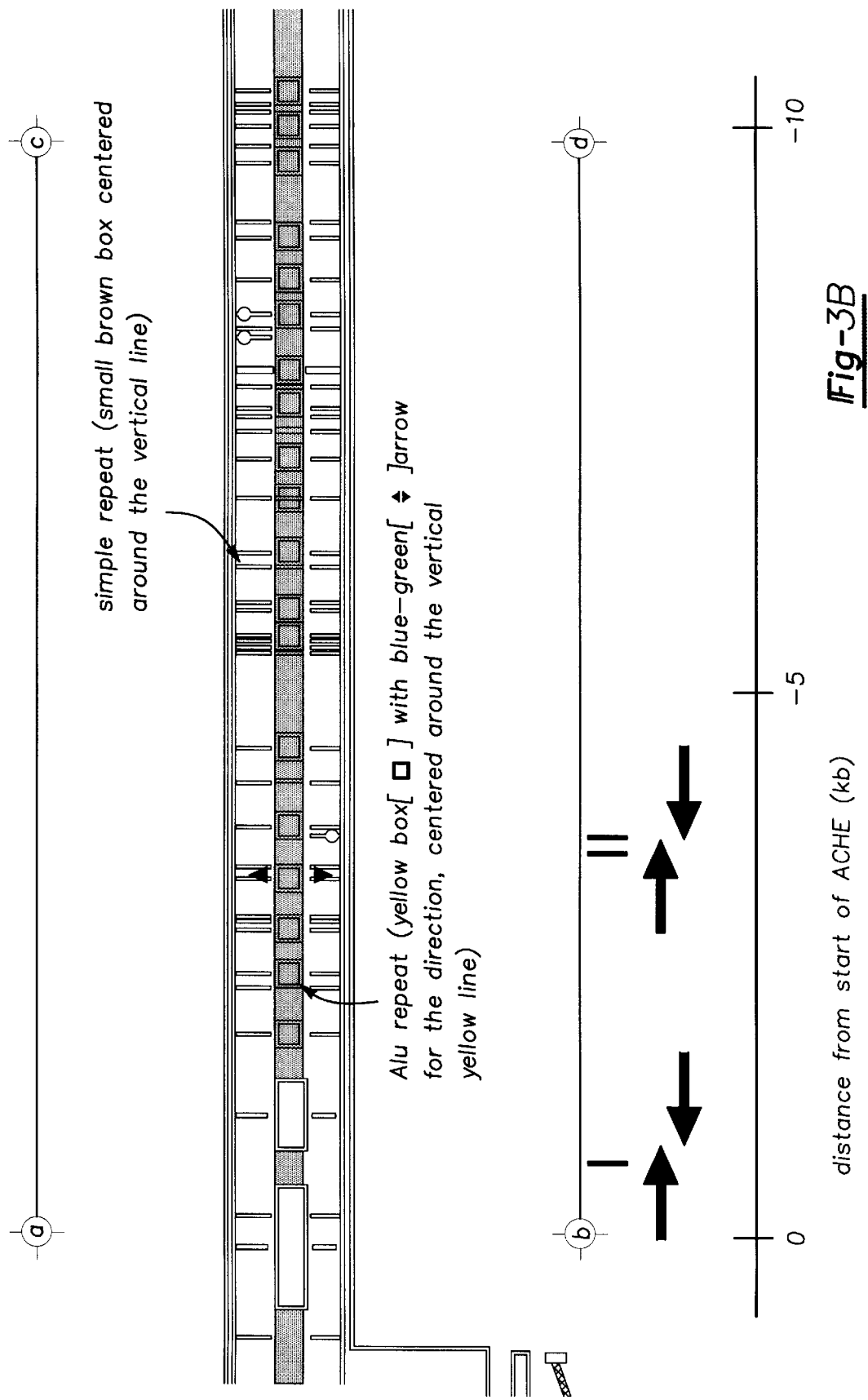
Figure 3C:
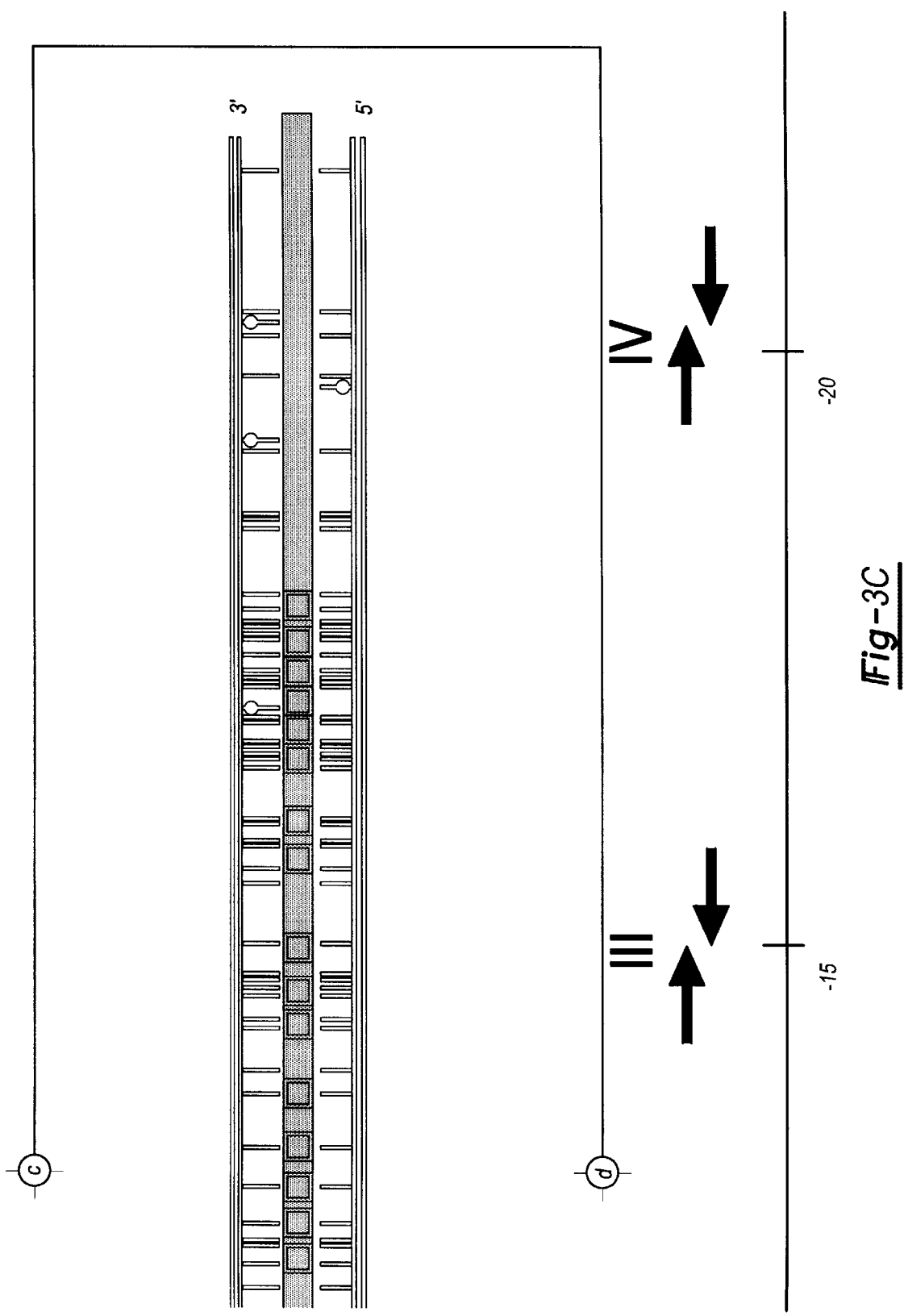

This cosmid (a total of 35 kb) was subjected to shotgun cloning and automated DNA sequencing (SEQ ID No:7 and FIG. 3). Referring to FIG. 3, starting from the 5' end of the lower DNA strand is the extended AChE promoter (approximately first 20,000 bases in SEQ ID NO:7) having many simple repeats (verticle lines) and Alu repeats. The ACHE gene follows (indicated by gene mode and lines showing exons). SEQ ID Nos:1,3 and 5 provide the alternative spliced sequences of the exons. The cosmid next has a CpG island. On this strand please note the poly A signal and the Pol I promoter continuing in the 3' direction. The sites indicated by I–IV are unique PCR primer sites for the extended ACHE gene promoter.

Unexpectedly a sequence for a gene conferring arsenite resistance was also found within the cosmid (SEQ ID No:7, last approximate 5 kb). Referring to FIG. 3, this gene is shown on the upper DNA strand (starting at left 5' end) and the exons are indicated. The polyA signal appears to be a possible alternative promoter for the arsenite resistance gene. The sequence was searched in GENEBANK and a partial sequence was reported however, this partial sequence has an incorrect initiation signal.

Furthermore, it is now possible by selecting the appropriate promoter to analyze substances, i.e. various transcription-initiation factors, which can induce AChE production by increasing the levels of transcription, i.e. substances which bind to the promoter and cause increased transcription of the ACHE gene. Such substances will therefore be useful as agents for treating individuals exposed to dangerous levels of anti-cholinesterase substances.

The assay system can also be used for determining the scavenging activity of natural and synthetic variants of human AChE and BuChE for abused drugs such as cocaine, heroin and morphine. BuChE has been shown in vitro to hydrolyze the methyl ester bond of cocaine and its derivatives (Isenschmid et al., 1989; Gatley, 1991). In vivo, in contrast to cytochrome P-450-catalyzed destruction of cocaine, which produces hepatotoxic norcocaine nitroxide, BuChE-catalyzed hydrolysis of cocaine generates innocuous products. The serum levels of BuChE, too, as modulated by ChE inhibitors, correlate with serum levels of cocaine and related narcotics (Kambam et al., 1992) and with their physiological effects (Kambam et al., 1993). This clearly indicates a role for BuChE that must be recognized, especially by those practicing in areas or populations with narcotic usage. Furthermore, exogenous (human) BuChE has been shown to confer protection against cocaine toxicity in rats, both when given prophylactically or therapeutically (Dretchen et al., 1992). Following the elucidation of the pharmacological effects of cocaine, a series of analogs was synthesized, yielding some of the local anesthetics still in use today. As their chemistry is based on that of cocaine, not surprisingly they, too, are subject to hydrolysis and inactivation by BuChE (Baldessarini, 1990).

In the transgenic assay systems, the Xenopus embryo system is advantageous with respect to the time course of the assay procedure, i.e. it is experimentally easy to handle Xenopus oocytes, fertilize them, microinject them with DNA constructs and obtain relatively large numbers of transgenic embryos, which develop rapidly to yield a functional neuromuscular system within 48 hours, at which stage they may be used to screen the substances as noted above. Further, as noted in Ben Aziz-Aloya et al., (1993) DNA constructs encoding human AChE with either the CMV or human promoter are effective in causing overexpression of AChE in Xenopus.

The transgenic mice system is advantageous in that it provides an in vivo model system which is closer to humans physiologically.

In view of this, the two transgenic systems can be used in parallel or one after the other, for example, for rapid screening of a large number of substances, the transgenic Xenopus system may be employed, those substances of greater interest than being tested on the corresponding transgenic mice.

As regards assay procedures to be used in the various transgenic systems, these are as described for the transgenic Xenopus (Seidman and Soreq, 1996) and the Examples herein below for mice. In addition, assays for enzymatic hydrolysis of butyrylthiocoline (BuTCh) or acetylcholine (ACh) by BChE and AChE respectively have been detailed in Loewenstein et al., 1993.

In the transgenic assay system, the assay is performed in Xenopus in the following way: The transgenic embryos are allowed to grow and are then exposed to the prospective substance in the incubating medium in a dose and time dependent manner. The rate of mortality of the embryos and in vivo inhibition of the expressed human AChE would indicate the anti-cholinesterase activity of the substance. Post-mortem analysis of the drug-treated transgenic embryos may reveal correlation between the mortality rate and inhibition of the enzyme in target tissue; or whether the enzyme (i.e. naturally occurring or synthetic form) expressed in the embryos constitutes an in vivo target for the tested substance and whether adding protein (i.e. AChE, BChE) would afford protection against the substance and at what levels of the substance such added protein would be necessary.

The present invention also provides a transgenic animal assay system in mice which provides a model system for testing for, and treatments of, cholinergic deficits and/or imbalances in mammals such as cognitive functioning in Alzheimer's patients, thermoregulation, amyotrophic lateral sclerosis and retinal photoreceptor degeneration (RD).

The assay system of the present invention allows the exploration of the formation and functioning of cholinergic brain synapses. Imbalanced cholinergic signaling is associated with a number of neuronal disorders, including Alzheimer's and Parkinson's (Wurtman, 1992). This imbalance includes deficits in acetylcholine (Coyle et al, 1983), reduced levels of cholinergic receptors and modified numbers and size of synapses in patient's brains (Newhouse et al, 1994). Examples below provide evidence that the transgenic assay system, and in particular, the transgenic mouse of the present invention provides a model with these parameters which can be used for screening treatments for diseases with imbalanced cholinergic signaling. To confirm this and further extend the validity of the model, the effects of DFP, the muscarinic agonist oxotremorine, nicotine and the serotonergic agonist 8-OH-DPAT, were studied in the model. Further, the spatial learning ability and memory of the transgenic mice were also tested as well as their response to tacrine, as tacrine is the first drug approved by the FDA for use in Alzheimer's disease.

The present invention allows for the exploration of retinal photoreceptor degeneration. Transgenic mice expressing human, in addition to endogenous, AChE exhibit a rapid, bilaterally symmetrical retinal photoreceptor degeneration identifiable after postnatal day (P) 10, at which time, their photoreceptor cells undergo accelerated apoptosis. By P20, the photoreceptor layer is 10-fold reduced to a single nuclear layer and by adulthood, is no longer distinguishable. RT-PCR tests, histochemical and immunocytochemical staining demonstrated transiently high levels of catalytically active hAChE within several retinal layers of developing transgenic mice in a spatiotemporal pattern corresponding to the expression of the host AChE gene and diminishing with age. Transgenic AChE mRNA levels and specific activity were considerably higher than those of the host gene, suggesting that the excess in AChE expression was the cause for photoreceptor degeneration. However, there were no major changes in other cholinergic elements in the transgenic retina. Therefore the transgenic mice offer a model for studies on photoreceptor degeneration. Further, it has been determined that the rods are first lost and then the cones as happens in retinitis pigmentosa. Further, dark rearing did not recue the retina nor did DFP treatment.

Examples herein below set forth the results of these studies and confirms the validity of the transgenic assay system. The transgenic mice displayed relative resistance to the hypothermic effects of DFP, the muscarinic agonist oxotremorine, nicotine and the serotonergic agonist 8-OH- DPAT indicating that the overexpressed enzyme conferred physiological changes in drug responses and that additional key protein(s) involved in such responses were modulated. In water maze tests the transgenic mice displayed impairments in spatial learning and memory. In transgenic retinas photoreceptor degeneration is seen. Thus these AChE overexpressing mice provide a mammalian model where both physical and cognitive cholinergic responses are amenable for testing.

The Examples herein below utilize the observation that transgenic overexpression of human acetylcholinesterase enhances the rate of ACh hydrolysis, creating a cholinergic imbalance. Applicants have used this experimental approach in two evolutionarily distinct organisms: developing tadpoles of the frog Xenopus laevis (Ben Aziz-Aloya et al., 1993; Shapira et al., 1994; Seidman et al., 1995) and the laboratory mouse (Beeri et al., 1995; Andres et al., 1996). The Xenopus system is versatile and economical (Seidman and Soreq, 1996). Therefore, it provides the opportunity for rapid changes of the microinjected DNA and enabled Applicants to demonstrate that the synaptic accumulation of AChE depends on the 3'-exon No. 6 of the human ACHE gene. However, the transgenic DNA is not integrated in Xenopus, limiting the duration of the induced imbalance. In contrast, the human transgene has been stably introduced into the mouse genome, ensuring genetic transmission of the imbalance situation from one generation to the next.

As shown in the Examples, certain peripheral consequences of AChE overexpression were common to the frog and the mouse systems. In both systems, electron microscopy analyses demonstrated structural abnormalities in neuromuscular junctions (NMJs), which were similarly enlarged in Xenopus tadpoles and in adult mice. In addition, secondary changes in the levels of muscle nicotinic ACh receptors in Xenopus NMJs were indicated by the increased α-bungarotoxin binding (Shapira et al., 1994). In mouse NMJs, abnormal electrophysiology and post-excitation fatigue in older animals reflected progressive deterioration of neuromotor function (Andres et al., 1996).

As shown herein, cholinergic pathways in the central nervous system (CNS) were studied in the transgenic mice (Beeri et al., 1995; Andres et al., 1996). These analyses demonstrated acquired resistance to the hypothermic responses induced by AChE inhibitors and cholinergic agonists as well as the progressive deterioration of learning and memory capacities. Table I summarizes these consequences of transgenic overexpression of human AChE in the Xenopus and mouse systems and are detailed in the Examples.

EXAMPLES

The present invention will now be described in more detail in the following non-limiting examples and the accompanying figures.

General Procedures and Materials (a) *General methods in molecular bioloqy*. Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) was carried out generally as in *PCR Protocols: A Guide To Methods And Applications*, Academic Press, San Diego, Calif. (1990).

(b) The establishment of the Xenopus transgenic model and all methods and procedures is as set forth in Seidman and Soreq (1996).

EXAMPLE 1

Initial Establishment of Stably Transgenic Mouse Lines Expressing the Human AChE Gene (a) Establishment of transgenic mouse pedigrees. Two DNA constructs were employed: one with the pan-active cytomegalo-virus (CMV) promoter (Velan et al., 1991) and AChEcDNA and the other with approximately 600 bp (596 bp) of the authentic human ACHE promoter followed by the first intron from the AChE gene HpACHE (Ben Aziz-Aloya et al., 1993) to improve its regulation in the transgenic mice, and the AChEcDNA sequence encoding this enzyme. Both transgenes included the full coding sequence for human AChE (Soreq et al., 1990) and were shown to be expressible in Xenopus oocytes and embryos, with the CMV promoter being 20-fold more efficient than HpACHE in promoting AChE production in Xenopus (Ben Aziz Aloya et al., 1993, Seidman et al., 1994). FIG. 4 is a diagram of these two DNA constructs, their composition and the positions on them of PCR primers employed to detect their presence in the transgenic mice. The transgenic mice were prepared by standard procedures of transformation to obtain transgenic animals, as set forth, for example, in (Shani, 1985 and in the general methods listed hereinabove).

Injecting over 70 eggs resulted in one pedigree carrying the transgene with the CMV promoter (HpACHE) and three others with variable copy numbers of the construct carrying the human ACHE promoter (Table II). Three independent pedigrees of transgenic mice carrying the human AChE promoter-reporter construct were established. Further experiments were carried out in the descendent generations of mice from these pedigrees, all of which presented grossly normal development and behavior.

Figure 6:
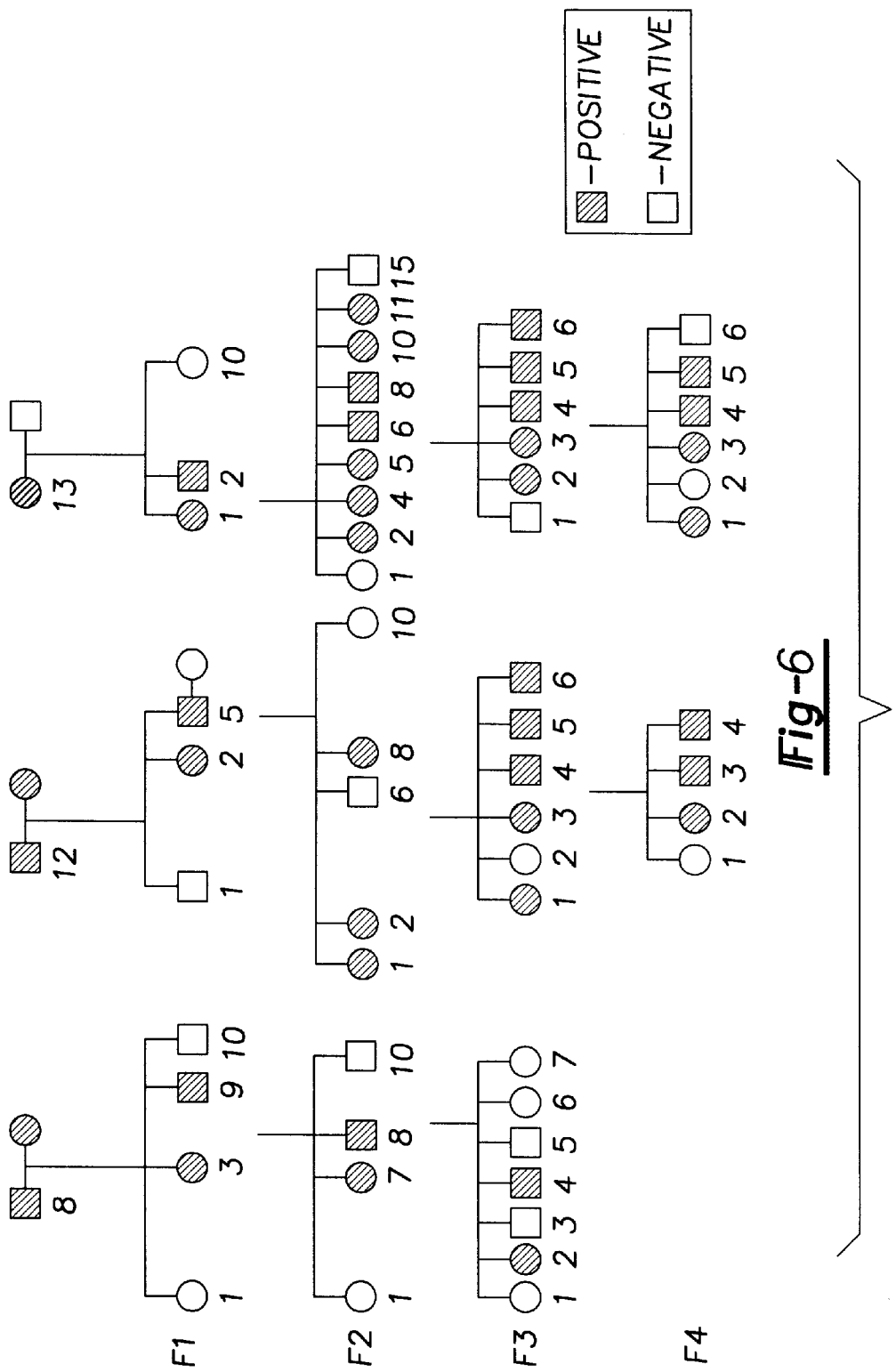
FIG. 6 is a schematic presentation of transgenic mice family pedigrees; the squares and circles having diagonal lines indicating positive, i.e. transgenic animals and the open squares and circles indicating negative, as described in Example 1.

(b) Determination of copy numbers. Tail DNA restriction analysis and blot hybridization were employed to differentiate between the human ACHE transgene and its murine counterpart. Kinetic follow-up of PCR amplification (Lev-Lehman et al., 1994) was used to quantify copy numbers of the transgene. For calibration, known amounts of the human gene were subjected to a similar procedure. Furthermore, positive mice were identified by informative PCR amplifications of tail DNA and copy numbers were evaluated by a kinetic follow-up of the PCR reactions, as confirmed by DNA blot hybridizations (see schematic representation of the procedure and the blot hybridization results in FIG. 5). The various procedures employed were standard ones for quantitative PCR and PCR kinetics determinations (Lev-Lehman et al., 1994). FIG. 6 presents these family pedigrees. DNA blot hybridization revealed expected restriction patterns in two pedigrees with one and two copies/genome (pedigrees 8, 13 respectively) and rearrangement in another pedigree (8) with 12 copies/genome.

Thus, the above noted HpAChE construct, having the human AChE gene promoter was successfully employed to obtain transgenic mice in which the human AChE is expressed. The HpAChE pedigrees shown in FIG. 6 were obtained as follows: Three different founders (Fo, transgene presence verified as detailed above) were mated with wild type mice to create the FI generation. Mating of FI mice, with wild type mice gave rise to the FII generation. FIII mice were generated by mating of FIIxFII mice. Note the increase in the fraction of positive transgenic mice (closed squares and circles, negative mice, i.e. non-transgenic being those shown by open squares and circles in FIG. 6) within pedigrees 12, 13, but not 8, from Fo to FIV and the gradual decrease in litter size, indicating selection disadvantage of the transgene at the germ line and/or early embryogenesis levels.

However, it should be noted that in three separate DNA construct preparations and microinjection procedures, applicants could not get any transgenic mice carrying and expressing the CMV-AChE construct, although this construct was efficiently expressed in Xenopus oocytes and embryos. In view of the strength of this promoter (CMV), as compared with the HpAChE one (Ben Aziz-Aloya et al., 1993), this indicates that high levels of AChE expression may be lethal in embryonic stages and/or in the process of fertilization in mammals. Accordingly, for the preparation of transgenic mammals (e.g. mice, rat, etc.), the preferred vector is the one with a human AChE promoter, e.g. the HpAChE vector or vector incorporating the promotor as set forth in SEQ ID No:7.

(c) Phenotypic observations in transgenic mice carrying the HDAChE construct. Three primary sites for AChE expression are brain and neuromuscular junctions (NMJ), where the enzyme product of this gene controls termination of neurotransmission (Soreq and Zakut, 1990), and hematopoietic cells, in which a growth-regulatory role was proposed for AChE (Paoletti et al., 1992). In search for the biological role(s) of the transgene product, applicant therefore examined these three sites for expression of the transgene and phenotypic alterations.

(i) Brain. Brain general morphology was apparently normal in the examined transgenic mice, and subtle differences, if they exist, may be detected following analysis by immunohistochemical staining. Species-specific RNA-PCR examination of total brain RNA using human AChE specific primers revealed human-specific PCR products in two transgenic brains from family No. 13 but not in two control brain RNA samples and not in one brain from family No. 8 and one from family No. 12. Thus human AChEmRNA is expressed in adult brain of the transgenic mice.

To examine whether active enzyme was produced from the transgene, homogenates from whole brains were incubated in multiwell plates covered previously with monoclonal anti-AChE antibodies selective for the human enzyme. Following washes, acetylthiocholine hydrolysing activities were measured in duplicates by the Ellman spectrophotometric procedure. Recombinant human AChE, produced in bacteria from the same DNA, using standard procedures, served as a control. Table III demonstrates that duplicate brain homogenates from transgenic, but not control mice displayed binding of active enzyme to the mAb.

Figure 7:
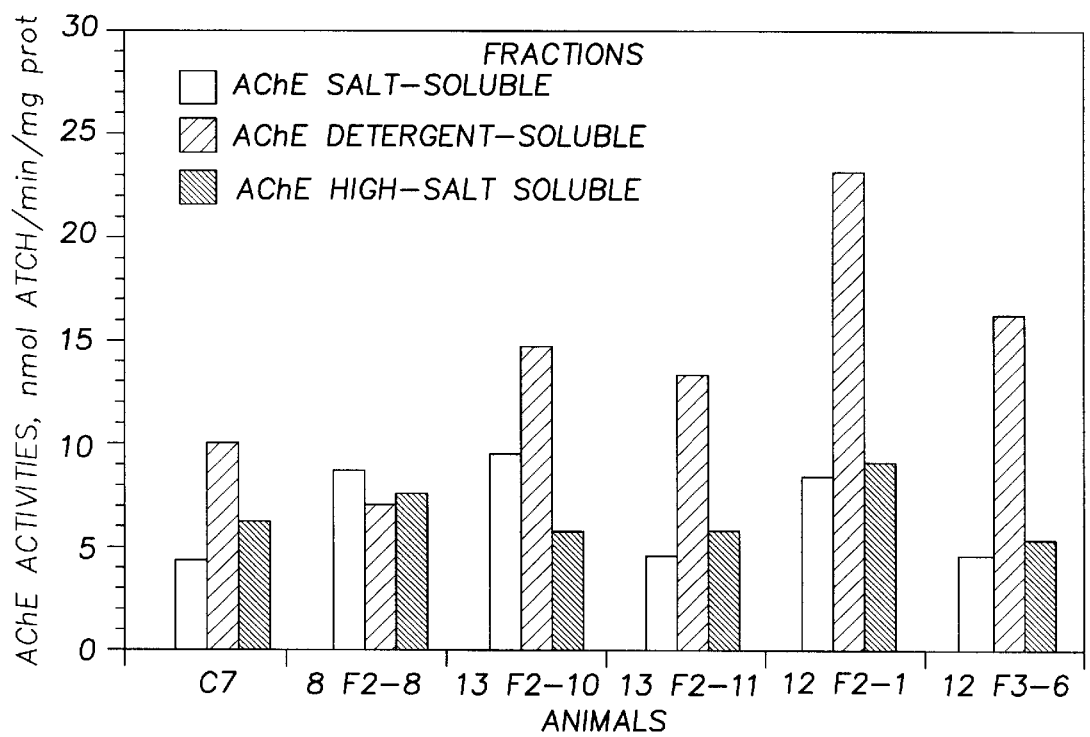
FIG. 7 is a bar graph of the results of the overexpression of AChE in the detergent-soluble fraction of muscle homogenates from the HpAChE-transgenic mice, as described in Example 1.

(ii) Muscle. Specific activity of AChE was determined following subcellular fractionation of homogenates of transgenic and control muscles, using the Elman spectrophotometric procedure in the presence of the specific BCHE inhibitor ISO-OMPA. In FIG. 7 there is shown the results depicting the overexpression of AChE in the detergent-soluble fraction of muscle homogenates from the HpAChE-transgenic mice. Muscle extractions and detergent and salt fractionations were performed. Note the increase in amphiphylic, but not membrane-associated or soluble AChE in correlation with the transgene copy number. The different fractions are denoted by differently shaded bars, as indicated in the figures. Thus, from FIG. 7 it is apparent that higher activity is observed in the transgenic samples (especially in the detergent soluble fraction) in correlation with the transgene copy number (8<13<12). Immunoassays revealed no human AChE enzyme bound to the plate.

(iii) Neuromuscular Junctions. Neuromuscular junctions (NMJ) in three HpAChE transgenic mice were examined for their structural buildup and AChE expression. To this end, applicants performed electron microscopy studies of tongue synapses (tongue muscle NMJ structures) following cytochemical staining for AChE activity. Longer, curled post-synaptic folds with conspicuous enzyme staining and denser vesicles were observed using electron microscopy in the transgenic mice. The NMJ structures from the transgenic mice displayed excessively long and curled post-synaptic folds which were closely spaced and filled with reaction product. Moreover, there was high density of membrane vesicles in the nerve terminals, all as compared with parallel NMJ from control mice. This demonstrated active participation of the AChE gene in synaptic development, in agreement with our observations of such involvement, in the developing NMJ of Xenopus embryos. The observed NMJ alterations further indicated adjustment of the hierarchic control of cholinergic signaling in the transgenic NMJ. Such hierarchic control could, by feedback regulation, adjust the amount of key synapse proteins to enable correct neurotransmission even under conditions of overexpressed transgenic AChE. The reciprocate indication which stems from these observations is that underexpression of the AChE gene (i.e., in cases of prolonged exposure to inhibitors) may cause defects in NMJ development.

(iv) Hematopoietic Cells. Preliminary findings with 8 transgenic mice revealed striking phenotypic differences in bone marrow composition of some mice (Table IV). Electron micrographs from bone marrow smears from two FI transgenic mice (12-12, female and 13-2, male marked as in FIG. 6) and one control (c, male) were stained with Giemsa. Lymphocytes and erythroid cells were observed in the female mouse 12-12 as opposed to increase in erythroid cells and megakaryocytes, which share a common progenitor, in the male mouse 13-2. Thus, numerous megakaryocytes appeared in the FI male (with 2 HpAChE copies). This defect in megakaryocytopoiesis, was accompanied by a conspicuous phenomenon of subcutaneous bleeding in this particular FI male, reflecting a serious aberration in platelet production as found during post-mortem (P.M.) analysis, which shows multiple internal subcutaneous bleeding sites in the 13-2 transgenic mouse (T 13-2) but not in an age and sex-matched control (C1). It should be noted that applicants have previously observed a similar phenotype of multiple immature megakaryocytes in the bone marrow and extremely low platelet counts in a Lupus Erythematosus patient with AChE gene amplification in her peripheral blood cells (Zakut et al., 1992). Significant increases in erythroblasts and normoblasts, compensated by decreases in granulocytes occurred in transgenic mice (Table IV).

Figure 8A:
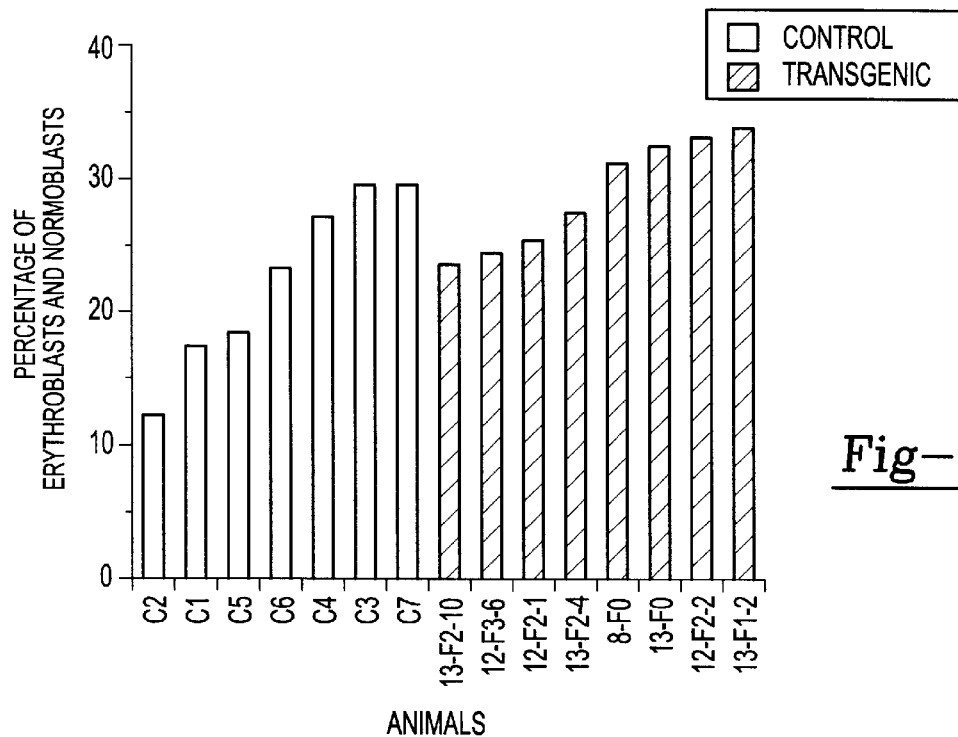
FIGS. 8A,B are bar graphs shows the results of lower variability in bone marrow composition and enhanced erythropoiesis in HpAChE transgenic mice, as described in Example 1.
Figure 8B:
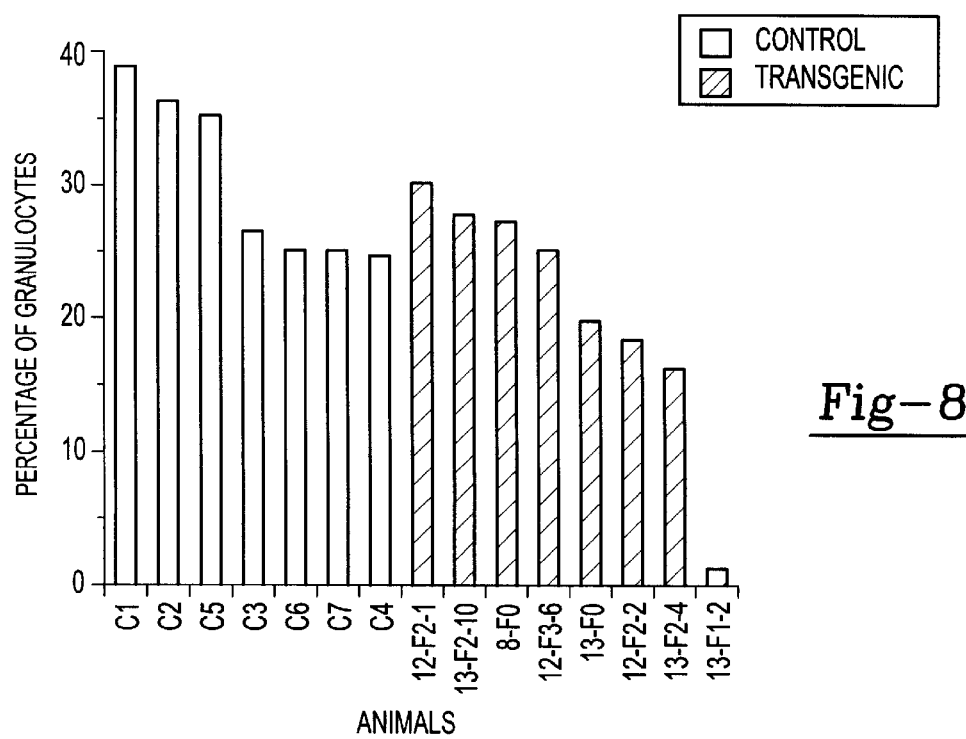

In FIGS. 8A,B the results depicting the lower variability in bone marrow composition and enhanced erythropoiesis in HpAChE transgenic mice are shown. Differential cell compositions were determined in fresh bone marrow smears from the 8 noted transgenic mice and 8 age and sex-matched controls, wherein FIG. 8A shows the percentages of erythroblasts and normoblasts and FIG. 8B shows the percentages of granulocytes in the control (open bars) and transgenic (closed bars) animals. Note the limited variability (22–35%) of red blood cells in the transgenic vs. controls (12–30%), and the higher average content of red cells in the transgenic mice.

Thus, from FIG. 8 it is apparent that the percentage of erythroblasts and normoblasts in the transgenic mice is significantly less variable in the transgenic bone marrow than in the control mice and reached higher values (average 28.9% as compared with 22.4% for 8 mice in each group). An average percentage of granulocytes in the transgenic mice was lower than in the control mice (20.3% as compared with 29.7%).

Figure 9:
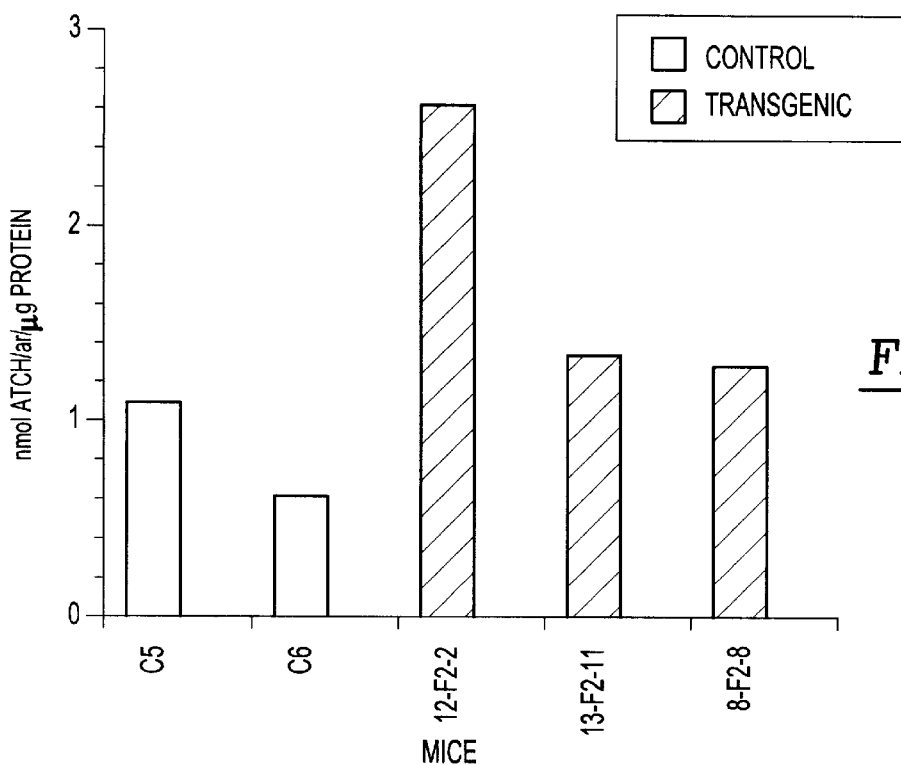
FIG. 9 is a bar graph showing the BW sensitive AChE activities in bone marrow from two control (open bars) and three transgenic mice (bars with diagonal lines), demonstrating that the transgenic bone marrow contains high levels of AChE activity, as described in Example 1.

AChE activities in bone marrow were measured by the Elman spectrophotometric procedure, with or without BW, a selective and specific AChE inhibitor. FIG. 9 represents the BW sensitive AChE activities in bone marrow from two control (open bars) and three transgenic mice (closed bars), demonstrating that the transgenic bone marrow contains high levels of AChE activity.

Differential cell counts were determined in percentage by observing cell shape, size and histochemical staining for each of the noted mice. Distinct variations were noted in differential cell compositions of the transgenic mice as compared with controls.

Figure 10:
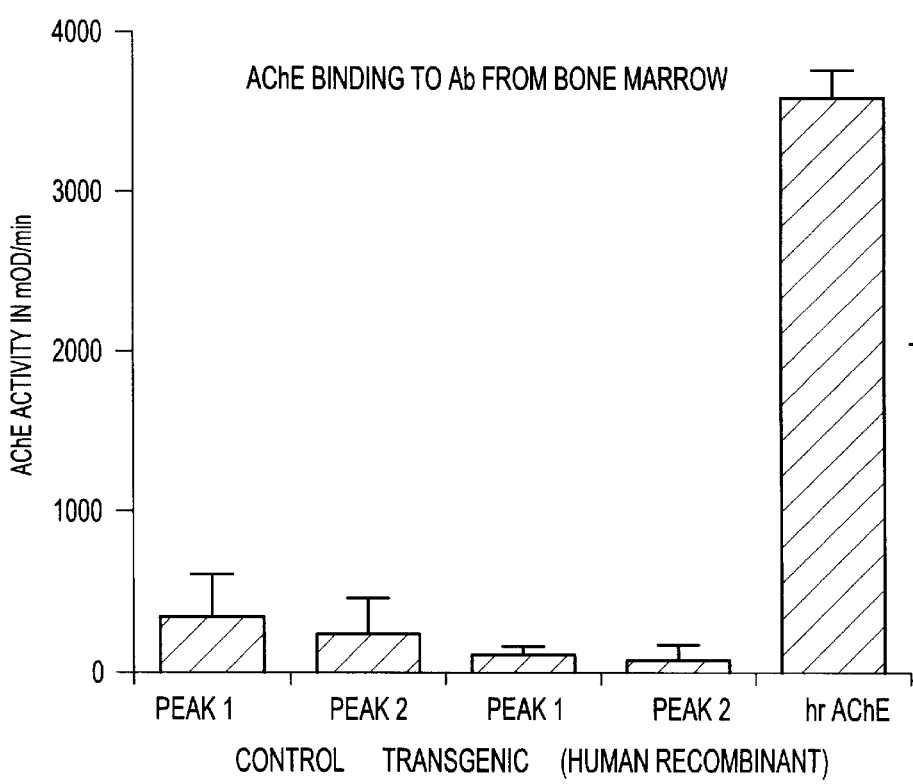
FIG. 10 is a bar graph of the results which indicate that the human AChE protein cannot be specifically detected in adult bone marrow of HpAChE transgenic mice, as described in Example 1.

Immunoadsorption assays using the monoclonal antibody 101-2 (specific for human AChE) did not show any difference between the bound activity of homogenates from control and transgenic bone marrow (active fractions from the gradients were concentrated together). In FIG. 10 there is shown the results which indicate that the human AChE protein cannot be specifically detected in adult bone marrow of HpAChE transgenic mice. Bone marrow homogenates from two control and two transgenic mice were analyzed for their total AChE activities and for their content of human AChE, immunoreactive with the species-selective mAb antibodies tested previously. Note that no human-characteristic AChE could be detected in the transgenic mice, although their total bone marrow activities were apparently higher, as noted above. Recombinant human AChE served as control for the adsorbance capacity of the employed mAb. Thus, the higher activities in the bone marrow were concluded as being of murine origin, probably in megakaryocytes.

To examine the proliferative potential of bone marrow cells from these transgenic mice, primary cultures of these cells were grown in the presence of recombinant interleukin-3 into colony forming units (CFU). These were composed of megakaryocytes, macrophages, polymorphonuclear cells and erythroid cells. Colony counts were lower by 80% for transgenic as compared with control mice (Table V, herein below), suggesting that the transgene reduced the proliferative capacity of hematopoietic cells in these mice. Within surviving colonies, there were 2-fold fewer blast cells and 2-fold larger fractions of red blood cells in the transgenics as compared with controls. Thus the transgene also promoted erythropoietic differentiation in culture, in line with the abundance of erythrocytes in the bone marrow of the transgenic mice. In the presence of erythropoietin (Epo) and IL-3 in the culture medium and growth for 12 days in three experiments, the colony numbers remained 2-fold lower in the transgenic as compared with control cultures (Table V) (i.e., the effect of the transgenic enzyme could not be compensated by Epo) but the differentials were not in line with the fresh bone-marrow differential counts (Table V). Most importantly, addition of 2.5 $\mu$M anti-sense AChE oligonucleotide (AS-AChE) capable of destructing AChEmRNA (Lev-Lehman et al., 1994) to the CFU-GEMM cultures enhanced colony counts and cell numbers in the transgenic cultures up to the level of controls, in one out of two experiments (Table V). Thus, the defective proliferation of bone marrow stem cells was apparently due to the overexpression of the transgenic AChEmRNA in them.

It is important to note that the transgene (i.e. that encoded by the HpAChE construct) encodes for the brain, hydrophilic form of the enzyme and not the erythrocyte specific, phosphoinositide-linked one. This implies than the alternative C-terminus does not prevent the hematopoietic growth-related effect of AChE.

(v) Apoptosis in BM cultures. In search for the cause of the suppressed proliferation of hematopoietic cells from the transgenic mice, bone marrow CFU-GEMM colonies of 2 control and 2 transgenic mice were grown in the absence or in the presence of anti-sense AChE oligonucleotide (AS-AChE oligo.—see (iv) above). DNA was extracted from these colonies and was checked for the extent of apoptotic fragmentation. As applicants know from previous studies, the AS-AChE oligo prevents the apoptotic fragmentation under these conditions. One transgenic mouse showed apoptosis levels similar to the control mice, the other showed a higher level of small DNA fragments and less protection by the AS oligo.

(vi) Sucrose gradient centrifugation. Sucrose gradient centrifugation revealed similar sedimentation profiles for AChE activities from various tissues of the MpACNE transgenics and control mice, demonstrating unmodified assembly into multimeric enzyme forms. Gel electrophoresis followed by cytochemical staining likewise revealed no differences, further suggesting similar glycosylation patterns. To distinguish between the transgene-derived and the host enzyme forms, gradient fractions were incubated with human-specific monoclonal antibodies adhered to multiwell plates (Seidman et al., 1994). Up to 20% of the active enzyme in brain and 10% of the muscle enzyme, but none in bone marrow, were thus found to be of human origin. The presence of human AChE protein but not ACHEmRNA in muscle suggested that the human enzyme observed in these homogenates was contributed by motor neurons.

(vii) in situ Hybridization and Cytochemical staining. To further associate hACHEmRNA transcripts and hAChE activities with specific CNS cell types, applicants performed in situ hybridization and cytochemical staining experiments in 50 $\mu$m thick brain sections. The extensive homology between the human and mouse products lead, in both these tests, to detection of mRNA and protein from both human and mouse sources. Labeling ACHEmRNA transcripts revealed similar brain neurons in transgenic as in control sections, yet with considerably higher efficiency. The cholinoceptive hippocampal neurons were labeled with particularly high intensity, especially in the CA1 region, as were giant striatal neurons and other cell bodies in the brainstem, cortex and cerebellum. Thus expression of the HpACHER transgene was apparently confined to host nerve cells normally expressing the ACHE gene.

Intensified cytochemical staining of AChE activity was observed in brain sections from transgenic mice in all of the areas normally stained for AChE activity. Staining was particularly intense in the neostriatum and pallidum domains, demonstrating that the transgenic enzyme produced in the neuronal cell bodies decorated in the in situ tests was faithfully transported into nerve processes and suggesting that its levels were also increased in cholinergic synapses. To examine whether this enhancement in AChE activities, and the consequent expected changes in cholinergic signally caused feedback response(s) in transcription patterns, applicants prepared differential PCR displays using an arbitrary primer from pooled RNA extracted from each of the examined brain regions. At least 50 PCR products were amplified from each region. Some of these were common to all regions and others unique to specific regions. Interestingly, several of these products were drastically reduced in the transgenic brains regions as compared with corresponding controls. Moreover, certain bands appeared to be reduced in cortex, brainstem and central nuclei. Assuming expression of at least 10,000 distinct transcripts in each brain region these differences suggest suppression of several hundred genes in the transgenic mouse brain overexpressing human AChE.

EXAMPLE 2

Knock-out Mice

The mouse AChE gene present in the above noted transgenic animals (Example 1) were destroyed by standard, "knockout" technology to obtain an animal model with the human AChE gene alone. To delete the murine AChE gene by targeted destruction, applicants subjected the embryonic stem to homologous recombination with a neomycin resistance gene boarded by 5' and 3' fragments from the mouse AChE gene (Li et al., 1991). Neo resistant stem cells were subsequently employed according to published procedures (see, for example, Plump et al., 1992 and references listed in methods hereinabove) to create, by microinjection, transgenic mice in which one of the AChE copies cannot be expressed. Cross-hybridization of such mice with the HpAChE transgenics subsequently created the next generation of HpAChE transgenic mice. These second generation transgenics were devoid of the murine enzyme altogether, so that the only AChE expressed in them was the human enzyme. The transgenic replacement yields, for the first time, an authentic animal model with which the response of human AChE to drugs and poisons can be tested in vivo.

EXAMPLE 3

Assaying Substances Which Effect AChE Expression or Which Inhibit AChE Activity in the Transgenic Model Cholinesterases (e.g. AChE) have been implicated in a number of diseases, for example, Alzheimer's disease, leukemias, carcinomas, Parkinson's disease, glaucoma, multiple sclerosis and myasthenia gravis. Accordingly, anti-cholinesterase drugs are employed to treat such diseases. Furthermore, anti-cholinesterase poisons form a broad category of agricultural and household pesticides, including various organophosphate and carbamate agents: organophosphate (OP) insecticides have been shown to be the causative agents in about 1 million acute injuries and about 20,000 deaths per year worldwide, and are also believed to increase the risk to develop leukemias in persons coming into regular contact with these substances. In fact, the teratogenic effects of several organophosphate substances on skeletal formation (Meneely and Wyttenbach, 1989) and somitogenesis (Hannenman, 1992) have been correlated to their anticholinesterase activities (see also Zakut et al., 1991). Carbamate compounds which have cholinesterase inhibitory activity are widely used as therapeutic agents and as insecticides. Various snake venoms and plant glycoalkaloids have also been shown to have anti-cholinesterase activities.

In accordance with the present invention, such an anti-cholinesterase assay system has been developed. As mentioned in detail in the preceding Example, transgenic animals have been prepared which express various AChE gene constructs. The advantage of these transgenic animals (Xenopus embryos and mice) is that they provide, for the first time, an in vivo method to assay rapidly and effectively the effect of anti-cholinesterase substances on the expression of human AChE.

Figure 11A:
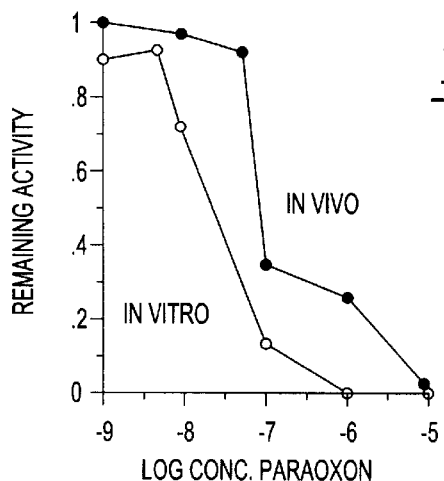
FIGS. 11A–C are graphs of the in vivo inhibition of human recombinant AChE by Paraoxon, as described in Example 3.
Figure 11B:
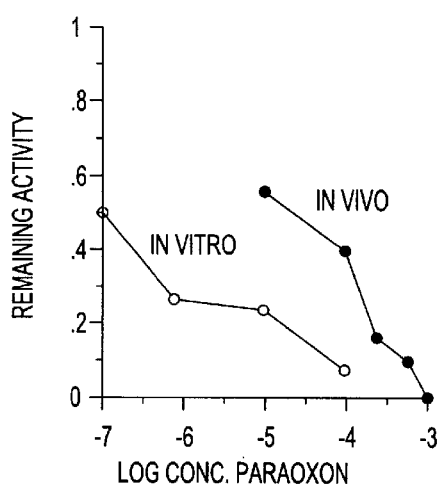
Figure 11C:
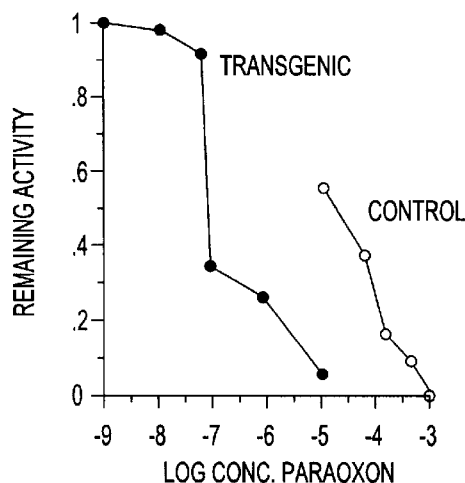
Figure 12:
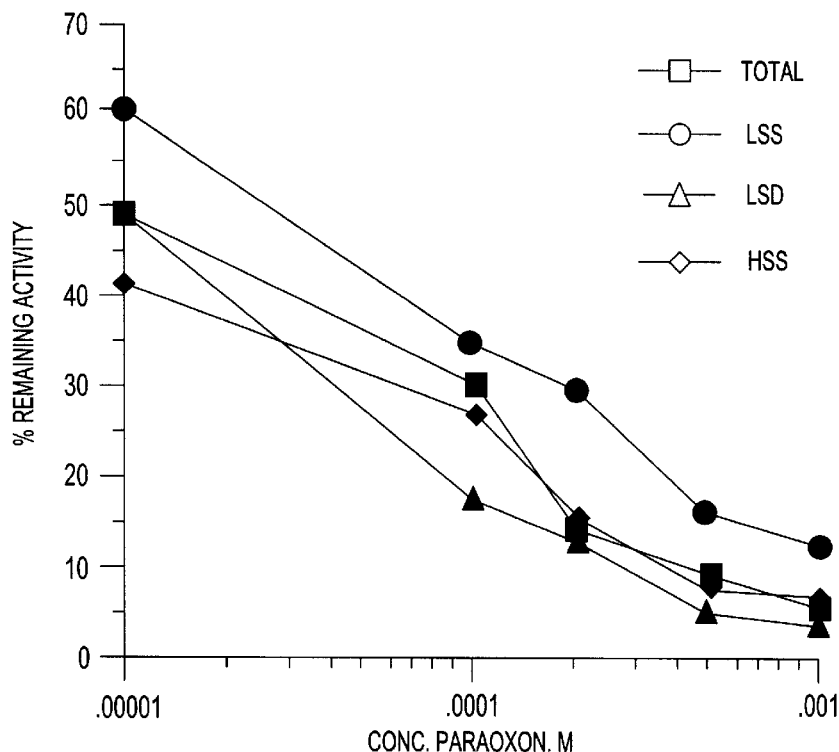
FIG. 12 is a graph of the in vivo inhibition of Xenopus AChE by Paraoxon, which inhibition affects all subcellular fractions of the enzyme, as described in Example 3.

The use of transgenic Xenopus embryos to assay for the toxicity of the anti-cholinesterase organophosphate poison, Paraoxon, is shown in FIGS. 11 and 12. In FIGS. 11A–C there is shown the in vivo inhibition of human recombinant AChE by Paraoxon. Using the procedures described in Seidman and Soreq, 1996, fertilized eggs of Xenopus were microinjected with 1 ng CMAChE DNA and cultured for 2 days at 17–21° C. Groups of 4 embryos were incubated for 30 minutes with various concentrations of Paraoxon, washed, homogenized in a high salt/detergent buffer, and assayed for residual AChE activity (11A, in vivo). Uninjected, control embryos were similarly treated (11B, in vivo). For comparison, homogenates from day 1 AChE-injected or day 10 uninjected control embryos were similarly incubated with inhibitor and assayed for remaining activity (11A-B, in vitro). Note the 5–10 fold decrease in sensitivity observed for both enzymes under in vivo conditions and the 100 fold higher sensitivity of human AChE to Paraoxon than that observed with embryonic Xenopus AChE (11C).

In FIG. 12 there is shown the in vivo inhibition of Xenopus AChE by Paraoxon, which inhibition affects all subcellular fractions of the enzyme. Two day old "tailbud" embryos were exposed to increasing concentrations of the organophosphorous cholinesterase inhibitor paraoxon for 30 minutes, allowed 1.5 hours recovery, then frozen. Sequential extractions with low salt (20 mM Tris-HCl (pH 7.5), 10 mM $MgCl_2$, 50 mM NaCl), low salt/detergent (10 mM phosphate buffer (pH 7.4), lo Triton X-100), and high salt (10 mM phosphate buffer (pH 7.4), 1 mM NaCl, 1 mM EGTA) buffers demonstrated that AChE activity in the soluble (LSS), membrane-associated (LSD), and extracellular matrix associated (HSS) fractions were equally inhibited during exposure. Each point represents one group of 3 embryos. T-total AChE activity.

Thus, from FIGS. 11 and 12 it is apparent that recombinant human AChE as expressed in Xenopus tadpoles represents a viable model for the in vivo testing of AChE inhibitors, including both ligand-binding and inhibitor penetration properties.

The molecular basis underlying the anti-cholinesterase activity (toxicity) of carbamate substances (see Loewenstein et al., 1993) was also studied. In these studies comparative inhibition profiles were obtained for carbofuran and five other N-methyl carbamates, mostly carbofuran derivatives differing in length and branching of their hydrocarbonic chains, against human erythrocyte AChE (H.AChE), human serum BChE (H.BChE) in its normal form or in a mutant form containing the point mutation Asp70→Gly, and Drosophila nervous system ChE. The results indicated that carbofuran was most toxic to all the ChEs and that the Drosophila ChE was most sensitive to all the carbamates tested. Accordingly, such carbamates are good pesticides as they can be used at doses which are lethal to insects while, at the same time, cause little human ChE inhibition. Of the human ChEs, the AChE was more sensitive than the BChE to the carbamates, the BChE also having a lower flexibility towards changes in the carbamate side chain, i.e. the binding site for carbamates on BChE is less flexible than that of AChE towards changes in the carbamate side chain structure. Further, the above Asp70→Gly mutation had no effect on BChE inhibition by carbamates indicating that the Asp70 is not important in the active site for carbamate binding. Further, the results also indicated that the BChE has biological activities in mammals other than the simple scavenging activity attributed to this enzyme up to now. While the above anti-cholinesterase activity of carbamates on various ChEs was analyzed in vitro, it is clear that, on the basis of the description in Examples above, the same analysis may be carried out in transgenic animals such as the transgenic Xenopus and mice. In this situation, the relevant ChE constructs (i.e. the above described AChE constructs as well as BChE and Drosophila ChE or other insect ChEs) may be introduced into the animals to obtain transgenic animals expressing such ChEs. These transgenic animals may then be used to analyze in vivo the effects of carbamates and other substances (e.g. organophosphates).

EXAMPLE 4

CHARACTERIZATION OF TRANSGENIC MICE COGNITIVE IMPAIRMENT

Additional Protocols and Methods:

Water maze test:

General Design. The procedures were modified from Morris (1989). The mice were tested in a square Plexiglas swimming pool, 61×61×30.5 cm, with an 11 cm high water level. The water contained 1.5 g/l powder milk and its temperature was 25° C. A hidden platform of 10×10 cm was in one quadrant of the pool, at 1 cm below the water level. At the beginning of a testing session, the mouse was placed in the water in a randomly chosen corner of the pool and the time necessary to climb to the platform was measured with a stopwatch. If the mouse didn't find the platform after 2 minutes, it was taken out of the water and put back after 30 seconds. The mice were tested 4 times each day at 30 seconds intervals.

Figure 13:
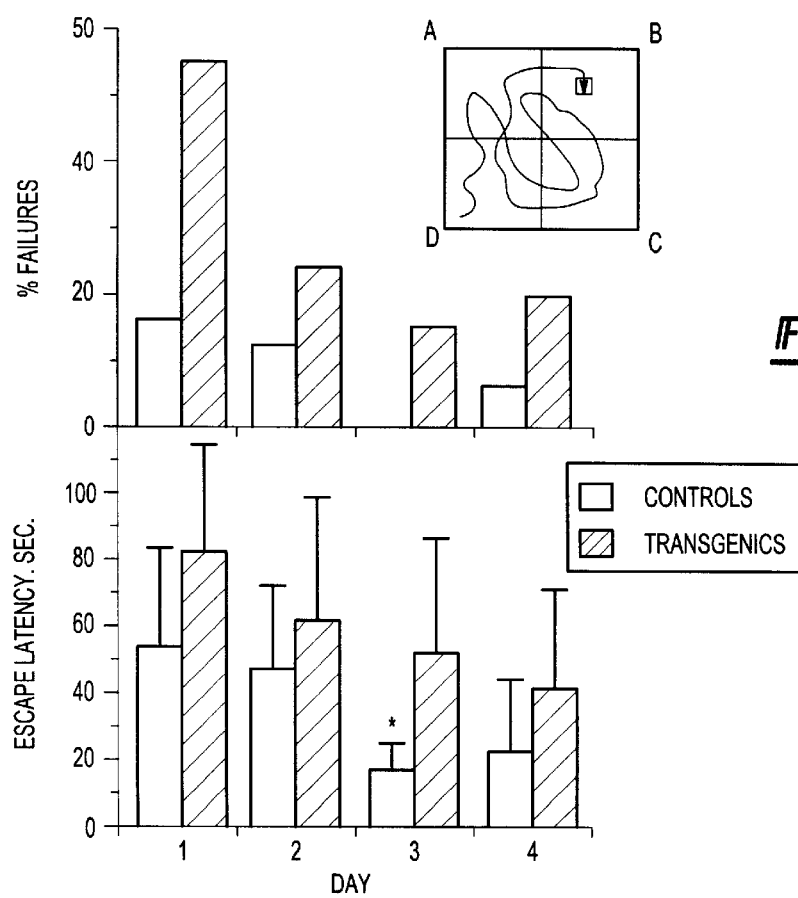
FIG. 13 shows graphically the results of the water maze test as used in Example 4.

Water Maze Protocol for initial experiments (FIG. 13). Experiment 1 was designed to train the mice and to see their general behavior. The hidden platform was fixed in one quadrant. Four sessions were repeated each day during four days (day I to 4). In Experiment 2, the platform was removed on day 6 after the beginning of the experiment, to see if the mice remembered its location. The time spent in each quadrant was noted in 5 sec intervals during one minute. In Experiment 3, on day 8, the platform was located in an other quadrant. The mice were first put 10 seconds on the platform, to know its position, and then removed. After 30 seconds, the mice were tested as in the first experiment. The same experiment was repeated on day 9, with a new position of the platform and with IP injection of 200 ml of 10 mg/kg tacrine in PBS or PBS alone in two equal groups.

Effect of tacrine on the learning and memory steps. The design of the experiment was as follows: mice were injected IP with 200 ml of 20 mg/kg tacrine in PBS or PBS alone. 30–60 min after injection, they were tested in the water maze as in experiment 1, with the only difference that at beginning they were first put 10 seconds on the platform, to know its position. On day two, they were injected and tested as in day 1, with the same platform localization. The design of this experiment was similar to Experiment 3, with the difference that the mice were naive to the water maze, and were injected with tacrine or PBS.

Results.

To examine cholinergic functions in these transgenic mice, applicants first measured their hypothermic responses to the anti-AChE organophosphate diisopropylfluorophosphate (DFP). Relative, dose-dependent resistance to DFP-induced hypothermia was observed in the transgenic as compared with control mice. The transgenic mice were almost totally resistant to a low DFP dose (0.25 mg/kg) and displayed normal physical activity levels, shorter duration of response and limited reduction in body temperature with higher doses, while controls suffered severe cholinergic syndrome.

Moreover, the transgenic mice displayed relative resistance to the hypothermic effect of the muscarinic agonist oxotremorine, to the less potent effect of nicotine, and to the serotonergic agonist 8-OH-DPAT as compared to controls. This indicates that changes occurred in additional key proteins within their cholinergic synapses and that the action of serotonergic synapses involved in thermoregulation is influenced by the induced changes.

Applicants also examined the capacity of the transgenic mice to adapt to cholinergic insults. When repeatedly injected with 0.25 mg/kg DFP, both transgenic and control mice acquired cross-tolerance to oxotremorine-induced hypothermia, demonstrating unimpaired plasticity of their cholinergic functioning. Yet, no difference was detected between transgenic and control mice in response to the ($\alpha$2-adrenergic agonist clonidine, indicating that the noradrenergic synapses involved in thermoregulation are not subject to control by cholinergic elements and that these changes did not reflect general impairment in the control over body temperature. Also, the thermic response to cold exposure was similar in the transgenic and control mice.

Electron microscopy analysis of cytochemical staining revealed more conspicuous depositions of the electron dense reaction product of ACHE within dendrites in the thermoregulatory anterior hypothalamus of transgenic as compared with control brain sections, attributing the changes in thermoregulatory responses to ACHE overexpression. However, length of synapses interacting with these stained dendrites was indistinguishable in the transgenic mice as compared with controls. Thus, these mammalian brain synapses were more resistant to the modulation of key elements conferred by overexpressed human ACHE than neuromuscular junctions in Xenopus tadpoles, the length of which increased when hAChE was overexpressed in them (Seidman et al., 1994).

The hippocampal overexpression of the ACHE transgene predicted involvement in learning and memory. To explore this issue, applicants employed the hidden platform test of the Morris water maze (Morris, 1989). In this test, transgenic and matched control mice are trained to escape a swimming task by learning the position of a hidden platform and climbing on it. The time it takes them to complete this task is defined as the escape latency. Applicants determined for each animal the percentage of failures to find the hidden platform within 2 minutes (FIG. 13, top). Transgenic animals failed far more frequently than controls throughout the 4 days experiment. This was particularly conspicuous in day 1, with 54% failures for the transgenics as compared with 16% failures for the controls. Even after 3–4 days training, transgenic stayed at a plateau of 20% of failures, whereas control failures were reduced to 5% or less.

In parallel, the escape latency (taking a failure as 120 sec., e.g. the duration of a session) was longer for transgenic mice as compared with corresponding controls throughout the 4 days experiment and 16 training sessions. Whereas control mice shortened their initial escape latency of 53 sec. down to a plateau of 23 sec. by day 3, transgenics slowly improved from 82 to 42 sec. in 4 days (FIG. 13, bottom). Both the extent of shortening in the escape latencies and the ratio between learning rates in the transgenics and controls were similar to the parallel parameters reported for $\alpha$-calcium calmodulin kinase II mutant mice, with the exception that the transgenic strain of the present invention seemed to display slower performances than the one used by these authors.

The impairment of spatial learning and memory in hAChE-overexpressing mice displays a reciprocal paradigm to the use of anti-AChE drugs to improve cognitive functioning in Alzheimer's patients (Knapp et al, 1994).

Figure 14:
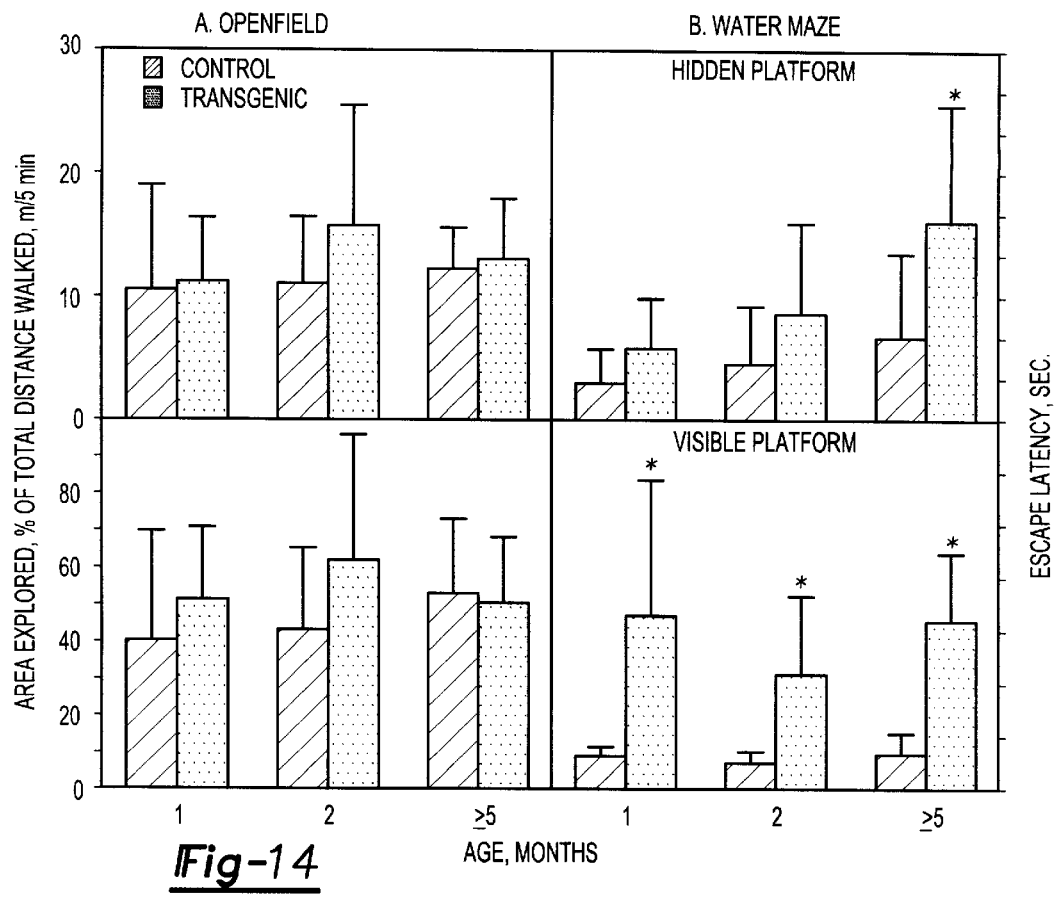
FIG. 14 is a graph of mice behavioral tests (A) Open field tests wherein mice spent 5 minutes in a void 60×60 cm box and their walkpath was traced, the walked distance and the explored fraction of the box floor were calculated thereafter and (B) Water maze wherein mice were tested in a water maze with a hidden platform in a fixed location (top) or with a visible platform in alternate location for each test (bottom) as described in Example 6, means of daily escape latencies are presented for the 4th day of transgenic (n=6 to 10) and age-matched controls, stars note statistically significant different latencies (ANOVA followed by Neuman Keuls test, $p<0.05$)

Transgenic AChE Does not Affect Open-Field Behavior but Induces Progressive Decline in Spatial Learning When compared to matched groups of non-transgenic control mice at the age of 1, 2–3 and 5–7 months, AChE-transgenic mice retained normal behavior in an open field. They covered the same space and distance as their control counterparts (FIG. 14). In addition, these mice did not display more anxiety than controls, as evaluated in the frequency of defecation incidents and grooming behavior.

In contrast, memory and learning tests revealed clear differences between transgenic and control mice as shown herein above.

Transgenic HpACHE is not Expressed Outside the CNS

As described herein reverse transcription and PCR amplification (Beeri et al., 1994) revealed that unlike the normal ACHE gene, the transgene is not expressed in muscle, adrenal and bone marrow. In contrast, both human and mouse ACHEmRNA transcripts were observed in dissected brain regions of the transgenic mice. There was no interference with the levels and alternative splicing patterns of host ACHEmRNAs, both remained apparently similar to those observed by others (Rachinsky et al., 1990).

When fixed brain sections from the mice were subjected to in situ hybridization with digoxigenin ACHEcRNA, followed by detection with alkaline phosphatase-conjugated anti-digoxigenin antibody (Boehringer/Mannheim), ACHE-cRNA labeling was seen in the same brain neurons in transgenics and controls (Beeri et al., 1995). Particularly intense labeling was observed in cell bodies in the basal forebrain and brainstem nuclei of the transgenic mice and in the cholinoceptive hippocampal neurons, especially in the CA1-CA2 region. Thus, the HpACHE transgene was expressed in the central nervous system neurons but not in the peripheral tissues normally expressing this gene in mammals. This is consistent with findings of others, who observed that separable promoter elements control neurogenic expression of pan-neural genes (i.e. Drosophila, snail) in the central and peripheral nervous system (Ip et al., 1994).

Multimeric Transgenic AChE Reaches Cholinergic Brain Synapses

Figure 15:
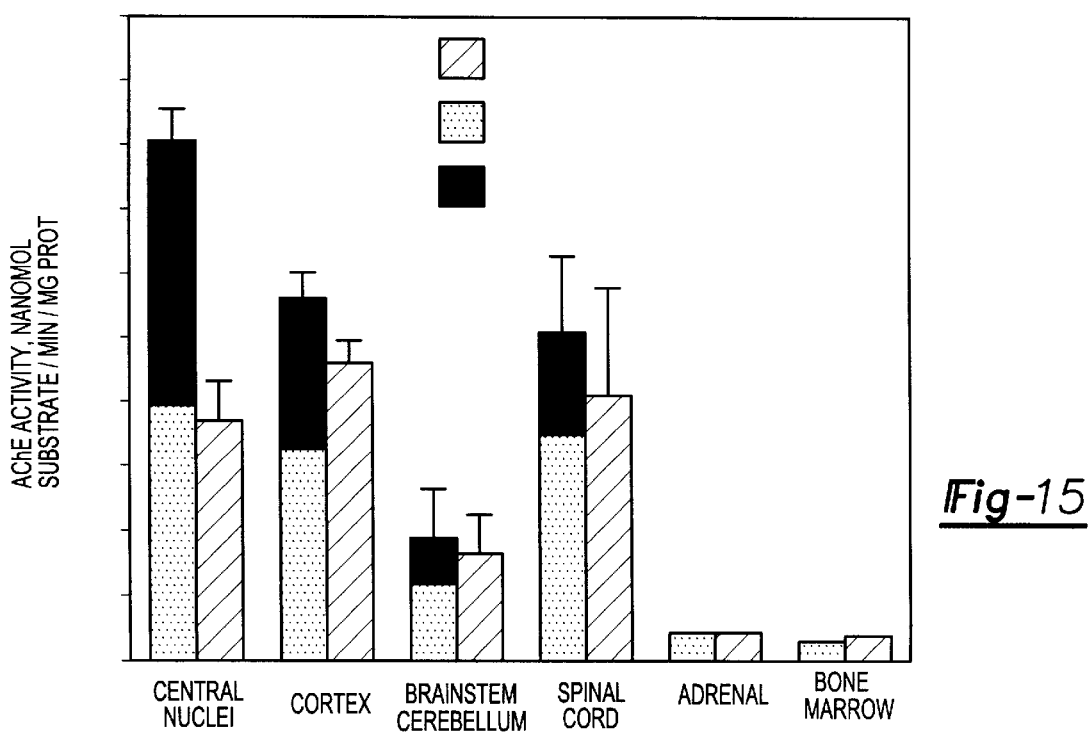
FIG. 15 is a bar graph of AChE activity in brain and different organs, AChE activities were measured with acetylthiocholine as substrate (Seidman et al., 1994)., AChE of human origin was quantified by binding extracts from the noted tissues and brain regions to specific anti-human AChE monoclonal antibodies.

To search for multimeric assembly of the transgenic enzyme, brain region homogenates were subjected to sucrose gradient centrifugation followed by adhesion to immobilized human-selective anti-AChE monoclonal antibodies and measurements of acetylthiocholine hydrolysis levels. AChE from the brain of control and transgenic mice displayed similar sedimentation profiles, demonstrating unmodified assembly into multimeric enzyme forms. Up to 500 of the active enzyme in basal forebrain adhered to monoclonal antibodies specific to human AChE (FIG. 15). Moreover, catalytic activity measurements of antibody-immobilized AChE from tissue homogenates revealed that the transgenic enzyme was present in higher levels within the basal forebrain, whereas more limited amounts of this protein were detected in cortex, brainstem, cerebellum and spinal cord extracts. There were no age-dependent changes in this pattern. Gel electrophoresis followed by cytochemical staining of enzyme activity (Seidman et al., 1995) revealed similar migration for AChE from the brain of transgenic and control mice, indicating comparable glycosylation patterns.

Cytochemical staining of AChE activity was observed in 50 μm brain sections from transgenic mice in all of the areas that showed high AChE activity in homogenate assays. Intense staining was detected in the neostriatum, pallidum and hippocampus. Thus, the extent of excess AChE reflected the brain region distribution characteristic of the primate brain, suggesting that the transgenic mice retained the initial species-specific capacity to regulate human AChE production.

Transgenic AChE Selectively Alters Thermoregulatory Responses to Cholinergic and Serotonergic Agonists Among other functions, cholinergic neurotransmission is involved in controlling body temperature in mammals (Simpson et al., 1994). Applicants ascertained that thermoregulation was properly retained in the transgenic mice by checking their cold adaptation, which remained unchanged. Applicant's then examined hypothermic responses of these transgenic mice to intraperitoneally-injected hypothermia-inducing cholinergic drugs. Core body temperature was reduced by a limited extent and for shorter duration in the transgenic as compared with control mice. This was first examined with the potent AChE inhibitor diethyl p-nitrophenyl phosphate (paraoxon), the toxic metabolite of the agricultural insecticide parathion (Table VI). Most importantly, transgenic mice exposed to 1 mg/kg dose of paraoxon retain apparently normal locomotor activity and behavior, while control mice subjected to this dose presented symptoms characteristic of cholinergic overstimulation.

In addition to their improved, yet predictable, capacity for scavenging of the anti-AChE paraoxon, the transgenic mice also displayed resistance to the hypothermic effects of oxotremorine, an effective agonist of muscarinic receptors (Clement, 1991). They were also resistant to the less potent effect of nicotine, and to the serotonergic agonist 8-hydroxy-2-(di-n-propylamino) tetralin (8-OH-DPAT), but not to the $\alpha_2$-adrenergic agonist clonidine (Table VI). Serotonergic agonists may act directly on serotonin receptors, involved in thermoregulation (Simpson et al., 1994). However, they may also interact with ACh receptors (Garcia-Colunga and Miledi, 1995). Therefore, the altered drug responses may reflect either transcriptional or post-transcriptional changes in ACh (and perhaps serotonin) receptors within the brain of transgenic mice.

In summary, expression of human AChE under control of the 596 bp human promoter and first intron was limited to central nervous system neurons of transgenic mice. This expression changed responses to hypothermic-inducing drugs acting on cholinergic and probably serotonergic receptors. In addition, it created a progressive spatial learning and memory impairment. In contrast, the open field behavior of these transgenic animals remained normal. These findings suggest that subtle alterations in the cholinergic balance may cause physiologically-observable changes and contribute by itself to the memory deterioration in at least part of the patients with cholinergic deficits.

EXAMPLE 5

Further Characterization of Transgenic Animals
Additional Experimental Procedures Testing transcriptional tissue specificity of the hAChE transgene: ACHE mRNA transcripts of human and mouse origin were pursued in spinal cored and muscle RNA extracts from apparently homozygous FVB/N mice carrying the hACHE transgene, as compared with control mice (Beeri et al., 1995). Species-specific PCR primers were designed at nucleotides 1522(+) and 1797(−) in exons 3 and 4 of the human transgene (Soreq et al., 1990) and at nucleotides 1361(+), 1896(−) in exons 3 and 6 of the mouse gene (Rachinsky et al., 1990). Resultant PCR products (276 and 536 bp, respectively) were electrophoresed on agarose gels.

High resolution in situ hybridization: All procedures were carried out at room temp., unless stated otherwise. 50 μl cervical spinal cord sections from transgenic and control mice were fixed with 4% Paraformaldehyde, 0.1% glutaraldehyde (2 hours) and were washed twice, 15 minutes in Phosphate-buffered Saline with 0.1% Tween-20 (PBT) at 4° C. Following gradual dehydration in 25%, 50%, 75% and 100% methanol in PBT (5 minutes each step), sections were kept in 100% methanol at −20° C. until use. Rehydration was with the same methanol/PBT series in reverse order, followed by two 5 minutes washes in PBT. One hour clearing in 5% hydrogen peroxide was followed by 3×5 minute washes in PBT and 15 minutes incubation with 10 μg/ml proteinase K in PBT. Sections were then washed 20 minutes with 2 mg/ml glycine in PBT, and 2×5 minutes with PBT. Following 20 minutes refixation with 4% paraformaldehyde—.02% glutaraldehyde in PBT, and 2×5 minutes washes with PBT, prehybridization solution was added for 1 hour at 52° C. (50% Formamide, 5×SSC (pH 4.5), 50 μg/ml yeast tRNA, 1% SDS 50 μg/ml heparin). This was replaced by the same solution plus 1 μg/ml 50-mer 5' biotinylated 2-0 methyl ACHEcRNA probe (Microsynth, Switzerland) (positions 1932–1981 in mouse exon 6). Hybridization was for 16 hours at 52° C. Post-hybridization washes were 2×30 minutes, 56° C. with solution 1 (50% formamide, 5×SSC (pH 4.5), 1% SDS), 1×10 minutes, 56° C. with 1:1 solution 1:solution 2 (0.5 NaCl, 10 mM TrisHCl pH7.5, 0.1% Tween-20), 3×5 minutes with solution 2 at room temperature., 2×30 minutes with 100 μg/ml RNAse in solution 2 at 37° C., 5 minutes with solution 2, 5 minutes at room temperature with solution 3 (50% formamide, 2×SSC, pH 4.5), 2×30 minutes at 56° C. with solution 3, 3×5 minutes with TBST (136 mM NaCl, 2.7 mM KCl, 25 mM Tris pH 7.5, 0.1% Tween 20, 2 mM Levamisol). To prevent non-specific binding and suppress endogenous alkaline phosphatase, 1% skim milk in TBST and 2 mM Levamisol were added for 1 hour. The ELF 6605 kit (Molecular Probes) was then employed at dilution 1:250 to stain for alkaline phosphatase-streptavidin conjugates.

Staining procedures: For structural NMJ analyses, diaphragm muscles from sacrificed transgenic and control mice were fixed in situ for 5 minutes by fresh 4% paraformaldehyde, 0.1% glutaraldehyde solution in phosphate buffered saline (PGPBS), dissected, refixed for 2 hours and kept at 4° C. in PBS until used for cytochemical AChE staining (Beeri et al., 1995) or with 0.1% methylene blue. Diaphragm regions rich in NMJs were dissected into rectangles of about 3×5 mm, immobilized on glass slides and photographed in a Zeiss Axioplan microscope at ×1000 magnification. Sections of cervical spinal cord (50 μm thick, paraformaldehyde-glutaraldehyde fixed) were stained for 30 minutes and thiocholine precipitates observed by electron microscopy in 80 nm cut stained sections (Seidman et al., 1995). Morphometric measurements were performed as detailed previously (Seidman et al., 1995) using the Sigma Scan program (Jandel, Germany).

AChE activity measurements: Acetylthiocholine hydrolysis levels were determined spectrophotometrically in the present of $1.10^{-5}$ M of the selective butyrylcholinesterase centrifugation and adhesion to a human-selective anti-AChE monoclonal antibody (AC 101.1, Seidman et al., 1995) for 30 minutes.

Electromyography: After general anesthesia (with 60 mg/kg weight Nembutal, injected intraperitoneally) and dissection of the hindleg, a tungsten bipolar stimulating electrode was positioned on the trunk of the sciatic nerve and evoked muscle fiber potentials recorded by a microelectrode placed on the gastrocnemius muscle. The nerve was stimulated by bried (0.1 msec) stimuli at increasing intensities (<1 mAmp). Data was recorded through an AM system, AC-DC amplifier, digitized on line and analyzed (Axon instruments Alon!). In each animal, about 10 different places were recorded and muscle temperature, retained at 32±1° C. by a warming lamp was continuously monitored.

Grip test: Mice were suspended with their forelegs on a 3 mm thick horizontal rope at 1 m height above bench level. The time in seconds it took them to grip at the rope with their hindlegs and escape this uncomfortable situation (performance time) was thrice measured in 1 minute intervals for sex-matched mice with similar body weights. Performance time was recorded as 10 seconds both for unsuccessful trials or for those trials which ended in animals falling off the rope.

Transgenic hAChE is Expressed in Spinal Cord Neurons but not Muscle:

As also shown above, transgenic hACHE cDNA products were clearly detected in spinal cord, but not muscle adult transgenic FVB/N mice carrying two copies of the human ACHE transgene (Beeri et al., 1995). This was done using species-specific PCR primers designed to distinguish between human and mouse ACHE mRNA and extended Applicants previous analyses which indicated limitation of expression of this transgene to the central nervous system (Beeri et al., 1995). Interestingly, direct muscle injection of plasmid DNA containing the parallel rat promoter also demonstrated no expression in muscle fibers (Jasmin et al., 1995). Kinetic follow-up of the PCR amplification showed no apparent difference between mouse ACHEmRNA levels in the spinal cord of transgenic as compared with control mice, suggesting that transcription of this transgene did not affect the expression of the corresponding host gene.

To identify specific ACHE-expressing cell types within the spinal cord, Applicants employed a high resolution wholemount in situ hybridization technique. To this end, a 5' biotinylated 50-mer ACHEcRNA probe was synthesized with 2-O-methyl chemical modification in its internucleotide bonds. In addition to enabling immediate sensitive detection by avidin conjugates, this ensured tighter hybridization and thus better specificity than that provided by unmodified cRNA (Kawasaki et al., 1993), as well as protection of Applicants cRNA probe from nucleolytic (Eckstein, 1985). Using this method, Applicants detected ACHE mRNA transcripts spread throughout the perikarya and the apical end of processes in neurons of apparently similar distribution and numbers in spinal cord sections from both transgenic and control mice, suggesting that hAChE expression did not damage neuronal proliferation and/or survival. Cresyl violet staining confirmed that cell distribution, number and shape remained largely unmodified. ACHE mRNA transcripts appeared both in large (>20 μm diameter) polygonal neurons with the characteristic features of α motoneurons (Jones et al., 1993) and in smaller (<10 μm diameter) round cells resembling interneurons cytochemical staining further demonstrated conspicuous AChE expression in neuronal perikarya and processes of transgenic spinal cord. Parallel analyses of successive spinal cord sections demonstrated similar patterns of ACHE mRNA labeling in various spinal cord regions and revealed no labeling in cells with glial morphology, in agreement with observations of others (Hietanen et al., 1990) and with Applicants own brain analyses in these transgenic mice (Beeri et al., 1995).

Axo-dendritic Cholinergic Spinal Cord Synapses Remain Largely Unmodified in Spite of hAChE Accumulation Axo-dendritic Cholinergic synapses labeled by the electron dense crystals of the AChE reaction product revealed principally similar axon diameter, pre-synaptic length and a number of adjacent mitochondria in transgenic and control animals (Table VII), stressing forward the mild nature of the change enforced by this transgene. In contrast, synaptic areas occupied by AChE reaction products (Table VII) were 7-fold larger in transgenic spinal cord sections, whereas the presynaptic area occupied by vesicles was only slightly smaller in transgenic synapses than in control terminals (Table VII). However, there was no sign of neuronal degeneration such as fibrillary bodies. Thus, transgenic AChE expression in spinal cord neurons was associated with massive enlargement in synaptic AChE stained areas but did not substantially change other morphometric parameters in cholinergic axo-dendritic synapses within this brain region.

Globular Enzyme Tetramers Containing Transgenic AChE Reach Muscle

Normal processing of transgenic motoneuron AChE should transport it to NMJ, where it contributes to the general pool of muscle and NMJ AChE activities. To characterize the biochemical properties of motoneuron-originated AChE in NMJ, Applicants centrifuged low salt-soluble as well as detergent-soluble spinal cord and muscle extracts and measured AChE activities in the resultant sucrose gradient fractions, transgenic enzyme being identified by immobilization onto monoclonal antibodies (Seidman et al., 1995). AChE activity in spinal cord extracts of transgenic animals, 208 nmol/min/mg protein, was 25% higher than that of control animals, due to human originated AChE evenly distributed between the low salt-soluble and the detergent soluble fractions. Detergent-soluble AChE in the spinal cord consisted mainly of globular tetramers (G4), with minor fractions of monomers (G1) and dimers (G2). The G4 enzyme peak in transgenic mice was considerably higher than in controls and included 18% of human-originated enzyme. In contrast, no significant increment was observed in the considerably lower total muscle AChE activities (33,4±6.9 nmol/min/mg protein, n=7 animals). However, whereas detergent-soluble spinal muscle AChE in control animals was composed of approximately equal parts of $G_1$ and $G_4$ enzyme, the $G_4$:/$G_1$ ratio was 2-fold higher in transgenics. Antibody immobilization further revealed both G4 tetramers and some monomers of human origin in this detergent-soluble fraction, altogether 6% of total muscle AChE activity which was contributed by the motoneuron-expressed transgene. Considering the fact that NMJs represent less than 0.1% of the muscle surface (Hall, 1995) this increase reflected a significant accumulation of the transgenic enzyme in the synaptic microenvironment.

Neuromuscular Junctions of Transgenic Animals Undergo Dramatic Morphological Changes Cytochemically stained areas of diaphragm endplates were 60% larger than control NMJs (Table VII.B). This increase reflected general structural changes, as it was also observed with the non-specific dye methylene blue, with over half of transgenic endplate areas but only 10% of control ones being larger than 600 $\mu m^2$. In addition, 82% of 161 transgenic endplates from 4 animals resumed a simple ellipse-like aspect and lost the classical "pretzel" boundaries (Lyons and Slater, 1991) found in 82% of 172 endplates from 4 control animals. Moreover, muscle fiber diameters were 15% larger in transgenics compared to controls (p<0.0001, Student's t test) (Table VII.B). Similar morphological changes were also found in hindleg quadriceps endplates and in anterior tibialis muscles.

Electron microscope analyses of diaphragm preparations, stained with methylene blue for localization of the junctional regions, revealed in the transgenic animals highly variable NMJs. These either possess short, undeveloped post-synaptic folds resembling those of myasthenic patients (Engel and Santa, 1971) or developed highly exaggerated, branched and densely packed post-synaptic folds, similar to those occurring in the Eaton-Lambert syndrome (Lambert and Elmqvist, 1971). Neither of these aberrations appeared in sex and age-matched control animals (Table VII.B), yet similar changes were reported in NMJs of aged humans (Wokke et al., 1990).

Degeneration of muscle fibers in adult transgenic animals was first observed by macroscopic analysis. Optic and electron microscopy consequently indicated general loosening of intracellular structures. Cell space was filled with large, structureless vacuoles. The distances between myofilaments and between myofibrils was enlarged. Triads of T-tubules and terminal cisternae appeared dissociated, mitochondria were no longer aligned with I-bands of the sacrolemma and were clearly swollen, with invisible cristae. Post-synaptic abnormalities within the muscle tissue were therefore far more dramatic than those observed in the spinal cord itself, in spite of the lack of transgene expression in muscle.

Transgenic hAChE Expression Leads to Electromyographic Abnormalities

Direct recording on the gastrocnemius muscle with a unipolar tungsten electrode did not reveal any spontaneous denervation activity. However, after stimulation of the common trunk of the sciatic nerve, the recorded muscle fiber potentials presented three main abnormalities. First, muscle potentials were of bigger intensity and duration compared to those of age and sex-matched controls, with frequent multiwaved shapes (mainly three subpeaks), rarely seen in controls. Second, repetitive supramaximal stimulations at 1 Hz induced pathological late potentials (latency up to 40 ms) which appeared frequently in transgenic animals but very rarely in controls. Finally, progressive increase of stimulation intensity led to pronounced increases of response intensity in transgenic as compared with control mice, reflecting abnormal enlargement of motor units. In addition, in 2 of 4 cases, 3 HZ stimulations following tetanization by 300 stimulations at 30 Hz resulted in myasthenia-like decreases in the intensity of responses in transgenic but not control animals. However, the intensity response recorded on the surface of the sciatic nerve did not differ between controls and transgenic mice, and no late potentials were detected in these measurements. Electromyographic measurements thus confirmed and extended the morphological observations, pointing at complex neuromuscular abnormalities.

hAChE-Induced Progressive Impairments in Muscle Functioning

Figure 16:
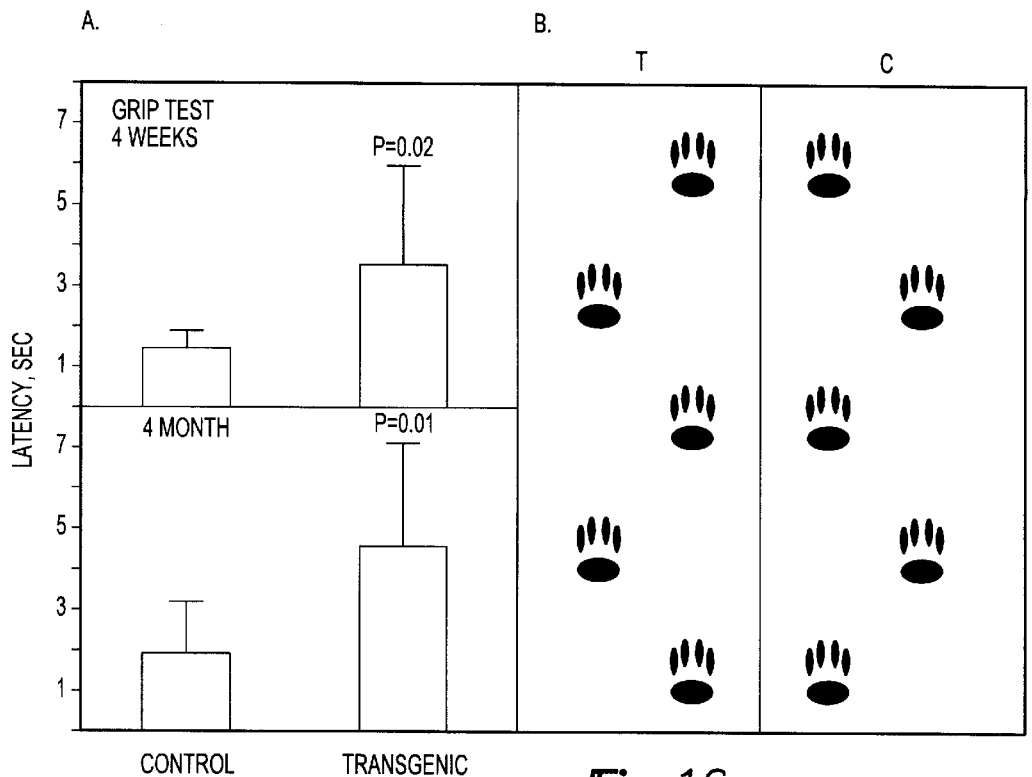
FIGS. 16A–B are graphs showing (A) Adult Transgenic displaying normal walking traces with no obvious sign of pathological gait, as shown by representative walking traces in a tunnel, left on paper by 5 months old mice whose feet were dipped in ink, T: transgenic, C: control. One out of 10 experiments and (B) Trunk and hindlegs weakening wherein mice were suspended with their forelegs on a 3 mm diameter rope and their ability to grip at the rope with their hindlegs was noted.

Transgenic animals walked normally, with similar track width and pace length to those of controls (FIG. 16A). Mean swimming speed was also similar (24.86±4.1 m/min in 10 controls compared to 21.40±3.97 m/min in Q transgenics. However, transgenic animals performed worse than controls in a rope grip test. This deficiency was already significant (P<0.02) at the age of 4 weeks but worsened (P<0.01) at 4 months of age, concomitantly with muscle amyotrophy. Moreover, when hung on the rope with their front legs, they acquired a totally loose posture; and 4 months old transgenics, but no control animals fell off the rope altogether (in 20% of 30 sessions and 10 animals), reflecting deficient capacity of their forelegs in addition to weakened trunk and hindlegs. This, in addition to diaphragm NMJ abnormalities, was perhaps the reason for the abnormal mortality rate in these transgenic mice (5 of 150 mice below 10 months as compared with no mortality in controls).

Neuromuscular Junctions Appear more Vulnerable than Spinal Cord cholinergic Synapses to hAChE Overexpression Transgenic overexpression of human AChE in spinal cord neurons but not muscle induced only moderate modifications in cholinergic spinal cord synapses yet caused the appearance of enlarged, abnormally shaped NMJs and degenerating, wasting muscle fibers with abnormal electromyographic properties and progressively worsening neuromuscular deformities, implying that nerve-nerve cholinergic synapses do not succumb to the same regulations as NMJs in responding to transgenic overexpression of this synaptic protein.

Cytochemical staining of axo-dendritic cholinergic synapses in the transgenic spinal cord revealed a 7-fold excess in synaptic enzyme activities, close to the excess observed in NMJs of transiently transgenic Xenopus tadpoles expressing the same hAChE transgene (Ben Aziz Aloya et al., 1993; Shapira et al., 1994; Seidman et al., 1995). This can perhaps suggest an upper limit for AChE excess compatible with synapse infra-structure. Interestingly, characteristic morphometric parameters of spinal cord synapses such as axon diameters, pre-synaptic length and mitochondria densities remained grossly unchanged.

That the space occupied by pre-synaptic vesicles was only slightly reduced, unlike the drastic changes occurring under $\beta_2$-laminin disruption (Hall, 1995) indicates that AChE is not primarily involved in determining the amount of vesicles within NMJs. In addition, this limited change does not exclude the possibility of feedback regulation processes compensating for the consequences of excess AChE expression. Moreover, transgenic mice displayed generally regular motor behavior as long as no special muscle efforts were required of them, suggesting that base level normal NMJ functioning was sustained, unlike that observed under changes in dystrophin properties (Koenig et al., 1987). Finally, the 25% increase in spinal cord AChE activities did not alter the distribution and number of AChE-expressing neurons in the spinal cord of transgenic mice. This excludes AChE from being involved in neuronal survival, unlike CNTF (Masu et al., 1993). The morphogenic effects of the ACHE transgene in the spinal cord were thus more limited than those of any of the above proteins, yet sufficient to cause progressive muscle deterioration in the adult animals.

Mouse and Xenopus NMJs Respond Similarly to Transgenic hACHE Expression

NMJ structures in the transgenic mice covered 50% larger areas than controls, lost their sharp boundaries and characteristic pretzel shapes and developed either highly exaggerated or small, degenerate post-synaptic folds. In Xenopus NMJs, hAChE overexpression induced elevation of muscle nicotinic acetylcholine receptor levels and increased the length and width of transgenic NMJs in a manner dependent on pre-synaptic expression of the human transgene (Shapira et al., 1994; Seidman et al., 1995). That hAChE-expressing NMJ areas were similarly enlarged in these two evolutionary distant vertebrate species strengthens Applicants assumption that maximal overexpression levels compatible with life were reached and identifies AChE as a universal morphogenic element of NMJs. Exaggeration of post-synaptic folds also occurs in the Eaton-Lambert syndrome (Lambert and Elmqvist, 1981), where the functioning of pre-synaptic $Ca^{++}$ channels is impaired and acetylcholine secretion and post synaptic receptor activation are decreased. This suggest that a parallel decrease in activation of acetylcholine receptors also occurs in the nerve terminal of Applicants transgenic mice. Moreover, degenerated post-synaptic folds appear in NMJs of myasthenia gravis patients, where post-synaptic ACh receptors are blocked by antibodies (Engel and Santa, 1971). Changes in the level of activated acetylcholine receptors thus occur in both syndromes with NMJ malformations resembling those of Applicants mice.

NMJ Alterations are Associated with Muscle Deformities

The morphological NMJ changes further imply modulations in the downstream input of cholinergic signals into muscle, the ultimate target of the motor system. Whereas muscle is known to contribute the collagen-tailed AChE forms soluble in high salt and detergent (Massoulie et al., 1993), Applicants' present findings pinpoint at a significant fraction of the detergent-soluble globular AChE tetramers as neuronal-originated; this, in turn, attributes the exercise-induced increases in G4AChE (Jasmin and Gisiger et al., 1991) to motoneuron transcriptional response in addition to muscle overexpression. The significant changes in AChE levels have further led to muscle weakening and amyotrophy observed in adult transgenic mice. That general motor behavior in these animals was apparently normal at rest could reflect compensation to these abnormalities, for example, by increasing endplate space and synaptic cleft volume. Recent theoretical calculations, based on morphometric measurements of NMJs in adult lizard (Anglister et al., 1994) postulated that increasing AChE concentration by up to 2-fold should have no consequences on cholinergic signaling. Whether the clearly abnormal phenotypes Applicants observe are due to the significant AChE excess in the synaptic microenvironment, to the long-term effect of this excess, to its embryonic appearance or to species-specific distinctions in all of these should be further investigated. In any event, Applicants' findings demonstrate that a moderate increase in the motoneuron expression of AChE, a detrimental component of synapse functioning, is sufficient to alter not only NMJ function, but also its mode of development and its permanent structure.

Electromyography Analyses Indicate Abnormal Innervation

The dramatic increment in normalized muscle action response to increased stimulus intensities implies that larger numbers of muscle fibers were activated by the motor neurons excited in these single events. Since the motor neuron response remained apparently unchanged, this further indicates that each motor neuron extended more terminals to contact transgenic muscle fibers than under normal conditions. Similar abnormalities occur both in motor neuron lesions and in neuromuscular diseases such as the Eaton-Lambert syndrome (Eaton and Lambert, 1957) or in prior diseases (Westaway et al., 1994).

The hAChE-Induced Phenotype Progresses with Age

The progressive loss of motor functions in Applicants' transgenic mice resembles the progressive deterioration of learning and memory observed in these mice previously (Beeri et al., 1995). Since muscle weakening is associated with the advanced stages of Alzheimer's disease (Thomas et al., 1982), of certain prion diseases (Westaway et al., 1994) of Eaton-Lambert syndrome and of acquired and congenital myasthenias, Applicants conclude that cholinergic imbalance per se can actively contribute to abnormalities in both cognitive and motor functions, with the resultant abnormal phenotypes worsening with age. The increase in muscle fiber and motor unit size, appearance of pathological late potentials and even the unexplained mortality in these mice could all be due to such imbalance. However, Applicants cannot rule out the possibility that part of these abnormalities can be due to the expression of the AChE transgene in higher brain areas associated with motor function. That myasthenia gravis patients experience stable sustenance of muscle functioning under treatment with the AChE inhibitor pyridostigmine may therefore indicate that parallel therapeutic approaches can be beneficial also to patients with neurodegenerative diseases associated with cholinergic imbalance.

EXAMPLE 6

PHOTORECEPTOR DEGENERATION IN DEVELOPING RETINA OF ACETYLCHOLINESTERASE-TRANSGENIC MICE

The vertebrate retina contains a highly structured cholinergic network (reviewed in Marc, 1986; Hutchins, 1987). Retinal cells synthesizing acetylcholine comprise two populations of amacrine cells, one found in the ganglion cell layer (GL) and the other at the inner nuclear layer (INL) (Vaney et al., 1981; Masland and Tauchi, 1986). These cells form synaptic connections with ganglion cells in one of two planes within the inner plexiform layer (IPL). Proposed functions of acetylcholine in the retina include control of the directional selectivity of ganglion cells (Ariel and Daw, 1982a,b), presynaptic modulation of glutamate release by axons of retinal ganglion cells (Freeman, 1977; Langdon and Freeman, 1987; Schmidt, 1988), and regulation of outgrowth of ganglion cell processes (Lipton et al., 1988).

To examine the consequences of synaptic cholinergic imbalance on retinal function and development, transgenic mice expressing human (h), in addition to endogenous acetylcholinesterase (AChE) were studied. These mice appear normal at birth and develop as well as controls, but ultimately suffer progressive cognitive and neuromotor deterioration (Beeri et al., 1995; Andres et al., 1996), associated with neuronal excess of the brain and muscle form of AChE as shown in the above Examples. Applicants found that hAChE-transgenic mice exhibit a rapid degeneration of retinal photoreceptors during the second postnatal week (rods first and then cones). The time course of this degeneration is highly correlated with a transient increase in catalytically active hAChE mRNA and protein levels within the inner retina of developing transgenic mice, corresponding to the expression of endogenous AChE. As AChE levels are frequently subject to alterations due to internal and external causes, this study suggests one possible mechanism leading to retinitis pigmentosa with yet unknown genetic origins.

Additional Methods

Tissue Preparation. FVB/N transgenic mice were confirmed by PCR analysis to carry the transgene encoding the brain and muscle form of hAChE (Beeri et al., 1995). Eyes were quickly removed from sacrificed control and transgenic mice at noted postnatal days (P) (n=2–17 per age). The eyes were either immediately frozen in liquid nitrogen for use in PCR and biochemical analyses, or incubated in 4% paraformaldehyde overnight at 4° C. for use in TUNEL, histological and immunohistochemical analyses, in which case, they were post-incubated in 30% sucrose for cryoprotection and then frozen in embedding medium on dry ice for sectioning. Eye sections were cut on a cryostat (20 μm) in the transverse plane and mounted onto gelatin-coated slides. Sections were stored desiccated at −20° C. until use.

Fragmenting DNA was labeled with the TUNEL technique of Gavrieli et al. (1992), with slight modification. Briefly, after a 10 minute wash in TdT buffer (3 mM Trizma base, 14 mM sodium cacodylate, 0.11 mM cobalt chloride), slide-mounted sections were incubated in a humid chamber at 37° C. for 1 hour with a mixture of terminal deoxytransferase (TdT, Boehringer-Mannheim) (0.03eu/μl) and biotinylated dUTP (BIO-16-dUTP, Boehringer-Mannheim) (4 μM) in TdT buffer. Following preincubation in PBS containing 1% bovine serum albumin (15–20 min), sections were incubated with streptavidin-conjugated indocarbocyanine (Cy3, Jackson Immunoresearch, diluted 1:1000 in PBS, 1 h). Sections were also incubated for 2 hours at room temperature with FITC-conjugated Griffonia simplicifolia lectin (Sigma Chemical Co., St. Louis, Mo., diluted 1:1000 in PBS) to label blood vessels and microglia. They were then washed in PBS and mounted in PBS/glycerol/gelatin.

For immunohistochemistry, eye sections were preincubated in PBT buffer (phosphate buffered saline, and 0.3% Triton X-100) containing 10% goat serum (GS) for 1 hour at room temperature, washed and incubated overnight at 4° C. with selective anti-hAChE mabs (mAb 101-1, 101-2, diluted 1:200) (Seidman et al., 1994) as described (Hamassaki-Britto, 1994). Washed sections were incubated with an anti-mouse IGg, biotinylated-antibody (diluted 1:100, 1 hour, room temperature) and then with a mixture of biotin and avidin-peroxidase for 30 minutes (ABC Elite Kit, Vector Labs, Burlingame, Calif.). Following wash, the tissue was reacted with diaminobenzydine plus hydrogen peroxide (Sigma Chemical Co., St. Louis, Mo.) for 10 minutes and coverslipped. Histochemical staining for AChE catalytic activity and transmission electron microscopy were as previously described (Ben Aziz-Aloya, 1993), except that the incubation for slide-mounted frozen sections was for 2 hours.

For enzyme assays, tissue extracts were prepared from one or two eyes and total AChE activity per mg protein determined with a standard colorimetric assay adapted to a 96-well microtiter plate (Neville et al., 1992). To distinguish between hAChE and endogenous mouse AChE, an enzyme-antigen immunoassay (Liao et al., 1992) was used as described (Loewenstein-Lichtenstein et al., 1995).

PCR Amplification. For RT-PCR analysis, total RNA was extracted from eyes by the guanidinium thiocyanate method as described (Soreq et al., 1990). cDNA was prepared from 0.2 mg RNA of each sample using MMLV reverse transcriptase (Gibco, BRL, Bethesda, Md.), essentially as described by Lapidot-Lifson et al., (1992). PCR amplification was as described (Karpel et al., 1994), except that the annealing temperature for hAChE was 69° C. Species-specific PCR primers were designed as follows. Resultant PCR products were removed at the noted cycle numbers and electrophoresed on agarose gels.

Species-specific PCR primers were designed for human AChE mRNA at nucleotides 1522(+) and 1797(−) in exons 3 and 4 of the transgene (Beeri et al., 1994), mouse AChE at nucleotides 375(+) and 1160(−) (Rachinsky et al., 1990), mouse ChAT at nucleotides 83(+) and 646(−) (Misawa et al., 1992), mouse $\alpha_7$ nAChR subunit at nucleotides 1002 (+) and 1443(−) (Orr-Urtreger et al., 1995), rat $\alpha_3$ nAChR subunit at nucleotides 88(+) and 507(−) (Boulter et al., 1986), rat $\alpha_4$ nAChR subunit at nucleotides 181(+) and 600(−) (Goldman et al., 1987), mouse ml mAChR at nucleotides 130 (+) and 519 (−) (Shapiro et al., 1988) and mouse actin at nucleotides 822(+) and 966(−).

Chronic DFP treatment. Transgenic mouse pups, aged P0–P15 (n=19) were housed with the dam in a light- and temperature-controlled room. All pups were pretreated with 10 mg/kg IP atropine sulphate (Sigma Chemical Co., St. Louis, Mo.) in saline 15 minutes before injections. DFP (diisopropylphosphorofluoridate, Aldrich Chemical Co., Milwaukee, Wis.) was dissolved in corn oil and injected once daily SC (1.0 mg/kg) during the first 2 weeks postnatal. Control animals received the corn oil vehicle. Exposure to higher doses of DFP (2–3 mg/kg) at any postnatal age resulted in mortality. At P15, about 4 hours after the last DFP injection, pups were sacrificed and their brain and eyes removed for biochemical and histological analyses.

Data Analysis. All retinal sections were analyzed and photographed at the mid-central retina, close to the optic nerve. Data were examined by two-way ANOVA, followed by Newman-Keuls post hoc comparisons.

RESULTS

Degeneration of Photoreceptors. Nissl-stained retinal sections from control and age-matched transgenic mice were examined at various postnatal ages. No obvious morphological difference between control and transgenic retinas was detectable, at the light microscopic level, up to 10 days of age. However, by P12, the outer nuclear layer (ONL) in transgenic retinas exhibited a reduction in width as compared to control, which was accompanied by an abnormal increase in cellular apoptosis within the transgenic ONL. By P20, transgenic retinas showed complete loss of photoreceptor inner and outer segments, while the ONL was 10-fold reduced to a single nuclear layer. The ONL was no longer distinguishable in transgenics by P60.

Developmental Expression of hAChE. To determine whether a correlation existed between the time course of retinal degeneration and the level of transgene expression, hAChE protein and mRNA levels were analyzed in developing eyes from transgenic and control mice. mabs shown to specifically recognize human AChE (Seidman et al., 1994) were used unfrozen-section preparation. These mAbs labeled both extra- and intracellular pools of hAChE, as evident by staining of both plexiform and nuclear retinal layers (Ramirez et al., 1989), corresponding to histochemical staining of total AChE activity.

At P10, light immunocytochemical staining was observed in the inner plexiform layer (IPL), while stronger staining was observed in the axon (AL) and ganglion cell (GL) layers. A similar pattern of staining for AChE activity was observed in both transgenic and control retinas at this age, except that subbands of labeling were clearly distinguished with this, more sensitive technique. By P20, immunocytochemical staining for hAChE was increased in the transgenic IPL, while strong staining of the GL and AL was still evident. A corresponding increase in AChE activity was observed at this age, showing distinct subbands of labeling in the control, but not the transgenic IPL. By P60, immunocytochemical staining of AChE was decreased in the transgenic IPL, GL and AL, however, strong AChE activity was still observed in the IPL. Sections of retina from control mice showed no specific immunocytochemical staining for hAChE. Staining within the pigment epithelium and choroid layers was often observed in control as well as in transgenic retinal sections that were not exposed to primary antibody, and was thus attributed to non-specific labeling.

Figure 17:
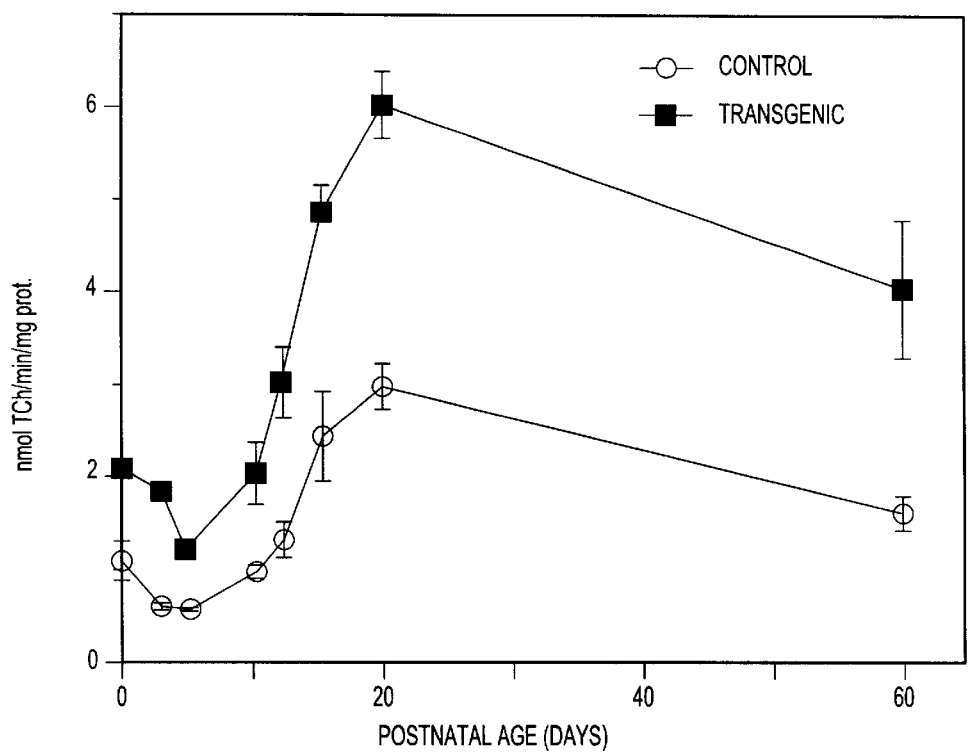
FIG. 17 is a graph showing catalytic activity of total AChE in control (open circle) and transgenic (square) developing mouse eyes, Data represent the mean ± SEM for three to five animals.

Quantitative analysis of AChE catalytic activity in both control and transgenic mouse eyes demonstrated constant levels of activity from P0 to P10 (FIG. 17). By P20, AChE activity levels exhibited a 3-fold increase followed by a significant decline in activity into adulthood ($F_{7,48}=31.87$; $p<0.0001$; two-way ANOVA). This transient developmental expression of AChE activity showed similar patterns in control and transgenic eyes. However, AChE specific activity in transgenic eyes was 2-fold higher than in control eyes throughout development ($F_{1,48}=115$; $p<0.0001$). Enzyme-antigen immunoassay analysis demonstrated that approximately 80% of the total AChE catalytic activity in developing transgenic eyes was due to the human enzyme.

A parallel transient increase in AChE mRNA levels was observed within retinas of developing control and transgenic animals. Levels of both hAChE mRNA and mouse AChE mRNA increased and peaked at P10, and then declined to adult levels. This suggests that both genes are developmentally regulated by the same mechanism(s). Interestingly, host AChE mRNA levels within transgenic animals were vastly lower than hAChE mRNA levels. In addition, host AChE mRNA levels were slightly lower in transgenic than control animals. This observation, together with the high percent ratio of hAChE activity indicates a decline in endogenous AChE levels in transgenics. The mRNA levels for various cholinergic elements were evaluated for further, potential compensatory cholinergic response. Levels of mRNA for mouse choline acetyltransferase (ChAT), $\alpha_7$, $\alpha_3$, and $\alpha_4$ nicotinic acetylcholine receptor (AChR) subunits and the m1 muscarinic AChR exhibited no difference between transgenic and control animals.

Oxygen Metabolism. The pattern of blood vessels within the retina was analyzed in order to determine whether the photoreceptors were exposed to hypoxic conditions during development. No difference in the pattern of blood circuitry was observed between control and transgenic retinas. Moreover, exposure of developing hAChE-transgenic mice to hyperoxia from P6–P20 did not result in significant rescue of retinal photoreceptors.

Chronic Inhibition of AChE Catalytic Activity. In an attempt to rescue photoreceptor degeneration, AChE-transgenic pups were chronically exposed during their first two weeks postnatal to DFP, an irreversible inhibitor of AChE. Transgenic animals injected daily with DFP exhibited an 80% reduction in brain AChE activity (11.6±0.5 nmol/min/mg protein) over their vehicle-injected siblings (54.1±6.9 nmol/min/mg protein). DFP-treated animals also showed a great reduction in histochemical staining for AChE activity within the IPL of their retinas. However, there was no significant rescue of photoreceptors within retinas of DFP-treated pups (Note that dark rearing also did not rescue the pups).

Electron Microscopic Analysis. In order to characterize the potential mechanism leading to photoreceptor degeneration, control and transgenic retinas were analyzed at the ultrastructural level, focusing mainly on the IPL. Control retinas showed a network of neuronal processes coursing through the IPL, with large regions that were devoid of any processes. However, transgenic retinas revealed a much higher density of neuronal processes in the IPL, exhibiting less regions of vacancy. Furthermore, processes in transgenic IPL were morphologically thicker than in control retinas and showed a broader area of synaptic contact.

In summary, the transgenic mice expressing human, in addition to endogenous AChE exhibit a rapid degeneration of retinal photoreceptors during the second postnatal week. The time course of this degeneration is highly correlated with a transient increase in catalytically active hAChE mRNA and protein levels within the inner retina of developing transgenic mice, corresponding to the expression of endogenous AChE. Although this overexpression of AChE suggests a decrease in cholinergic transmission, there appeared to be no compensatory changes in host ChAT, nicotinic or muscarinic AChR mRNA levels in transgenic animals as compared to controls. Furthermore, injections of the irreversible AChE inhibitor, DFP, into transgenic mice during the first two weeks postnatal failed to rescue retinal photoreceptors. Ultrastructural analysis revealed a high density of disorganized dendritic outgrowth within the IPL of developing transgenic retinas.

The retinas of the postnatal hAChE-transgenic mice expressed a two-fold increase in catalytically active AChE over control retinas, suggesting a reduction in ACh levels causing an inherent cholinergic imbalance. As shown in the Examples herein, transgenic expression of hAChE in embryonic Xenopus and mouse neuromuscular junctions (NMJ), leading to cholinergic hypofunctioning, results in ultrastructural changes in NMJs accompanied by an increase of nAChR binding and ChAT mRNA levels (Shapira et al., 1994; Andres et al., 1996). However, except for a slight decrease in endogenous AChE, retinas from the transgenic mice of the present invention showed no compensatory changes in the mRNA encoding for several key cholinergic elements. Moreover, photoreceptor degeneration within these retinas was unaffected by chronic DFP exposure. The selective degeneration of retinal photoreceptors in hAChE-transgenic mice presents an enigma, considering that both hAChE expression and its consequences were focused in the inner retina. Cholinergic amacrine cells found in the INL are not known to contact photoreceptors (Masland and Masaki, 1986). Thus, it is unclear how a change in INL circuitry, caused by a ubiquitous enzyme like AChE, can have such a drastic effect on photoreceptors.

Several naturally occurring and transgenic mouse strains, carrying mutations in key proteins involved in phototransduction, have been found to exhibit early retinal photoreceptor degeneration (Pittler and Baehr, 1991; Connell et al., 1991; Sung et al., 1994). Along with mutation and genetic localization studies (Shastry, 1994), these mouse strains have helped characterize the genomic origin of approximately 30% of all cases of autosomal dominant retinitis pigmentosa (adRP). Recently, a new locus has been discovered for early-onset adRP on chromosome 7q (Jordan et al., 1993). Interestingly, this region contains the hAChE gene at position 7q22 (Ehrlich, 1992). Although genetic linkage studies suggest that the gene responsible may be blue cone pigment (BCP) at 7q31–35 (McGuire, et al., 1995), its involvement in this particular case of adRP (Jordan et al., 1993) is believed unlikely. However, the transgenic mouse model exhibited complete photoreceptor degeneration at an early developmental stage, similar to the adRP family examined by Jordan and coworkers (1993). Furthermore, photoreceptor cell death occurred by an apoptotic mechanism, similar to that seen in other RD mouse models (Lolley et al., 1994). This suggest that AChE overexpression in the retina, resulting in disorganized circuitry, may indirectly trigger a general self-destruct mechanism in photoreceptors at a critical period of their development. Hence, the results of this study have important implications for AChE as another possible candidate gene for adRP.

Throughout this application various publications including patents are referenced. Full citations for the publications referenced are listed below and patents are referred to by number. The disclosures of these publications including patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

Central and Peripheral consequences of transgenic overexpression of human AChE

| Property | Xenopus laevis tadpoles | adult transgenic mice |
|---|---|---|
| 1. Transgene - host DNA interaction | None reported | Stable integration |
| 2. Duration of transgene expression | Transient, embryonic | Indefinite, embryonic and adult life |
| 3. Synaptic accumulation | +(with 3'-exon 6) | +(with 3'-exon 6) |
| 4. Effects on NMJ structure | Increased post-synaptic length Wider synaptic cleft | Increased synapse area Changes inpost-synaptic folds |
| 5. NMJ function | Double α-bungarotoxin binding. visual observation of abnormal swimming pattern (Kaufer-Nachum and Soreq, unpublished). | Delayed potentials; Enlarged motor units; Post-excitation fatigue; Progressive deterioration |
| 6. CNS cholinergic synapses | Synaptic accumulation | Synaptic accumulation Acquired resistance to hypothermia induced by anti-AChEs and cholinergic agonists Progressive deterioration of learning and memory |

TABLE II

| Promoters | CMV | HpACHE |
|---|---|---|
| Number of microinjections | 70 | 40 |
| Number of pedigrees carrying the transgene | 1 | 3 |
| Number of DNA copies in each pedigree | 3 | 2-10-15 |
| Pedigrees expressing the transgene | 0 | 1-0-0 |

TABLE III

Immunoadsorption of catalytically active human AChE produced in the Brain of Transgenic Mice

| Homogenate None | Control Mouse | 12F2-σ1 | 13F2-σ10 | Recombin. HAChE |
|---|---|---|---|---|
| ATCH hydrolysis 0.573 mOD/min 0.557 | 0.947 9.947 | 1.270 1.160 | 3.967 4.397 | 16.15 4.397 |

TABLE IV

| Mice | Age | Lymphocytes % | Myoblasts % | Granulocytes % | Eosinophils % | Erythroblasts Normoblasts % | Copy No. | Cells |
|---|---|---|---|---|---|---|---|---|
| C1(m) | | 20.0 | 23.66 | 38.66 | 0.66 | 17.33 | — | 300 |
| C2(f) | | 24.0 | 27.66 | 35.66 | 0 | 12.33 | — | 800 |
| C3(m) | 7 w | 11.1 | 33.1 | 26.0 | 0.4 | 29.4 | — | 950 |
| C4(f) | 7 w | 6.6 | 41.2 | 24.3 | 0.7 | 27.2 | — | 800 |
| C5(f) | | 16.7 | 30.00 | 34.00 | 1.66 | 17.66 | — | 300 |
| C6(f) | 3.5 m | 19.66 | 32.66 | 24.5 | 0.5 | 23.16 | | |
| C7 | | 9 | 35.0 | 24.5 | 2.0 | 29.5 | | |
| #13 [Fo,f] | 5 m | 12.0 | 35.66 | 19.66 | 0.33 | 32.33 | 2 | 300 |
| 13-2 [FI,m] | 7 w | 27.8 | 37.9 | 1.0 | 0 | 33.3 | 2 | 800 |
| #13-10 [FII,f] | 7-8 w | 11.33 | 35.33 | 27.0 | 2.0 | 23.66 | 2 | 300 |
| #8 [Fo,m] | 5.5 m | 17.0 | 24.33 | 26.66 | 0.66 | 31.33 | 1 | 300 |
| #12-1 [FII,f] | 7-8 w | 24.0 | 21.66 | 30.33 | 1.66 | 25.33 | 15 | 300 |
| #8-8 [FII,m] | 11-12 w | | | | | | | 1 |
| #13-11 [FII,f]p | | | | | | | | 2 |
| #12-2 [FII, f]p | 12 w | 23.5 | 24.5 | 18.5 | 0 | 33.0 | 15 | |
| #13-4 [FII, f] | 3 m | 14.0 | 32.5 | 15.5 | 10.5 | 27.5 | 2 | |
| #12-6 [FII, m] | 8 w | 14.0 | 360.0 | 23.5 | 2 | 24.5 | 15 | |
| Average Normal Range (Theoretical) | | 12–20 | 25–35 | 35–45 | 0.5–2.5 | 18–25 | | |

Abbreviations Used: f = female; m = male; p = pregnant; w = weeks; m = months
Differential cell counts were determined in percentage by observing cell shape, size and histochemical staining for each of the noted mice. Note distinct variations in differential cell compositions of the transgenic mice as compared with controls.

TABLE V

| Animal Number & Treatment | Colony Counts | Cell No. $\times 10^5$ | Mφ | PMN | E Ltd. Megs | E Megs | Ltd. RBC | Lt. RBC | Total Cells | Exp No. |
|---|---|---|---|---|---|---|---|---|---|---|
| Ch untreated | | | 16 | 14.9 | 8.1 | 2.4 | 25.5 | 33.1 | 592 | 165 |
| 12F2-1 & 13F | | | 29.1 | 40.4 | 3.9 | 1.9 | 13.2 | 11.6 | 1269 | |
| 2 10 C7 untreated | 16 | | 42.3 | 26.4 | 9.2 | 7 | 9.2 | 5.7 | 277 | 170 |
| 12F3-6 untreated | 8 | | 37.6 | 26.0 | 8.9 | 1.7 | 20.7 | 5.1 | 651 | |
| C7s | 7 | | | | | | | | | |
| 12F3-6S | 7 | | | | | | | | | |
| C7 AS | 13 | | 76.7 | 13.6 | 3.3 | 1.6 | 1.9 | 2.9 | 696 | |
| 12F3-6AS | 7 | | 14.5 | 41.9 | 4.6 | 9.9 | 14.5 | 14.5 | 344 | |
| C8 untreated | 51 | 8.3 | 28.2 | 16.9 | 5.9 | 3.5 | 18.2 | 27.3 | 710 | 173 |
| 13F3-untreated | 26 | 3.4 | 21.7 | 38.3 | 9.5 | 4.2 | 14.4 | 11.9 | 494 | |
| C8 s | 23 | 2.9 | 47.8 | 25.7 | 8.3 | 6.5 | 6.6 | 5.1 | 626 | |
| 13F3-2s | 17 | 3.1 | 50.7 | 29.4 | 8.4 | 3.3 | 6.0 | 2.1 | 629 | |
| C8 AS | 123 | 13.8 | 69.2 | 11.4 | 8.0 | 7.8 | 2.1 | 1.5 | 812 | |
| 12F3-2AS | 101 | 8.2 | 63.7 | 17.8 | 6.0 | 5.8 | 4.4 | 1.8 | 886 | |

Note 50% of control colony number in the transgenic mice, and in exp. 173–correction by the AS oligo.

TABLE VI

| Drugs | Dose (mg/kg) | Minimum temperature in °C. | | | Area under baseline in °C × min | | | Number of animals | |
|---|---|---|---|---|---|---|---|---|---|
| | | C | T | Signif | C | T | Signif | C | T |
| Paraoxon | 1 | 30.4 | 32.4 | — | 2868 | 1505 | — | 1 | 1 |
| Oxotremorine | 0.15 | 29.2 ± 0.9 | 32.3 ± 0.3 | 0.02 | 909 ± 211 | 392 ± 91 | 0.04 | 3 | 3 |
| Nicotine | 10 | 33.8 ± 0.6 | 35.5 ± 0.2 | 0.006 | 160 ± 57 | 93 ± 14 | ns | 4 | 4 |

TABLE VI-continued

| Drugs | Dose (mg/kg) | Minimum temperature in °C. | | | Area under baseline in °C × min | | | Number of animals | |
|---|---|---|---|---|---|---|---|---|---|
| | | C | T | Signif | C | T | Signif | C | T |
| 8OH-DPAT | 1 | 34.8 ± 0.5 | 35.5 ± 0.3 | ns | 273 ± 97 | 78 ± 25 | 0.02 | 4 | 3 |
| Clonidine | 0.5 | 31.4 ± 1.2 | 31.6 ± 0.8 | ns | 1338 ± 207 | 1696 ± 296 | ns | 3 | 3 |

Table II: Effects of different hypothermia-inducing drugs administered intra-peritoneally to control (C) and transgenic (T) 6 months old mice. The baseline for the area above the curve of experimental points is a horizontal line drawn through the temperature of the animals before the injection. Results are expressed in means ± standard deviations, except for the high dose paraoxon experiment, which was performed only once. Statistical significance (signif) was tested with Student's t-test.

TABLE VII

Morphometric parameters of hAChE-expressing cholinergic synapses

| Parameter | Control | Transgenic |
|---|---|---|
| A. Anterior spinal cord axo-dendritic synapses | | |
| pre-synaptic length, $\mu m$ | 1.48 ± 0.65 (42) | 1.39 ± 0.66 (46) |
| space occupied by vescicles, $\mu m^2$ | 0.47 ± 0.3 (37) | 0.39 ± 029 (44) |
| pre-synaptic axon minimal diameter, $\mu m$ | 0.93 ± 0.34 (40) | 0.74 ± 0.28 (44) |
| axomic mitochondria area, $\mu m^2$ | 0.23 ± 0.13 (37) | 0.19 ± 0.1 (31) |
| post-synaptic dendrite minimal diameter, $\mu m$ | 2.44 ± 2.3 (20) | 1.61 ± 0.9 (15) P < 0.001 |
| dendritic mitochondria area, $\mu m$ | 0.52 ± 0.52 (19) | 0.35 ± 0.21 (13) <? |
| AChE stained area, $\mu m^2$ | 0.05 ± 0.04 (43) | 0.34 ± 0.90 (47) P < 0.0001 |
| B. Neuromuscular junctions | | |
| AChE stained area, $\mu m^2$ | 398 ± 136.4 (90) | 625.6 ± 227.7 (100) P < 1 × 10$^{-12}$ |
| End plate methylene blue stained area, $\mu m^2$ | 301 ± 92.1 (38) | 723.7 ± 495.3 (33) P < !? Rachel |
| Post-Synaptic fiber diameter, $\mu m$ | 30.8 ± 7.45 (69) | 35.6 ±0 5.17 (75) P < 0.005 |
| No. of post-synaptic folds/$\mu m$ NMJ | 1.4 ± 0.6 (87) | 1.8 ± 0.6 (101) |
| Total length of folds/$\mu m$ | 0.87 ± 0.3 (87) | 1.0 ± 0.25 (101) |
| Mean length of post-synaptic folds | 0.64 ± 0.06 (87) | 0.65 ± 0.4 (101) (P < 0.01 for variability in standard deviation) |
| mean area occupied by post-synaptic folds | ? | ?Rachel |

Morphometric parameters were determined as detailed under Experimental Procedures for the numbers noted in parentheses of axo-dendritic cholinergic synapses from the anterior spinal cord (A) from at least 5 adult control or transgenic mice and of neuromuscular junctions (B) Statistical significance (student's test) is noted wherever relevant, either for the values themselves or for the extent of variability between them.

REFERENCES

Aigner et al. (1995) "Overexpression of the neural growth-associated protein GAP-43 induces nerve sprouting in the adult nervous system of transgenic mice" Cell 83:269–278.

Andres et al. (1996) "Transgenic ACHE induces neuromuscular deterioration in mice" Submitted for publication.

Andrews (1988) "Human teratocarcinomas" Biochim. Biophys. Acta 948:17–36.

Anglister and McMahan (1985) "Basal lamina directs acetylcholinesterase accumulation at synaptic sites in regenerating muscle" J. Cell Biol. 101:735–743.

Anglister et al. (1994) "Acetylcholinesterase density and turnover number at frog neuromuscular junctions, with modeling of their role in synaptic function" Neuron 12:783–794.

Auld et al. (1995) "Gliotactin, a novel transmembrane protein on peripheral glia is required to form blood-brain barrier in Drosophila" Cell 81:757–767.

Baldessarini (1990) Drugs and the treatment of psychiatric disorders. In: Pharmacological Basis of Therapeutics, pp. 383–435, Gilman, Rall, Nies, and Taylor (eds) Pergamon Press, New York.

Bartels et al. (1993) "Mutation at codon 322 in the human acetylcholinesterase (ACHE) gene accounts for the YT blood group polymorphism" Science 250:1149–1152.

Ben Aziz-Aloya et al. (1993) "Expression of a human acetylcholinesterase promoter-reporter construct in developing neuromuscular junctions of Xenopus embryos" Proc. Natl. Acad. Sci. USA, 90:2471–2475.

Beeri et al. (1994) "Testicular amplification and impaired transmission of human butyrlcholinesterase cDNA in transgenic mice" Human Reprod., 9:284–292.

Beeri et al. (1995) "Transgenic expression of human acetylcholinesterase induces progressive cognitive deterioration in mice" Current Biology, 5:1063–1071.

Betz et al. (1994) in Basic Neurochem. Molecular Cell, (Raven Press Ltd, New York) 5th Ed., 681–699.

Bickel, et al. (1993) "Pharmacologic effects in vivo in brain by vector-mediated peptide drug delivery" Proc. Natl. Acad. Sci. USA 90(7):2618–2622.

Billett and Gould, (1971) "Fine ultrastructural changes in the differentiating epidermis of Xenopus laevis embryos" J. Anat. 108:465–480.

Blackwell et al. (1990) "Sequence-specific DNA binding by the c-Myc protein" Science 250:1149–1152.

Bourtchuladze et al. (1994) "Deficient long-term memory in mice with a targeted mutation of the cAMP-responsive element-binding protein" Cell 79:59–68.

Brem et al. (1993) "Polymers as controlled drug delivery devised for the treatment of malignant brain tumors" Eur. J. Pharm. Biopharm 39:2–7.

Brodbeck and Liao (1992) "Subunit assembly and glycosylation of acetylcholinesterase from mammalian brain" in Multidisciplinary approaches to Cholinesterase Functions (Shafferman and Velan, eds.), pp. 33–38. Plenum Press, New York.

Clement, J. G. (1991) "Hypothermia: limited tolerance to repeated soman administration and cross-tolerance to oxothreomorine" Biochem. Behav. 39:929–934.

Conquet et al. (1994) "Motor deficit and impairment of synaptic plasticity in mice lacking mGluR1" Nature 372:237–243.

Coyle et al. (1983) "Alzheimer's disease: a disorder of cortical cholinergic innervation" Science 219:1186–1189.

Dan and Poo, "Retrograde interactions during formation and elkination of neuromuscular synapses" Curr. Opin. in Neurobiol. 4:95–100.

De la Escalera et al. (1990) "Characterization and gene cloning of neurotactin, a Drosophila transmembrane protein related to cholinesterases" *EMBO J.* 9:3593–3601.

Dretchen et al. (1992) "Protection against cocaine toxicity by human butyrylcholinesterase (BCHE) in rats" (abstract) *FASEB J.* 6:A1282.

Drews (1975) "Cholinesterase in embryonic development" *Prog. Histochem. Cytochem* 7:1–52.

Duval, et al. (1992) "H and T subunits of acetylcholinesterase from Torpedo, expressed in COS cells, generate all types of molecular forms" *J. Cell. Biol.* 118:641–653.

Eaton and Lambert (1957) "Electromyography and electric stimulation of nerves in diseases of motor unit: observations on the myasthenic syndrome associated with malignant tumors" *JAMA* 163:1117–1124.

Eckstein (1985) "Nucleotide phosphorothioates" *Ann. Rev. Biochem.* 54:367–402.

Ehrlich et al. (1994) "Population diversity and distinct haplotype frequencies associated with ACHE and BCHE genes of Israeli Jews from Trans-Caucasian Georgia and from Europe" *Genomics* 22:288–295.

Engel and Santa (1971) "Histometric analysis of the ultrastructure of the neuromuscular junction in myasthenia gravis and in the myasthenic syndrome" *Ann. N.Y. Acad. Sci.* 183:46–63.

Fitzpatrick-McElligot and Stent (1981) "Appearance and localization of acetylcholinesterase in embryo of the leech Helodbella Triserialis" *J. Neurosci.* 1:901–907.

Fournier et al. (1992) "Drosophila acetlycholinesterase: Expression of a functional precursor in Xenopus oocytes" *Eur. J. Biochem.* 203:513–519.

Fuentes and Taylor (1993) "Control of acetylcholinesterase gene expression during myogensis" *Neuron.* 10:379–387.

Garcia-Coluna and Miledi (1995) "Effects of serotonergic agents on neuronal nicotinic acetylcholine receptors" *Proc. Natl. Acad. Sci. USA* 92:2919–2923.

Gatley (1991) "Activities of the enantiomers of cocaine and some related compounds as substrates and inhibitors of plasma butyrylcholinesterase" *Biochem. Pharmacol.* 41:1249–1254.

Gibney and Taylor (1990) "Biosynthesis of Torpedo acetylcholinesterase in mammalian cells" *J. Biol. Chem.* 265:12576–12583.

Gennari and Brodbeck (1985) "Molecular forms of acetylcholinesterase from human caudate nucleus, Comparison of salt-soluble and detergent-soluble tetrameric enzyme species" *J. Neurochem.* 44:697–704.

Gnatt et al. (1990) "Expression of alternatively terminated unusual human butyrylcholinesterase messenger RNA transcripts, mapping to chromosome 3q26-ter, in nervous system tumors" *Cancer Res.* 50:1983–1987.

Grant et al. (1992) "Imparied long-term potentiation, spatial learning, and hipocampal development in fyn mutant mice" *Science* 258:1903–1909.

Greenberg et al. (1988) "Characterization of a new megakaryocytic cell line—the DAMI cell" *Blood* 72:1968–1977.

Greensmith and Vrbova (1991) "Neuromuscular contacts in the developing rat solleus depend on muscle activity" *Dev. Brain Res.* 62:121–129.

Hall (1995) "Laminin β2 (S-Laminin): A new player at the synapse" *Science* 269:362–363.

Hall and Sanes (1993) "Synaptic structure and development: the nueromuscular junction" *Cell* 10:99–121.

Han et al. (1991) "Induction of formation of presynaptic terminals in nueroblastoma cells by synapsin IIb" *Nature* 349:697–700.

Hietanen et al. (1990) "Immunocytochemical study of the relations of acetylcholinesterase, enkephalin-, substance P-, choline acetyltransferase- and calcitonin gene-related peptide-immunoreactive structures in the ventral horn of rat spinal cord" *Histochem.* 93:473–477.

Ichtchenko et al. (1995) "Neuroligin 1: a splice site-specific ligand for beta-neurexins" *Cell* 81:435–443.

Inestrosa et al. (1987) "Acetylcholinesterase from bovine caudate nucleus is attached to membranes by a novel subunit distinct from those of acetylcholinesterases in other tissues" *J. Biol. Chem.* 262:4441–4444.

Ip et al. (1994) "Neurogenic expression of snail is controlled by separable CNS and PNS promoter elements" *Development* 120:199–207.

Isenschmid, et al. (1989) "A comprehensive study of the stability of cocaine and its metabolites" *J. Anal. Toxicol.* 13:250–256.

Jasmin et al. (1993) "Compartmentalization of acetylcholinesterase mRNA and enzyme at the vertebrate neuromuscular junction" *Neuron.* 11:467–477.

Jasmin and Gisiger (1990) "Regulation by exercise of the pool of G4 acetylcholinesterase characterizing fast muscles: opposite effect of running training in antagonist muscles" *J. of Neurosci.* 5:1444–1454.

Jennekens et al. (1992) "Deficiency of acetylcholine receptors in a case of end-plate acetylcholinesterase deficiency: A histochemical investigation" *Muscle and Nerve* 15:63–72.

Jones et al. (1993) "Mnd2: a new mouse model of inherited motor neuron disease" *Genomics* 16:669–677.

Kambam, et al. (1992) "Inhibition of pseudocholinesterase activity protects from cocaine-induced cardiorespiratory toxicity in rats" *J. Lab. Clin. Med.* 119:553–556.

Kambam, et al. (1993) "The effects of inhibition of plasma cholinesterase and hepatic microsomal enzyme activity on cocaine, benzoylecgonine, ecgonine methyl ester, and norcocaine blood levels in pigs" *J. Lab. Clin. Med.* 120:323–328.

Karpel et al. (1994) "Expression of three alternative acetylcholinesterase messenger RNAs in human tumor cell lines of different tissue origins" *Exptl. Cell. Res.* 210:268–277.

Karnovsky (1964) "The localization of cholinesterase activity in rat cardiac muscle by electron microscope" *J. Cell Biol.* 23:217–232.

Knapp et al. (1994) "A 30-week randomized controlled trial of high-dose tacrine in patients with Alzhemier's disease" *J. Am. Med. Assn.* 271:985–991.

Krejci et al. (1991) "Primary structure of a collagenic tail peptide of Torpedo acetylcholinesterase: co-expression with catalytic subunit induces the production of collagen-tailed forms in transfected cells" *EMBO J.* 10:1285–1293.

Kronman et al. (1992) "Production and secretion of high levels of recombinant human acetylcholinesterase in cultured cell lines: microheterogeneity of the catalytic subunit" *Gene* 121:295–304.

Koenig, et al (1987) "Complete cloning of the Duchenne muscular dystrophy (DMD) cDNA and preliminary genomic organization of the DMD gene in normal and affected individuals" *Cell* 50:509–517.

Lambert and Elmquist, (1971) "Quantal components of end plate potentials in the myasthenic syndrome" *Ann. NY Acadc. Sci.* 183:183–199.

Lapidot-Lifson et al. (1992) "Cloning and antisense oligodeoxynucleotide inhibition of a human homolog of cdc2 required in hematopoiesis" *Proc. Natl. Acad. Sci. USA* 89: 579–583.

Lapidot-Lifson et al. (1989) "Co-amplification of human acetylcholinesterase and butyrylcholinesterase in blood cells: Correlation with various leukemias and abnormal megakaryocytopoiesis" *Proc. Natl. Acad. Sci. USA* 86: 4715–4717.

Legay et al. (1993a) Cloning and expression of a rat acetylcholinesterase subunit: generation of multiple molecular forms, complementarity with a Torpedo collagenic subunit" *J. Neurochem.* 60:337–346.

Legay et al. (1993b) "Expression of a cDNA encoding the glycolipid-anchored form of rat acetylcholinesterase" *FEBS Lett* 315:163–166.

Lev-Lehman et al. (1994) "Antisense inhibition of acetylcholinesterase gene expression causes transient hematopoietic alterations in vivo" *Gene Therapy*, 1:127–135.

Li et al. (1991) "Gene structure of mammalian acetylcholinesterase: Alternative exons dictate tissue specific expression" *J. Biol. Chem.* 266:23083–23090.

Li et al. (1993) "Tissue-specific expression and alternative mRNA processing of the mammalian acetylcholinesterase gene" *J. Biol. Chem.* 268:5790–5797.

Liang and Pardee (1992) "Differential display of eukaryotic messenger RNA by means of the polymerase chain reaction" *Science* 257:967–971.

Liao et al. (1992) "Different glycosylation in acetylcholinesterase from mammalian brain and erythrocytes" *J. Neurochem.* 58:1230–1238.

Loewenstein-Lichtenstein et al. (1995) "Genetic predisposition to adverse consequences of anti-cholinesterases in "Atypical" BCHE carriers" *Nature/Medicine* 1:1082–1085.

Loewenstein et al. (1993) "Molecular dissection of cholinesterase domains responsible for carbamate toxicity" *Chem.-Biol. Interactions* 87:209–216.

Low (1987) "Biochemistry of the glycosyl-phospatidylinositol membrane protein anchor" *Biochem. J.* 244:1–13.

Lyons and Slater (1991) "Structure and function of the neuromuscular function in young adult mdx mice" *J. Neurocytol* 20:969–981.

McNamara and Skelton (1993) "The neuropharmacological and neurochemical basis of place learning in the Morris water maze" *Brain Res. Reviews* 18:33–49.

Massoulie et al. (1992) (Shafferman and Velan, eds., Plenum Press, N.Y.) pp. 285–288.

Massoulie et al. (1993) "Molecular and cellular biology of cholinesterases" *Progress in Neurobiology* 41, 31–91.

Masu et al. (1993) "Disruption of the CNTF gene results in motor neuron degeneration" *Nature* 365:27–32.

Meneely et al. (1989) "Effects of the organophosphate insecticides Diazinon and Parathion on bobwhite quail embryos: skeletal defects and acetylcholinesterase activity" *J. Exp. Zool.* 252:60–70.

Millard and Broomfield (1995) "Anticholinesterases: medical applications of neurochemical principles" *J. Neurochem.* 64:1909–1918.

Morris et al. (1981) "Place navigation impaired in rats with hippocampal lesions" *Nature* 297:681–682.

Mutero et al. (1995) "Promoter elements of the mouse acetylcholinesterase gene" *J. Biol. Chem.* 270:1866–1872.

Navaratnam (1991) "Anomalous molecular form of acetylcholinesterase in cerebrospinal fluid in histologically diagnosed Alzheimer's disease" *Lancet* 337:447–450.

Neville et al. (1992) "Intra-molecular relationships in cholinesterases revealed by oocyte expression of site-directed and natural variants of human BChE" *EMBO J.* 11:1641–1649.

Newhouse et al. (1994) "Modeling the nicotinic receptor loss in dementia using the nicotinic agonist mecamylamine—effects on human cognitive functioning" *Drug. Dev. Res.* 31:71–79.

Nishikawa and Sasaki (1993) "Secretion of chondroitin sulfate from embryonic epidermal cells in *Xenopus laevis*" *J. Histochem. Cytochem.* 9:1373–1381.

Noakes et al. (1995) "Aberrant differentiation of neuromuscular junctions in mice lacking S-laminin/laminin β2" *Nature* 374:258–262.

Pardridge, et al. (1992) "Blood-brain barrier and new approaches to brain drug delivery" *West J. Med.* 156(3):281–286.

Pardridge (1992) "Recent Developments in peptide drug delivery to the brain" *Pharm. Toxicol.* 71(1):3–10.

Patinkin et al. (1990) Manipulations of cholinesterase gene expression modulate murine megakaryocytopoiesis in vitro" *Mol. Cell. Biol.* 10:6046–6050.

Paoletti et al. (1992) "Acetylcholinesterase in murine erythroleukemia (Friend) cells: evidence for megakaryocyte-like expression and potential growth-regulatory role of enzyme activity" *Blood* 79:2873–2879.

Pavlath et al. (1989) "Localizationof muscle gene products in nuclear domains" *Nature* 337:570–573.

Plump et al. (1992) "ApoE-deficient mice have been created by homologous recombination in ES cells" *Cell* 71:343–353.

Pressman-Schwartz et al. (1992) "A 69-kDa RNA-binding protein from Xenopus oocytes recognizes a common motif in two vegetally localized maternal mRNAs" *Proc. Natl. Acad. Sci. USA* 89:11895–11899.

Prody et al. (1989) "De novo amplification within a "silent" human cholinesterase gene in a family subjected to prolonged exposure to organophosphorous insecticides" *Proc. Natl. Acad. Sci. USA* 86:690–694.

Prody et al. (1987) "Isolation and charaterization of full-length cDNA clones coding for cholinesterase from fetal human tissue" *Proc. Natl. Acad. Sci. USA* 84:3555–3559.

Ralston and Hall (1989) "Transfer of a protein encoded by a single nucleus to nearby nuclei in multinucleated mytobes" *Nature* 244 :1066–1069.

Rachinsky et al. (1990) "Molecular cloning of mouse acetylcholinesterase: tissue distribution of alternatively spliced mRNA species" *Neuron* 5:317–327.

Roberts et al. (1991) "Bovine brain acetylcholinesterase primary sequence involved in intersubunit disulfide linkages" *J. Biol Chem.* 266:7481–7487.

Rubinstein et al. (1984) "A lymphocyte cell line that makes serum cholinesterase instead of acetylcholinesterase" *Biochem Gen* 22:1171–1175.

Sakimura et al. (1995) "Reduced hippocampal LTP and spatial learning in mice lacking NMDA receptor ε1 subunit" *Nature* 373:151–155.

Salpeter (1967) "Electron microscope radioautography as a quantitative tool in enzyme cyotchemistry I: The distribution of acetylcholinesterase at motor endplates of a vertebrate twitch muscle" *J. Cell. Biol.* 32:379–389.

Schaeffer et al. (1994) "Synapsin IIa accelerates functional development of neuromuscular synapses" *Proc. Natl. Acadl. Sci. USA* 91:3882–3886.

Schmidt et al. (1990) "The cytomegalovirus enhancer: a panactive control element in transgenic mice" *Molec. Cell. Biol.* 10:4406–4411.

Schwarz et al. (1995) "Engineering of human cholinesterases explains and predicts diverse consequences of administration of various drugs and poisons" *Pharmacology and Therapeutics* 67:283–322.

Seidman and Soreq (1996) "Transgenic Xenopus microinjection methods and developmental neurobiology" in *Humana Press*, Neuromethods series, (in press).

Seidman et al. (1995) "Synaptic and epidermal accumulations of human acetylcholinesterase are encoded by alternative 3'-terminal exons" *Mol. Cell Biol.* 14:459–473.

Seidman et al. (1994) "Overexpressed monomeric human acetylcholinesterase induces subtle ultrastructural modifications in developing meuromuscular junctions of *Xenopus laevis* embryos" *J. Neurochem.* 62:1670–1681.

Shani (1985) "Tissue specific expression of rat myosin light chain 3 gene in transgenic mice" *Nature* 314:283–286.

Shani et al. (1992) "Expression of human serum albumin in the milk of transgenic mice" *Transgen. Res.* 1:192–208.

Shapira et al. (1994) "Transgenic engineering of neuromuscular junctions in *Xenopus laevis* embryos transiently overexpressing key cholinergic proteins" *Proc. Natl. Acad. Sci. USA* 91:9072–9076.

Sher et al. (1990) "Voltage-operated calcium channels in small cell lung carcinoma cell lines—pharmacological, functional and immunological properties" *Cancer Res.* 50:3892–3896.

Sikorav et al. (1988) "Complex alternative splicing of acetylcholinesterase transcripts in Torpedo electric organ: primary structure of the precursor of the glycolipid-anchored dimeric form" *EMBO J.* 7:2983–2993.

Silva et al. (1992) "Impaired spatial learning in α-calcium-calmodulin kinase II mutant mice" *Science* 257:206–211.

Simpson et al. (1994) "Prostaglandins and hypothalamic neurotransmitter receptors involved in hypothermia: a critical evaluation" *Neurosci. Behavior Rev.* 18:1–20.

Sokol et al. (1991) "Injected Wnt RNA induces a complete body axis in Xenopus embryos" *Cell* 67:741–752.

Soreq et al. (1990) "Molecular cloning and construction of the coding region for human acetylcholinesterase reveals a G,C rich attenuating structure" *Proc. Natl. Acad. Sci. USA* 87:9688–9692.

Soreq et al. (1991) "Role for cholinesterases in Tumorigenesis?" *Cancer Cells* 3:511–516.

Soreq et al. (1989) "Expression and tissue specific assembly of cloned human butyrylcholine esterase in microinjected *Xenopus laevis* oocytes" *J. Biol. Chem.* 264:10608–10613.

Soreq and Zakut (1993) "Human Cholinesterases and anticholinesterases" *Academic Press.*

Thomas et al. (1982) "Anterior horn cell dysfunction in Alzheimer's disease" *J. Neurol. Neurosurg. and Psychiatry* 45:378–381.

Toutant et al. (1990) "Molecular forms of acetylcholinesterase in two sublines of human erythroleukemia K562 cells—sensitivity or resistance to phosphatidylinositol-specific phospholipase C and biosynthesis" *Euro J. Biochem.* 187:31–38.

Ushkariov et al. (1992) "Neurexins: synaptic cell surface proteins related to the α-latrotoxin receptor and laminin" *Science* 257:50–56.

Velan et al. (1991a) "Recombinant human acetylcholinesterase is secreted from transiently transfected 293 cells as a soluble globular enzyme," *Cell. Mol. Neurobiol.* 11:143–156.

Velan et al. (1991b) "The effect of elimination of intersubunit disulfide bonds on the activity, assembly and secretion of recombinant human acetylcholinesterase" *J. Biol. Chem.* 266:23977–23984.

Westaway et al. (1994) "Degeneration of skeletal muscle, peripheral nerves, and the central nervous system in transgenic mice overexpressing wild-type prion proteins" *Cell* 76:117–129.

Wokke et al. (1990) "Morphological changes in the human end plate with age" *J. of Neurological Sciences* 95:291–310.

Wurtman (1992) "Choline metabolism as a basis for the selective vulnerability of cholinergic neurons" *TINS* 5:117–112.

Zakut et al. (1990) "Acetylcholinesterase and butyrylcholinesterase genes coamplify in primary ovarian carcinomas" *J. Clin. Invest.* 86:900–908.

Zakut et al. (1991) "Modified properties of serum cholinesterases in primary carcinomas" *Cancer Res.* 61:727–737.

Zakut et al. (1992) "In vivo gene amplification in non-carcerous cells; cholinesterase genes and oncogenes amplify in throbocytopernia associated with Lupus Erythematosus" *Mutation Research* 276:275–284.

Zakut et al. (1991) "Chorionic villus cDNA library displays expression of butyrylcholinesterase: putative disposition for ecological danger" *Prenatal Diagnosis* 11:597–607.

Zakut et al. (1994) "Turning of nerve growth cones induced by neurotransmitters" *Nature* 368:140–144.

Zon et al. (1991) "Expression of GATA-binding proteins during embryonic development in *Xenopus laevis*" *Proc. Natl. Acad. Sci. USA* 88:10642–10646.

Aizenman, E. (1988) *Science* 239:1293–1296.

Ariel and Daw (1982a) *J. Physiol.* 324:135–160.

Ariel and Daw (1982b) *J. Physiol.* 324:161–186.

Bierer et al. (1995) *J. Neurochem.* 64:749–760.

Connell et al. (1991) *Proc. Natl. Acad. Sci. USA* 88:723–726.

Darboux et al. (1996) *EMBO J.* 15:4835–4843.

Ehrlich et al. (1992) *Genomics* 13:1192–1197.

Freeman, J. A. (1977) *Nature* 269:218–222.

Gavrieli et al. (1992) *J. Cell Biol.* 119:493–501.

Humphries et al. (1992) *Science* 256:804–808.

Hutchins, J. B. (1987) *Exp. Eye Res.* 45:1–38.

Jordan et al. (1993) *Nature Genet.* 4:54–57.

Kawasaki et al. (1993) Uniformly modified 2'-deoxy-2'-fluoro phosphorothioate oligonucleot ides as nuclease-resistant antisense compounds with high affinity and specifity for RNA targets, *J. Med. Chem.*, 36:831.

Langdon and Freeman (1987) *J. Neurosci.* 7:760–773.

Layer et al. (1992) *Cell Tissue Res.* 268:409–418.

Layer et al. (1993) *Cell Tissue Res.* 273, 219–226.

Layer, P. G. (1995) *Alz. Dis. Assoc. Disord.* 9:29–36.

Lipton et al. (1988) *Science* 239:1293–1296.

Lolley et al. (1994) *Invest. Ophthalmol. Vis. Sci.* 35, 358–362.

Marc, R. E. (1986) *Vision Res.* 26:223–238.

Masland and Tauchi (1986) *Trends Neurosci.* 9:218–223.

McGuire et al. (1995) *Hum. Genet.* 95:71–74.

Millar et al. (1985) *Neurosci. Lett.* 61:311–316.

Mullen and LaVail (1976) *Science* 192:799–801.

Pittler and Baehr (1991) *Proc. Natl. Acad. Sci. USA* 88:8322–8326.

Robertson and Yu (1993) *NIPS* 8:266–272.

Schmidt, J. (1988) *Int. Rev. Neurobiol.* 30:1–38.

Small et al. (1995) *J. Neurosci.* 15:144–151.

Shatz, C. J. (1996) *Proc. Natl. Acad. Sci. USA* 93:602–608.

Shastry, B. S. (1994) *Amer. J. Med. Gen.* 53:467–474.

Sung et al. (1994) *J. Neurosci.* 14:5818–5833.

Vaney et al. (1981) *J. Comp. Neurol.* 199:373–391.

We claim:

1. A recombinant expression vector comprising a DNA sequence encoding human acetylcholinesterase (AChE) and a human promoter as set forth in SEQ ID No:7.

2. A recombinant vector as set forth in claim 1 wherein the DNA encoding human acetylcholinesterase has the nucleotide sequence set forth in SEQ ID NO:1 and which encodes the amino acid sequence set forth in SEQ ID NO:2.

3. A recombinant vector as set forth in claim 1 wherein the DNA encoding human acetylcholinesterase has all or part of the nucleotide sequence set forth in SEQ ID NO:3, and which encodes an amino acid sequence as set forth in SEQ ID NO:4.

4. A recombinant vector as set forth in claim 1 wherein the DNA encoding human acetylcholinesterase has the nucleotide sequence set forth in SEQ ID NO:5, and which encodes the amino acid sequence set forth in SEQ ID NO:6.

5. An isolated DNA having the sequence set forth in SEQ ID No:7.

6. A eukaryotic host cell transformed with the expression vector according to claim 1 and isolated progeny thereof, said host cell being capable of expressing AChE when cultured under conditions promoting AChE expression.

7. An isolated DNA having a sequence as set forth in SEQ ID No: 7 comprising a gene conferring arsenite resistance.

* * * * *